（12）United States Patent
Kane et al.

(10) Patent No.: US 10,532,214 B2
(45) Date of Patent: Jan. 14, 2020

(54) IMPLANTABLE DEVICE HEADER AND METHOD

(71) Applicant: Cardiac Pacemakers, Inc., St. Paul, MN (US)

(72) Inventors: Michael J. Kane, Roseville, MN (US); John O'Rourke, Co. Tipperary (IE)

(73) Assignee: Cardiac Pacemakers, Inc., St. Paul, MN (US)

( * ) Notice: Subject to any disclaimer, the term of this patent is extended or adjusted under 35 U.S.C. 154(b) by 62 days.

(21) Appl. No.: 15/206,923

(22) Filed: Jul. 11, 2016

(65) Prior Publication Data

US 2017/0001021 A1    Jan. 5, 2017

Related U.S. Application Data

(63) Continuation of application No. 13/711,670, filed on Dec. 12, 2012, now Pat. No. 9,387,335.

(60) Provisional application No. 61/569,936, filed on Dec. 13, 2011.

(51) Int. Cl.
  *A61N 1/375*    (2006.01)
  *A61N 1/372*    (2006.01)

(52) U.S. Cl.
  CPC ........... *A61N 1/3752* (2013.01); *A61N 1/375* (2013.01); *A61N 1/37217* (2013.01)

(58) Field of Classification Search
  CPC .... A61N 1/375; A61N 1/3754; A61N 1/3756; A61N 1/3758; A61N 1/3968; A61N 1/372
  USPC .......................................................... 607/36
  See application file for complete search history.

(56) References Cited

U.S. PATENT DOCUMENTS

| | | | |
|---|---|---|---|
| 4,262,673 | A | 4/1981 | Kinney et al. |
| 4,479,489 | A | 10/1984 | Tucci |
| 6,006,135 | A | 12/1999 | Kast et al. |
| 6,080,188 | A | 6/2000 | Rowley et al. |
| 7,309,262 | B2 | 12/2007 | Zart et al. |
| 7,317,946 | B2 | 1/2008 | Twetan et al. |

(Continued)

FOREIGN PATENT DOCUMENTS

| CN | 101454963 A | 6/2007 |
| CN | 201161061 Y | 12/2008 |

(Continued)

OTHER PUBLICATIONS

"U.S. Appl. No. 13/711,661, Non Final Office Action dated Dec. 6, 2013", 8 pgs.

(Continued)

*Primary Examiner* — William J Levicky
*Assistant Examiner* — Minh Duc G Pham
(74) *Attorney, Agent, or Firm* — Schwegman Lundberg & Woessner, P.A.

(57) ABSTRACT

Systems and methods for implantable medical devices and headers are described. In an example, an implantable medical device includes a device container including an electronic module within the device container. A modular header core includes a header core module including at least one bore hole configured to receive a lead, an antenna attachment module coupled to the header core, and an antenna engaged with the antenna attachment module. The antenna attachment module is configured to locate the antenna in a selected position with respect to the header core module.

17 Claims, 28 Drawing Sheets

(56) References Cited

U.S. PATENT DOCUMENTS

| | | | |
|---|---|---|---|
| 7,654,843 B2 | 2/2010 | Olson et al. | |
| 7,736,191 B1 | 6/2010 | Sochor | |
| 8,355,785 B1 | 1/2013 | Hammond et al. | |
| 8,768,467 B2 | 7/2014 | Kane et al. | |
| 8,849,420 B2 | 9/2014 | Kane et al. | |
| 8,903,473 B2 | 12/2014 | Rogers et al. | |
| 9,345,893 B2 | 5/2016 | Kane et al. | |
| 9,387,335 B2 | 7/2016 | Kane et al. | |
| 2004/0027306 A1 | 2/2004 | Amundson et al. | |
| 2004/0116976 A1 | 6/2004 | Spadgenske | |
| 2005/0203583 A1* | 9/2005 | Twetan | A61N 1/37229 607/36 |
| 2005/0203584 A1 | 9/2005 | Twetan et al. | |
| 2006/0020296 A1 | 1/2006 | Fioretti | |
| 2006/0068136 A1 | 3/2006 | Kinjou et al. | |
| 2006/0150371 A1 | 7/2006 | Martin et al. | |
| 2006/0224208 A1 | 10/2006 | Naviaux | |
| 2006/0259092 A1 | 11/2006 | Spadgenske et al. | |
| 2007/0100386 A1 | 5/2007 | Tronnes et al. | |
| 2007/0190866 A1 | 8/2007 | Zart et al. | |
| 2007/0270007 A1 | 11/2007 | Mueller et al. | |
| 2007/0288065 A1 | 12/2007 | Christman et al. | |
| 2008/0065181 A1 | 3/2008 | Stevenson | |
| 2008/0303728 A1 | 12/2008 | Lee et al. | |
| 2009/0042409 A1 | 2/2009 | Yuan et al. | |
| 2010/0035453 A1 | 2/2010 | Tronnes et al. | |
| 2010/0045464 A1 | 2/2010 | Knopf et al. | |
| 2010/0099959 A1 | 4/2010 | Deehr et al. | |
| 2010/0100157 A1 | 4/2010 | Nghiem et al. | |
| 2010/0109958 A1* | 5/2010 | Haubrich | A61N 1/37229 343/718 |
| 2010/0109966 A1 | 5/2010 | Mateychuk et al. | |
| 2010/0125320 A1 | 5/2010 | Polkinghorne et al. | |
| 2010/0168817 A1 | 7/2010 | Yamamoto et al. | |
| 2010/0267265 A1 | 10/2010 | Dilmaghanian | |
| 2011/0104955 A1 | 5/2011 | Seeley et al. | |
| 2011/0156306 A1 | 6/2011 | Morris et al. | |
| 2011/0304520 A1 | 12/2011 | Djordjevic et al. | |
| 2012/0271388 A1 | 10/2012 | Padsalgikar et al. | |
| 2012/0322317 A1 | 12/2012 | Seeley et al. | |
| 2013/0150915 A1 | 6/2013 | Kane et al. | |
| 2013/0150916 A1 | 6/2013 | Kane et al. | |
| 2013/0150917 A1 | 6/2013 | Kane et al. | |
| 2013/0150937 A1 | 6/2013 | Kane et al. | |

FOREIGN PATENT DOCUMENTS

| | | | |
|---|---|---|---|
| CN | 104114228 A | 10/2014 | |
| CN | 104114229 A | 10/2014 | |
| CN | 104114230 A | 10/2014 | |
| CN | 104114231 A | 10/2014 | |
| CN | 104114230 B | 8/2016 | |
| CN | 104114231 B | 9/2016 | |
| CN | 104114229 B | 10/2016 | |
| EP | 2244337 A1 | 10/2010 | |
| JP | 62254770 A | 11/1987 | |
| JP | 0900642 A | 1/1997 | |
| JP | 2006263468 A | 10/2006 | |
| JP | 2006311372 A | 11/2006 | |
| JP | 2008537386 A | 9/2008 | |
| JP | 2012505721 A | 3/2012 | |
| JP | 2015500128 A | 1/2015 | |
| JP | 2015500129 A | 1/2015 | |
| JP | 2015500130 A | 1/2015 | |
| JP | 2015502825 A | 1/2015 | |
| JP | 5992533 B2 | 9/2016 | |
| JP | 6092893 | 2/2017 | |
| WO | WO-9916504 A1 | 4/1999 | |
| WO | WO-2012071402 | 5/2012 | |
| WO | WO-2013090300 A2 | 6/2013 | |
| WO | WO-2013090300 A3 | 6/2013 | |
| WO | WO-2013090301 A2 | 6/2013 | |
| WO | WO-2013090301 A3 | 6/2013 | |
| WO | WO-2013090302 A1 | 6/2013 | |
| WO | WO-2013090304 A1 | 6/2013 | |

OTHER PUBLICATIONS

"U.S. Appl. No. 13/711,661, Response filed Aug. 19, 2013 to Restriction Requirement dated Jul. 18, 2013", 5 pgs.

"U.S. Appl. No. 13/711,661, Restriction Requirement dated Jul. 18, 2013", 6 pgs.

"U.S. Appl. No. 13/711,664, Non Final Office Action dated Dec. 3, 2013", 14 pgs.

"U.S. Appl. No. 13/711,664, Response filed Oct. 16, 2013 to Restriction Requirement dated Sep. 16, 2013", 7 pgs.

"U.S. Appl. No. 13/711,664, Restriction Requirement dated Sep. 16, 2013", 7 pgs.

"U.S. Appl. No. 13/711,670, Advisory Action dated Dec. 18, 2014", 3 pgs.

"U.S. Appl. No. 13/711,670, Examiner Interview Summary dated Nov. 27, 2015", 3 pgs.

"U.S. Appl. No. 13/711,670, Final Office Action dated Sep. 18, 2014", 11 pgs.

"U.S. Appl. No. 13/711,670, Non Final Office Action dated Aug. 27, 2015", 13 pgs.

"U.S. Appl. No. 13/711,670, Non Final Office Action dated Dec. 23, 2013", 8 pgs.

"U.S. Appl. No. 13/711,670, Notice of Allowance dated Mar. 11, 2016", 8 pgs.

"U.S. Appl. No. 13/711,670, Response filed Jan. 16, 2015 to Final Office Action dated Sep. 18, 2014", 19 pgs.

"U.S. Appl. No. 13/711,670, Response filed Mar. 24, 2014 to Non Final Office Action dated Dec. 23, 2013", 13 pgs.

"U.S. Appl. No. 13/711,670, Response filed Aug. 19, 2013 to Restriction Requirement dated Jul. 18, 2013", 5 pgs.

"U.S. Appl. No. 13/711,670, Response filed Nov. 18, 2014 to Final Office Action dated Sep. 18, 2014", 19 pgs.

"U.S. Appl. No. 13/711,670, Response filed Nov. 25, 2015 to Non Final Office Action dated Aug. 27, 2015", 21 pgs.

"U.S. Appl. No. 13/711,670, Restriction Requirement dated Jul. 18, 2013", 7 pgs.

"U.S. Appl. No. 13/711,680, Non Final Office Action dated Sep. 20, 2013", 18 pgs.

"U.S. Appl. No. 13/711,680, Notice of Allowance dated Feb. 21, 2014", 7 pgs.

"U.S. Appl. No. 13/711,680, Response filed Dec. 20, 2013 to Non Final Office Action dated Sep. 20, 2013", 13 pgs.

"Chinese Application Serial No. 201280069675.0, Office Action dated Apr. 28, 2015", with English translation, 23 pgs.

"International Application Serial No. PCT/US2012/069038, International Search Report dated Jul. 9, 2013", 6 pgs.

"International Application Serial No. PCT/US2012/069038, International Written Opinion dated Jul. 9, 2013", 7 pgs.

"International Application Serial No. PCT/US2012/069038, Invitation to Pay Additional Fees and Partial Search Report dated Apr. 11, 2013", 4 pgs.

"International Application Serial No. PCT/US2012/069039, International Search Report dated Jul. 9, 2013", 6 pgs.

"International Application Serial No. PCT/US2012/069039, International Written Opinion dated Jul. 9, 2013", 10 pgs.

"International Application Serial No. PCT/US2012/069039, Invitation to Pay Additional Fees and Partial Search Report dated Apr. 10, 2013", 5 pgs.

"International Application Serial No. PCT/US2012/069043, International Search Report dated Mar. 25, 2013", 3 pgs.

"International Application Serial No. PCT/US2012/069043, Written Opinion dated Mar. 25, 2013", 4 pgs.

"International Application Serial No. PCT/US2012/069046, International Search Report dated Apr. 26, 2013", 4 pgs.

"International Application Serial No. PCT/US2012/069046, Written Opinion dated Apr. 26, 2013", 6 pgs.

"Japanese Application Serial No. 2014-547356, Office Action dated Jun. 23, 2015", with English translation, 4 pgs.

(56) References Cited

OTHER PUBLICATIONS

"U.S. Appl. No. 13/711,661, Advisory Action dated Dec. 17, 2014", 6 pgs.
"U.S. Appl. No. 13/711,661, Final Office Action dated Sep. 16, 2014", 9 pgs.
"U.S. Appl. No. 13/711,661, Non Final Office Action dated Jul. 6, 2015", 7 pgs.
"U.S. Appl. No. 13/711,661, Notice of Allowance dated Jan. 20, 2016", 8 pgs.
"U.S. Appl. No. 13/711,661, Response filed Jan. 16, 2015 to Final Office Action dated Sep. 16, 2014", 14 pgs.
"U.S. Appl. No. 13/711,661, Response filed Apr. 7, 2014 to Non Final Office Action dated Dec. 6, 2013", 11 pgs.
"U.S. Appl. No. 13/711,661, Response filed Oct. 5, 2015 to Non Final Office Action dated Jul. 6, 2015", 12 pgs.
"U.S. Appl. No. 13/711,661, Response filed Nov. 17, 2014 to Final Office Action dated Sep. 16, 2014", 12 pgs.
"U.S. Appl. No. 13/711,664, Notice of Allowance dated May 23, 2014", 8 pgs.
"U.S. Appl. No. 13/711,664, Response filed Apr. 3, 2014 to Non Final Office Action dated Dec. 3, 2013", 15 pgs.
"U.S. Appl. No. 13/711,661, Non Final Office Action dated Jul. 6, 2015", 8 pgs.
"Chinese Application Serial No. 201280069550.8, Office Action dated Apr. 24, 2015", with English translation, 15 pgs.
"Chinese Application Serial No. 201280069554.6, Office Action dated May 18, 2015", English Translation Included, 31 pgs.
"Chinese Application Serial No. 201280069574.3, Office Action dated Mar. 20, 2015", with English translation, 7 pgs.
"European Application Serial No. 12806297.3, Communication Pursuant to Article 94(3) EPC dated Apr. 4, 2017", 3 pgs.
"European Application Serial No. 12806297.3, Response filed Jul. 26, 2017 to Communication Pursuant to Article 94(3) EPC dated Apr. 4, 2017", 5 pgs.
"European Application Serial No. 12809462.0, Communication Pursuant to Article 94(3) EPC dated Sep. 6, 2017", 5 pgs.
"International Application Serial No. PCT/US2012/069038, International Preliminary Report on Patentability dated Jun. 26, 2014", 9 pgs.
"International Application Serial No. PCT/US2012/069039, International Preliminary Report on Patentability dated Jun. 26, 2014", 12 pgs.
"International Application Serial No. PCT/US2012/069043, International Preliminary Report on Patentability dated Jun. 26, 2014", 6 pgs.
"International Application Serial No. PCT/US2012/069046, International Preliminary Report on Patentability dated Jun. 26, 2014", 8 pgs.
"Japanese Application Serial No. 2014-547354, Office Action dated Jun. 16, 2015", With English Translation, 6 pgs.
"Japanese Application Serial No. 2014-547354, Office Action dated Aug. 23, 2016", with English translation, 4 pgs.
"Japanese Application Serial No. 2014-547354, Response filed Sep. 15, 2015 to Office Action dated Jun. 16, 2015", With English Claims, 11.
"Japanese Application Serial No. 2014-547354, Response filed Nov. 21, 2016 to Office Action dated Aug. 23, 2016", W/ English Translation of Claims, 7 pgs.
"Japanese Application Serial No. 2014-547355, Office Action dated Jun. 2, 2015", With English Translation, 13 pgs.
"Japanese Application Serial No. 2014-547357, Office Action dated Jun. 2, 2015", With English Transaltion, 8 pgs.

* cited by examiner

| PARAMETER | VALUE (nm) | PARAMETER | VALUE (uin) |
|---|---|---|---|
| Sa | 8477 | Sa | 334 |
| Sq | 10483 | Sq | 413 |
| Sy | 1.13E+5 | Sy | 4440 |
| Smin | -85539 | Smin | -3368 |
| Smax | 27239 | Smax | 1072 |
| S3A | 4.26E+11 | S3A | 6.6E+8 |

IMPLANTABLE DEVICE HEADER AND METHOD

CLAIM OF PRIORITY

This application is a continuation of U.S. application Ser. No. 13/711,670, filed Dec. 12, 2012, now issued as U.S. Pat. No. 9,387,335, which claims the benefit of priority under 35 U.S.C. § 119(e) of Kane et al., U.S. Provisional Patent Application Ser. No. 61/569,936, entitled "IMPLANTABLE DEVICE HEADER. AND METHOD", filed on Dec. 13, 2011, each of which is herein incorporated by reference in its entirety.

TECHNICAL FIELD

Various embodiments described herein relate to apparatus, systems, and methods associated with implantable medical devices.

BACKGROUND

An ambulatory medical device, such as an implantable medical device (IMD), can be configured for implant in a subject, such as a patient. An IMD can be configured to be coupled to a patient's heart such as via one or more implantable leads. Such an IMD can obtain diagnostic information or generate therapy to be provided to the patient, such as via the coupled implantable lead. Examples of such devices can include cardiac rhythm management (CRM) devices including one or more of implantable pacemakers, implantable cardioverter-defibrillators (ICDs), cardiac resynchronization therapy devices (CRTs), neural stimulators, or one or more other devices. Such devices can include one or more electrodes coupled, such as via the implantable lead, to circuitry located on or within the IMD. Such circuitry can be configured to monitor electrical activity, such as to obtain information indicative of electrical activity of the heart. In one configuration, IMDs have a header that is coupled to a container that houses much of the electronics of the IMD.

DETAILED DESCRIPTION

In the following detailed description, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized and structural, logical, and electrical changes may be made.

Figure 1:
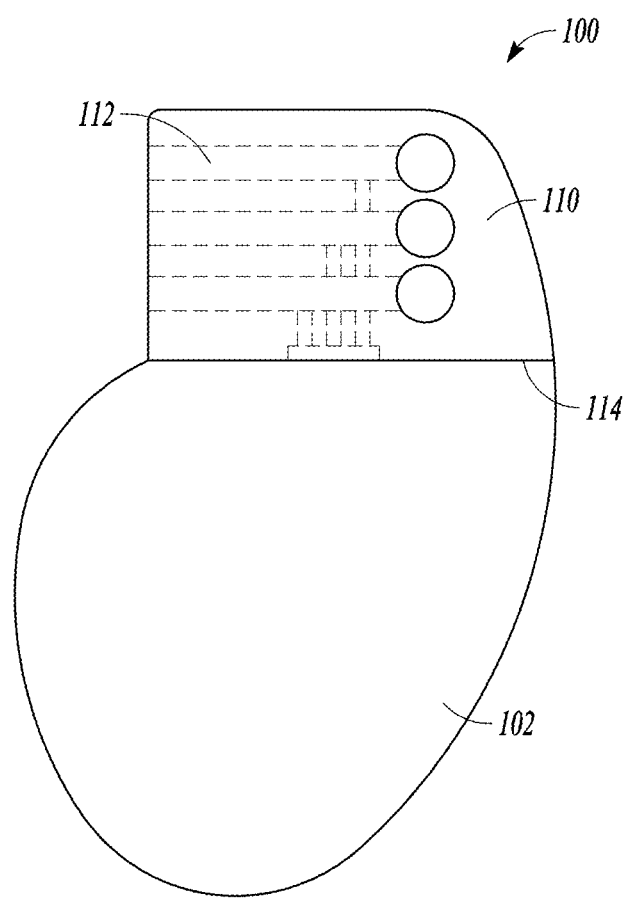
FIG. 1 shows an example IMD according to an embodiment of the invention.

FIG. 1 shows an example of an IMD 100 according to an embodiment of the present disclosure. Examples of IMDs 100 can include cardiac rhythm management (CRM) devices including one or more of implantable pacemakers, implantable cardioverter-defibrillators (ICDs), cardiac resynchronization therapy devices (CRTs), or one or more other devices. Other examples of IMDs 100 can include neurostimulators including spinal cord stimulators, deep brain stimulators, peripheral nerve stimulators, or other similar devices. The IMD 100 includes a metallic device container 102 and a header 110. In the example shown, the header 110 includes a number of electrical contacts 112 to couple to additional components such as lead wires. Although the embodiment shown in FIG. 1 includes three electrical contacts 112, other embodiments of the present disclosure can include other configurations, such as configurations include more or less than three electrical contacts 112. The header 110 is attached to the metallic device container 102 at a surface 114 of the metallic device container 102.

In one example, the header 110 is formed from a polymer material. A polymer can provide a number of desirable features, such as biocompatibility, strength, resilience, and ease of manufacturing. In one example, the header 110 is molded separately from the metallic device container 102, and later bonded to the metallic device container 102 using an adhesive. In a second example, the header 110 is molded in place (overmolded) and contacts the surface 114 of the metallic device container 102 during a curing or hardening process. In the second example, no additional adhesive is needed to attach the header 110 to the metallic device container 102.

In one example, the polymer material of the header 110 includes a thermoset material. In one example, the thermoset material of the header 110 includes a polyurethane thermoset. In one example, a polyurethane thermoset includes combinations of polyisocyanate and polyol.

In another example, the thermoset material of the header 110 includes an epoxy material. Epoxy is a copolymer; that is, it is formed from two different chemicals, namely a resin and a hardener. The resin may consist of monomers or short chain polymers with an epoxide group at either end. The hardener may consist of polyamine monomers, for example Triethylenetetramine (TETA). When these compounds are mixed together, the amine groups react with the epoxide groups to form a covalent bond. Each NH group can react with an epoxide group, so that the resulting polymer is heavily crosslinked, and is thus rigid and strong. The process of polymerization is called "curing," and can be controlled through temperature, choice of resin and hardener compounds, and the ratio of said compounds. The process can take minutes to hours. Thermoset materials other than epoxies may cure using other polymer crosslinking reactions.

In one example, the epoxy is injected into a mold and cured into the final desired configuration. As noted above, one method molds the header 110 separately and later bonds the header to the metallic device container 102. Another method molds the header 110 while in contact with the metallic device container 102. In one example, a ratio of resin to hardener is approximately 2:1 by volume. In one example the mold is preheated to approximately 50° C. prior to injection.

In one example a temperature of one or more portions of the epoxy is raised prior to injecting the components into the mold. In one example, the epoxy is preheated to approximately 50° C. prior to injection. Raising a temperature of an epoxy component can reduce a viscosity of the component, thereby facilitating improved properties such as throughput time and quality of the molded header (e.g. fewer air bubbles and better penetration into surface texture of the surface 114 of the metallic device container 102). In one example, one or more portions of the epoxy is injected at a pressure of less than 0.034 megapascals (MPa).

In one example the epoxy is cured at a temperature higher than room temperature (e.g. 25° C.). In one example the epoxy is cured at approximately 50° C. In one example the epoxy is cured at approximately 85° C. In one example the epoxy is cured at room temperature. In one example, more than one time and temperature are used to cure the epoxy. In one example components are held in a mold for a period of time at a first temperature before a second heating phase that is used to complete the cure process. One example method includes heating in a mold at approximately 50° C. for a period of time, then heating the mold to approximately 85° C. to complete the cure process. In one example the method includes holding the mold at approximately 50° C. for approximately 40 minutes, then heating the mold to approximately 85° C., and holding at 85° C. for approximately 10 minutes to complete the cure process. In one example, the first cure step includes placing the mold in an oven at approximately 50° C., and turning off the oven, allowing the mold to slowly cool from approximately 50° C. to a lower temperature at the end of 40 minutes. This slow cooling process during cure can provide enhanced material properties such as a low concentration of air bubbles in the epoxy, and a high fracture toughness.

Figure 2:
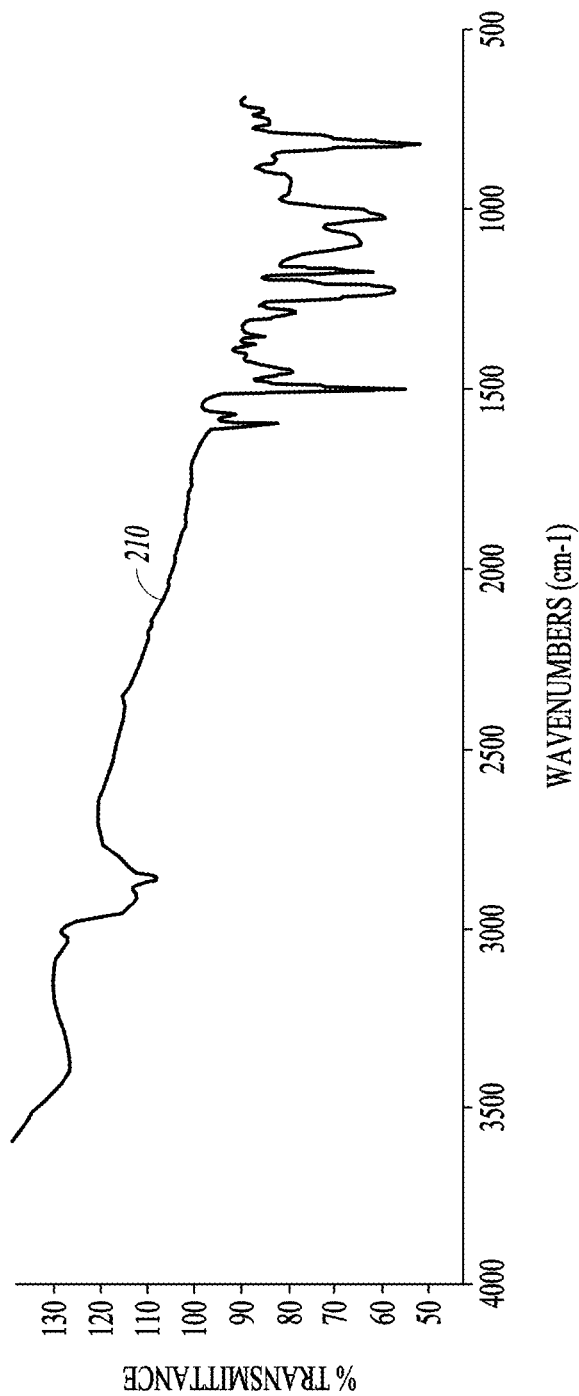
FIG. 2 shows an FTIR spectra of an example polymer header according to an embodiment of the invention.

FIG. 2 shows a Fourier Transform Infrared spectroscopy (FTIR) spectra 210 of an epoxy used in forming the header 110. In one example, the epoxy characterized by spectra 210 includes a number of desirable properties, such as high modulus, high fracture toughness, high hardness, and high failure strength. In one example, the cured epoxy includes a Shore D hardness between 75 and 90. In one example, the cured epoxy includes a tensile strength of approximately 55 MPa. In one example, the cured epoxy includes a glass transition temperature of approximately 70° C. The epoxy characterized by spectra 210 is also substantially transparent. A transparent header 110 can be useful because components such as contacts 112 can be visually inspected during manufacture and use of the IMD 100. In one example, the epoxy includes M-31CL provided by LOC-TITE®. M-31CL is typically used as an adhesive, and is not commonly used for molding structural components.

Figures 3A, 3B:
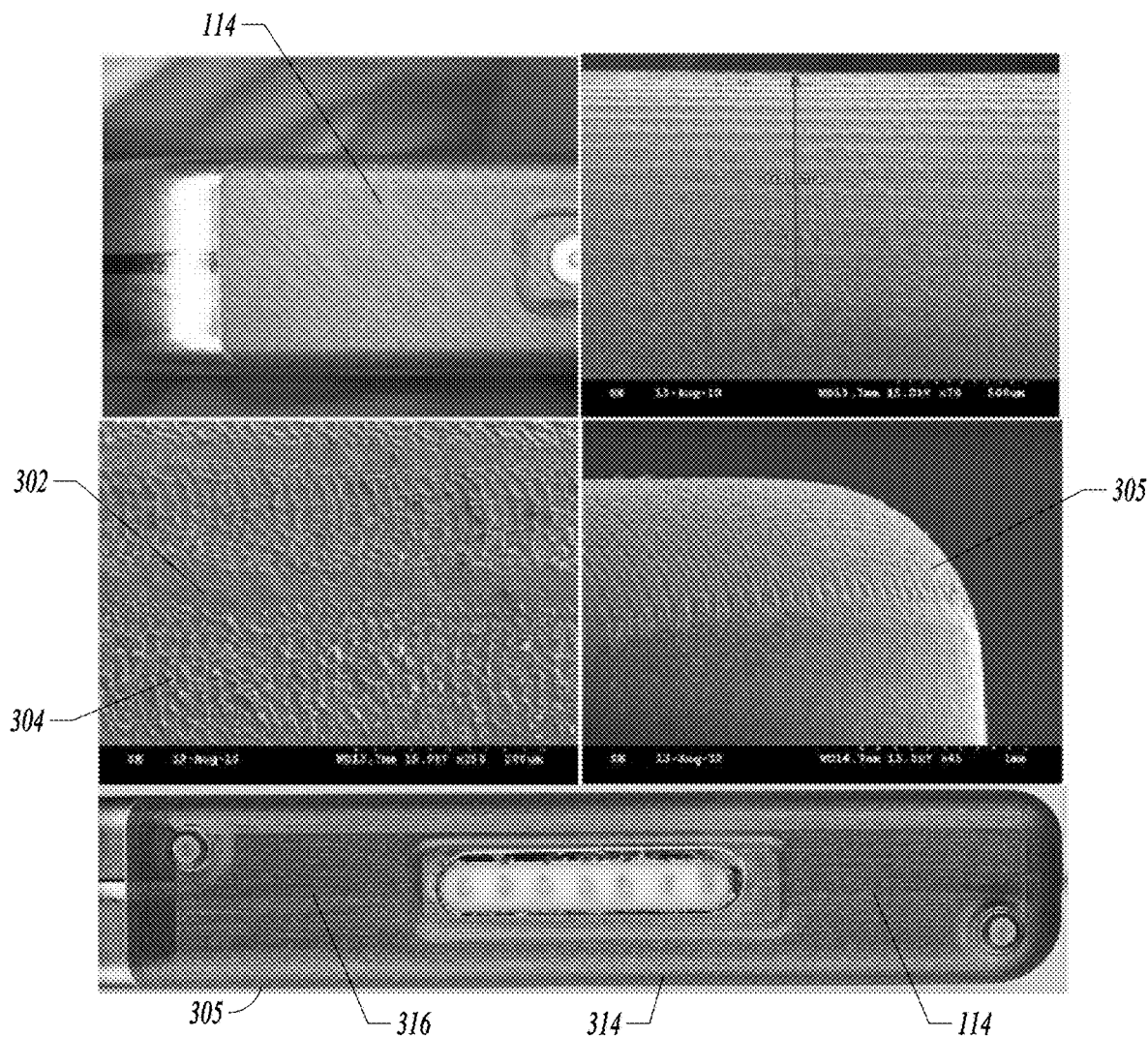
FIG. 3A shows five images of a device according to embodiments of the invention.
FIG. 3B shows a surface roughness calculation according to an embodiment of the invention.

FIG. 3A illustrates an embodiment of the surface 114 of the metallic device container 102, including a textured surface. In one example, a surface roughness of the surface 114 is characterized by optical profilometry techniques. White light interference patterns are analyzed to yield a number of roughness figures of merit, including surface average ($S_a$); surface root-mean-square ($S_q$); surface maximum ($S_{max}$); surface minimum ($S_{min}$); range ($S_y$); and a surface area scanned (S3A). FIG. 3B shows an example output of a surface roughness scan of a textured surface 114.

In one example surface 120 includes an $S_q$ between 3.05 micrometers (μm) and 10.2 μm. In one example surface 114 includes an $S_q$ between 3.81 μm and 8.89 μm. In one example surface 114 includes an $S_q$ between 3.30 μm and 3.81 μm. Texturing the surface 114 prior to attachment or overmolding of the header 110 increases strength of the interface between the header 110 and the metallic device container 102.

FIG. 3A shows a periodic pattern including a first linear feature 302 and a second linear feature 304. The additional texture of features 302, 304 can enhance adhesion at an interface between the surface 114 of the metallic device container 102 and the header 110. In one example, the surface 114 of the metallic device container 102 is textured around a curved surface 305 at edges of the metallic device container 102. In one example, a high quality texture is provided on curved surfaces 305 of the metallic device container 102 by rotating the metallic device container 102 during surface processing to best expose the curved surface 305 to the processing media, such as blast particles, laser energy, etc. In another example, the metallic device container 102 stays fixed, and the processing media source (blast particles, laser energy, etc.) rotates around an incident angle to provide a substantially tangent incident angle to the curved surfaces 305.

Figure 3C:
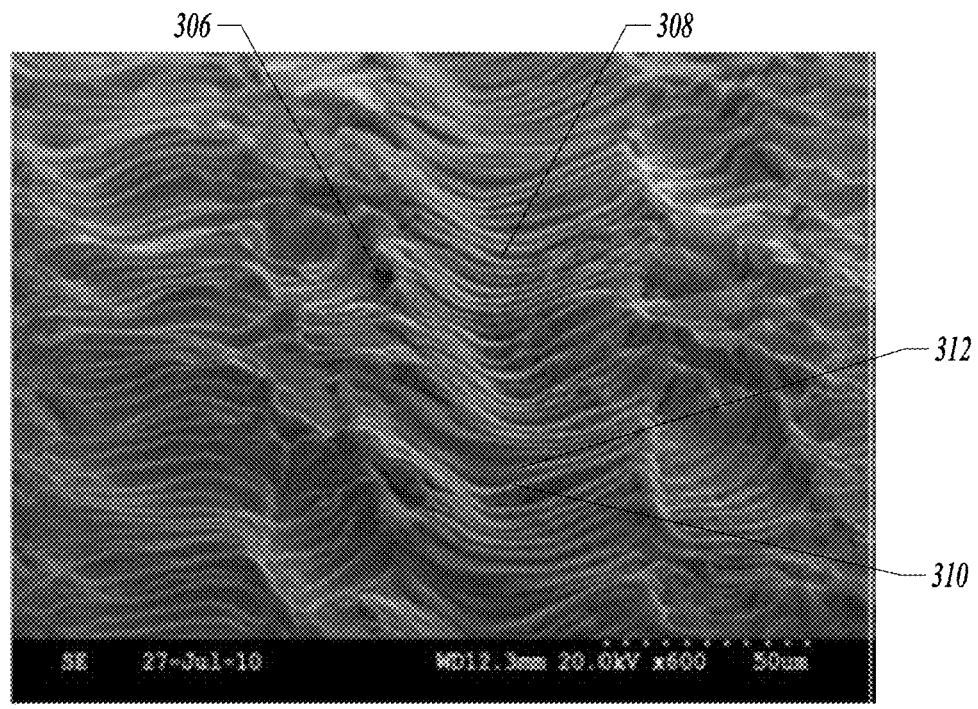
FIG. 3C shows a photo micrograph of a device according to an embodiment of the invention.

FIG. 3C shows another example of a textured surface formed according to an example process. FIG. 3C illustrates another example texture that exhibits one or more periodic patterns. A ridge 306 and a trough 308 are illustrated in the figure. In selected embodiments, more than one periodic pattern is included in a single textured surface. For example, a second periodic pattern is included in FIG. 3C, with a ridge 310 and a trough 312.

Figure 3D:
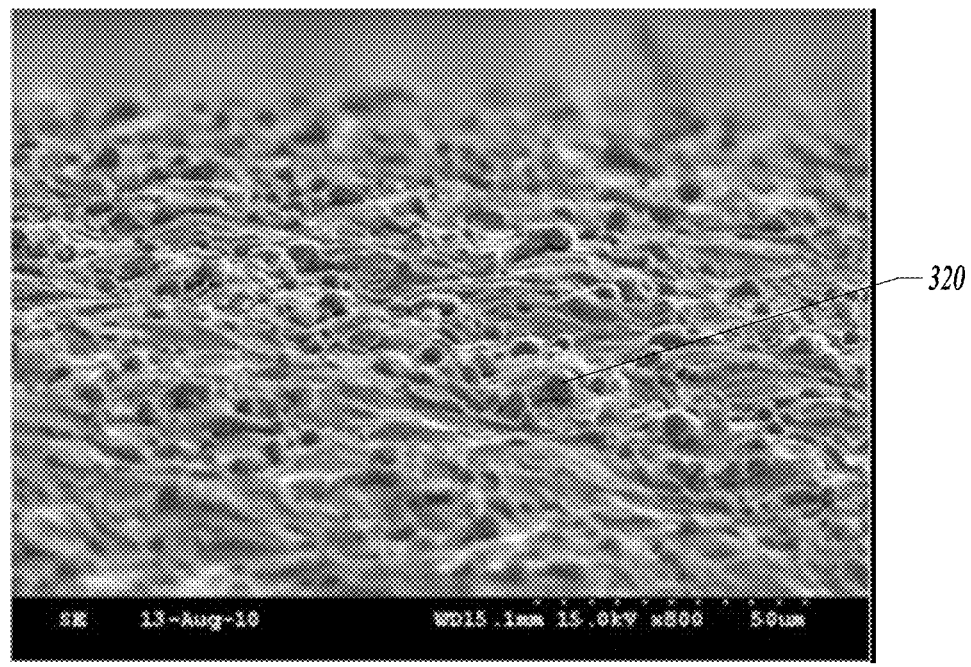
FIG. 3D shows a photo micrograph of a device according to an embodiment of the invention.

FIG. 3D shows another example of a textured surface formed according to an example process. In FIG. 3D, a number of particles 320 are formed, and adhered to the surface of the metal. The particles 320 can be useful in later adhesion of an epoxy, or other thermoset header for a number of reasons, including an undercut portion, where the particle 320 adheres to the metal surface, due to a substantially spherical shape of selected particles 320, adhering at tangent points of spheres. In one example the textured surface as shown in FIG. 3D is formed by laser treatment.

The surface 114 can be textured in a variety of methods. For example, the surface 114 can be textured by dry surface blasting with particles such as aluminum oxide particles, laser treating the surface 114, or chemical etching the surface 114. In one embodiment, one or more of these texturing processes are used to texture the surface 114. Although a number of example texturing methods are listed, other methods that produce a surface roughness in the desirable ranges are also considered within the scope of the present disclosure.

In one example, the surface 114 is textured in a periodic pattern. In one example, the periodic pattern includes a linear (e.g. hatched) pattern of ridges 304 and troughs 302 as shown in FIG. 3A. In one example, a scanned laser treatment provides the linear textured pattern. In some examples, the surface 114 is textured in a multidirectional pattern. In further examples, the multidirectional pattern includes a first pattern 314 and a second pattern 316. In some examples, one or more of the patterns of the multidirectional pattern are etched. In some examples, the first pattern 314 is disposed around a periphery of the surface 114 of the metallic device container 102. In some examples, the first pattern 314 includes a pattern of ridges running substantially along the periphery of the surface 114. In some examples, the first pattern 314 is disposed at least partially along the curved surface 305 of the metallic device container 102. The second pattern 316, in some examples, includes a pattern of ridges disposed on the surface 114 of the metallic device container 102 within the first pattern 314, wherein the first pattern 314 forms a border around the second pattern 316. Although the multidirectional pattern of FIG. 3A shows only the first and second patterns 314, 316, it is contemplated that, in further examples, the multidirectional pattern can include more than two patterns. In other examples, the multidirectional pattern can include portions of differing intensity, including, but not limited to, higher or lower ridges, more or fewer ridges or other pattern features per unit of area of the surface, more or less defined ridges or other pattern features, or a combination of these examples. It is noted that, in some examples, the multidirectional pattern can include lines or ridges that are substantially straight, wavy, or otherwise varied along its length or can include a pattern feature other than lines, such as dimples, bumps, or the like. Such examples of multidirectional patterns can limit, reduce, or otherwise inhibit stress concentrations or defect propagation of an overmolded header. For instance, in the multidirectional pattern of FIG. 3A, the first pattern 314 including ridges that run around the periphery of the surface 114 provides a boundary that can moderate a stress concentration from a deflection force crossing the boundary.

Figure 4:
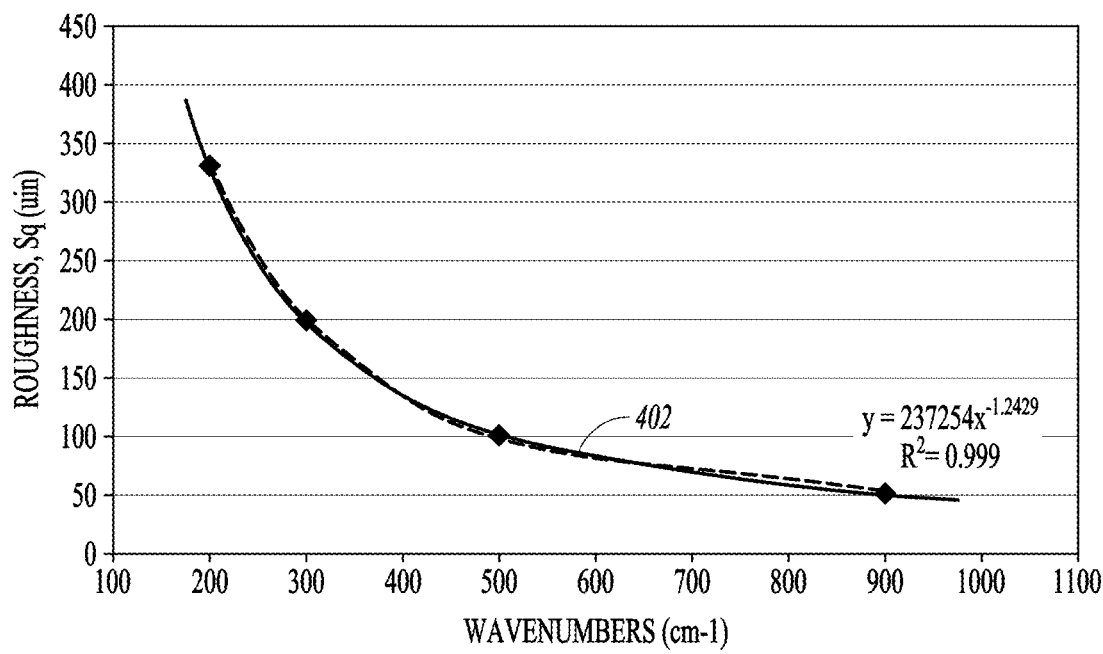
FIG. 4 shows graph of laser speed versus surface roughness according to an embodiment of the invention.

FIG. 4 shows a graph with a plot 402 of laser scan speed versus a resulting $S_q$ value for the surface 114. The plot 402 of FIG. 4 is provided using a 0.1 millimeter (mm) offset between scans of the laser, and a 0.068 mm diameter laser spot size.

Figure 5:
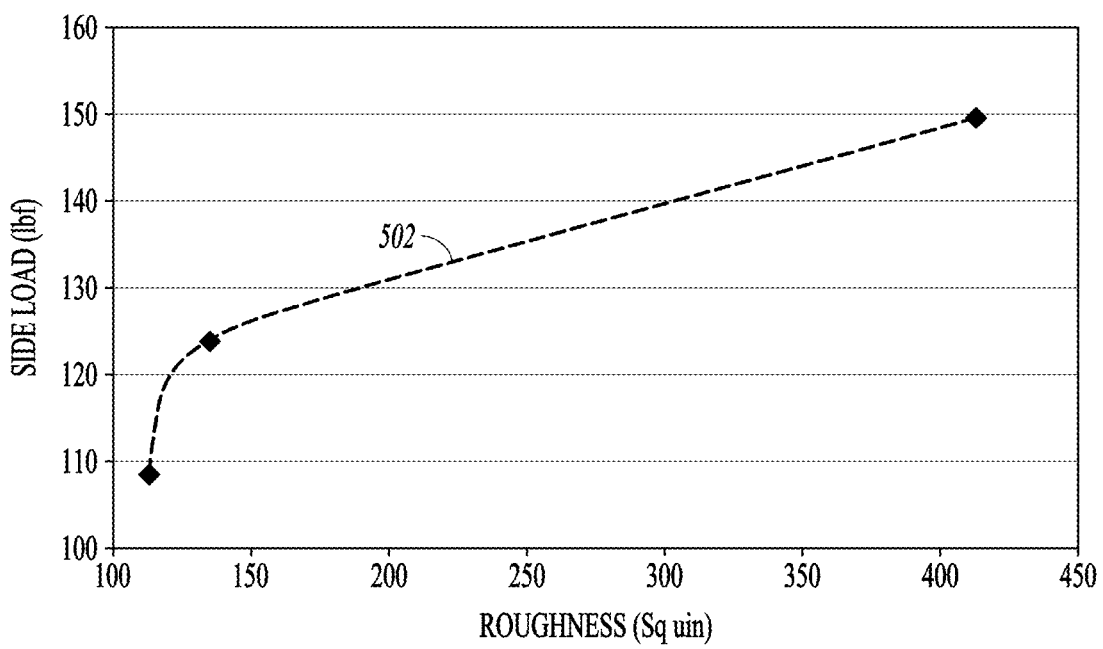
FIG. 5 shows graph of surface roughness versus failure strength of a device according to an embodiment of the invention.

FIG. 5 shows a graph of side load failure strength versus $S_q$. A plot 502 shows that side load strength increases with increasing values of $S_q$, with a high rate of change in strength achieved at $S_q$ values between 120 and 150.

Figure 6A:
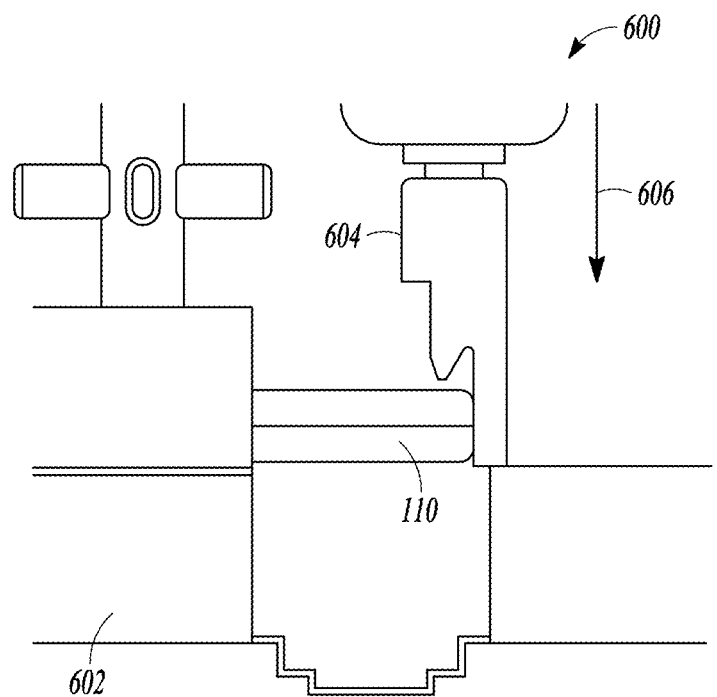
FIG. 6A shows an example side load testing apparatus according to an embodiment of the invention.
Figure 6B:
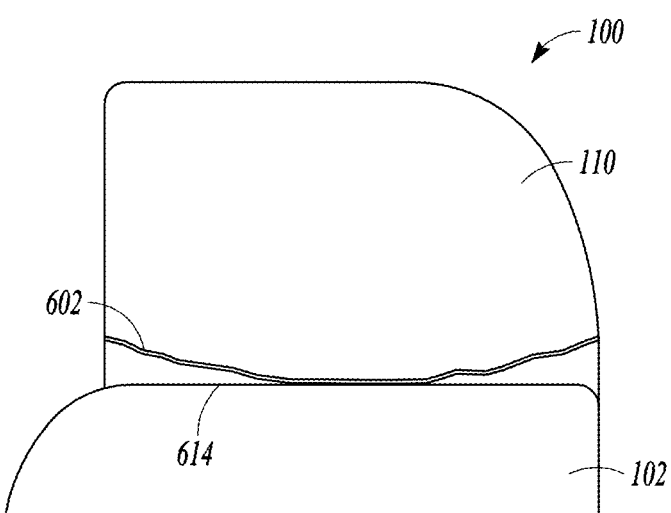
FIG. 6B shows a test specimen according to an embodiment of the invention.

FIG. 6A shows a testing device 600 for measuring side load failure strength. A clamp 602 is used to secure the metallic device container 102, while the header 110 is pressed using a ram 604 along direction 606. FIG. 6B shows an example of an IMD 100 after failure testing in device 600. The header 110 is shown with a fracture 602. In the example shown, the fracture 602 is in the header 110 itself, rather than at the surface 614 of the metallic device container 102, indicating that the bond strength between the header 110 and the metallic device container 102 was higher than the strength of the header 110 in the bulk.

As discussed herein, failure mode in either the bulk, as shown in FIG. 6B, or at an interface between the header 110 and the surface 114, can be dependent on geometry of the metallic device container 102. For example, in extremely thin metallic device containers 102, the failure mode may change from the bulk of the header 110, to the interface between the header 110 and the surface 114.

In contrast, in some embodiments when the metallic device container 102 has a thickness between approximately 16 mm and 4 mm, a header 110 can fail in the bulk before failure at the interface between the header 110 and the surface 114. In another embodiment, a header 110 can fail in the bulk before failure at the interface between the header 110 and the surface 114 for configurations of metallic device container 102 with thicknesses between approximately 14 mm and 6 mm. Additionally, a header 110 can fail in the bulk before failure at the interface between the header 110 and the surface 114 for configurations of metallic device container 102 with thicknesses between approximately 12 mm and 8 mm.

Figure 7:
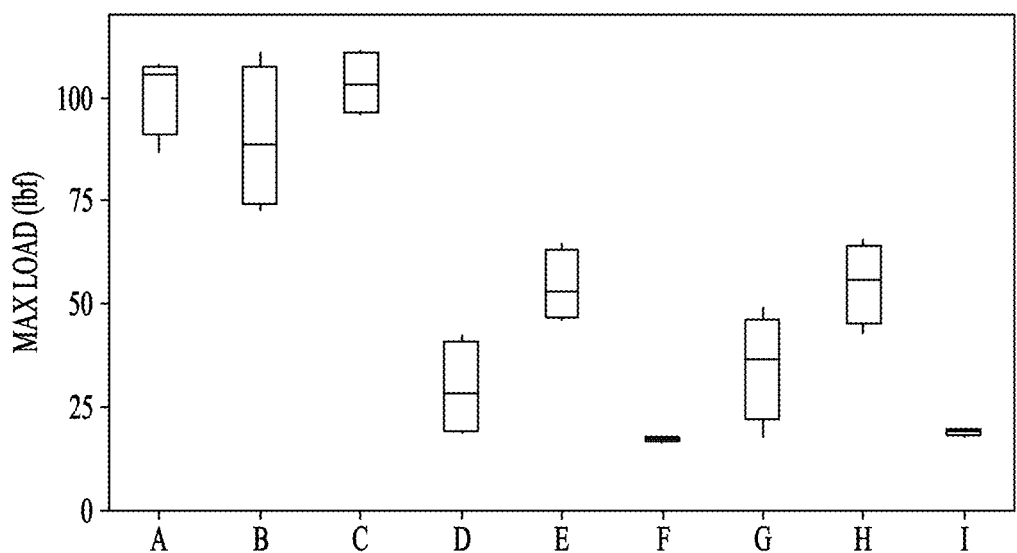
FIG. 7 shows a graph of failure strength in side load testing for various devices according to an embodiment of the invention.

FIG. 7 shows a graph of side load failure strength testing for a number of header materials. Test specimens A, B, and C include $S_q$ values between 120 and 150, with resulting side load failure strength between approximately 0.334 kilonewtons (KN) and 0.489 KN. Test specimens A, B, and C include headers 110 formed from the epoxy characterized by the FTIR spectra 210 in FIG. 2. Test specimens D, E, F, G, and H include different epoxy compositions. As can be seen from the graph in FIG. 7, the choice of epoxy and surface roughness combine to produce an IMD 100 with higher side load failure strength ($S_q$) than other epoxy materials.

Referring to FIGS. 8-12, an example IMD 800 is shown. In some examples, the IMD 800 includes a device container 802. The IMD 800, in some examples, includes a header 810 attached to the device container 802. The header 810, in different examples, can be attached to the device container 802 in various ways, including molding the header 810 to the device container 802, for instance, as described herein. In some examples, the header 810 can be formed from one or more of the materials described herein. In some examples, an adhesive can be used to attach the header 810 to the device container 802, as described herein. In some examples, the device container 802 can include a textured surface for attachment of the header 810 to the device container 802, as described herein.

The header 810, in various examples, includes one or more electronic connection features, such as, for instance, one or more bore holes 812. In the example shown, the header 810 includes three different types of bore holes 812A, 812B, 812C. The one or more bore holes 812, in some examples, can be used to couple to additional components, such as leads. In some examples, each of the one or more bore holes 812 includes one or more electrical contacts 814 configured to electrically couple to one or more leads or other components inserted within the bore hole 812. In various examples, the one or more electrical contacts 814 are electrically coupled to one or more of the one or more electronic modules within the device container 802. For instance, in some examples, the electrical contact 814 is coupled to a wire 806 disposed between the electrical contact 814 and the one or more electronic modules. In an example, the wire 806 passes through a feedthrough 804 of the device container 802 that is configured to allow one of more wires 806 to pass into the device container 802 while maintaining a sealed environment within the device container 802.

The header 810, in some examples, includes a header core 820 and a header shell 840 disposed around the header core 820. In further examples, the header shell 840 is attached to the device container 802. In some examples, the header core 820 is formed separately from the header shell 840 and/or the device container 802. In some examples, the header core 820 and the header shell 840 are separately molded. In further examples, the header core 820 is molded and electrically coupled to the device container 802, and, thereafter, the header shell 840 is molded around the header core 820 and the device container 802. In some examples, molding the header shell 840 around the header core 820 and the device container 802 affixes the header shell 840 directly to the device container 802, as described herein, and acts to retain the header core 820 with respect to the device container 802. In some examples, the header core 820 is formed from a first material and the header shell 840 is formed from a second material, the first material being different from the second material. In an example, the first material or the second material includes a polymer material. A polymer can provide a number of desirable features, such as biocompatibility, strength, resilience, and ease of manufacturing. In some examples, the first material includes a thermoplastic material. In further examples, the first material includes one or more of polysulfone, polycarbonate, and/or polyurethane. In still further examples, the first material includes one or more of Isoplast and/or Tecothane. In some examples, the first material includes a thermoset material, such as, for instance, polyurethane. In some examples, the second material includes epoxy.

Forming the header core 820 separately from the header shell 840 and/or device container 802 is advantageous for many reasons including, but not limited to: verifying bore hole geometry and orientation with respect to the header core 820 and/or, ultimately, the device container 802; verifying location of the one or more electrical contacts 814; and providing for routing control of the one or more wires 806. Additionally, in some examples, separately forming the header core 820 can reduce losses in the event of a defect or other impropriety in the header core 820. For instance, if a defect is discovered in a header core, then that header core can be discarded prior to attachment with the device container, the loss of which, in at least some circumstances, is considerably less than the loss if an entire IMD had to be discarded due to the discovery of a defect with the header.

In some examples, the header 810 includes an identification tag 818, which, for instance, can include information relevant to the identification of the IMD 800 and/or the patient within which the IMD 800 is implanted. In some examples, the identification tag 818 is visible in one or more imaging modalities, such as, for instance, x-ray, ultrasound, computed tomography, magnetic resonance imaging, or the like. In an example, the identification tag 818 is configured to be x-ray readable. In an example, the identification tag includes tungsten. In some examples, the identification tag 818 can include a radio frequency identification tag or can otherwise include information accessible using radio frequency interrogation.

Referring now to FIGS. 8, 9, and 11-13, the identification tag 818, in various examples, is engaged or retained within a tag holder 822 of the header core 820. The tag holder 822 can include an opening 824 sized and shaped to retain at least a portion of the identification tag 822 within the opening 824. In an example, the tag holder 822 is configured to maintain the identification tag 818 in a specified position and location with respect to the IMD 800 to facilitate finding and reading the identification tag 818, for instance, using an imaging device. In some examples, the tag holder 822 maintains the location of the identification tag 818 during molding of the header shell 840 over the header core 820.

In some examples, the opening 824 is a slot 824A sized to accept the identification tag 818 and frictionally retain the identification tag 818 within the slot 824A. In further examples, the opening 824 includes a second portion 824B (FIGS. 11 and 13) in addition to the slot 824A, the second portion 824B being configured to facilitate overmolding of the header shell 840. That is, the second portion 824B allows material to enter the opening 824 during overmolding of the header shell 840, for instance, to get within one or more cutouts 818A in the identification tag 818 disposed within the opening 824 and limit void spaces (i.e., areas unfilled by mold material during overmolding of the header shell 840) within the header shell 840 at the location of the one or more cutouts 818A. Such void spaces can lead to various molding problems or defects, such as, for instance, delamination (i.e., separation) of the header shell 840 with respect to the header core 820 and/or the device container 802. In some examples, the second portion 824B is a second slot that extends substantially perpendicular to the slot 824A to form a generally plus-shaped opening 824 when viewed from an end. In other examples, different opening shapes are contemplated, such as, for instance, a single slot shape (for instance, just the slot 824A), an opening including one or both side walls being generally rounded (a substantially elliptical opening, for instance), an opening including one or both side walls being at least partially bowed-out, a T-shaped opening, or the like.

Figure 14:
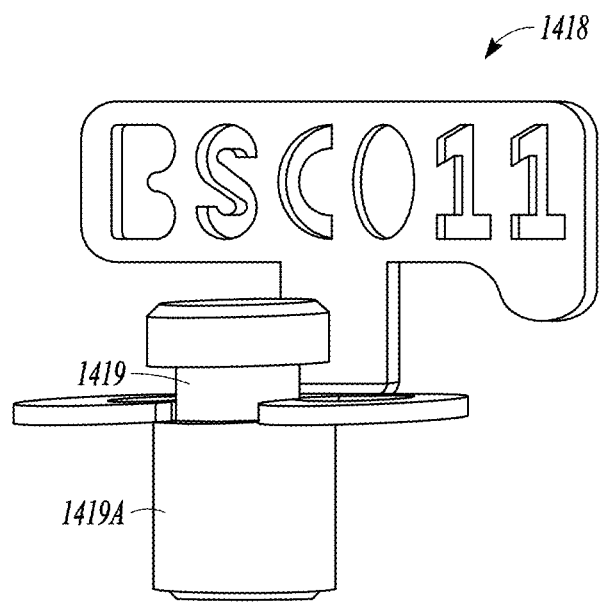
FIG. 14 shows an example identification tag of an IMD according to an embodiment of the invention.

Referring to FIG. 14, in other examples, an identification tag 1418 can include a base 1419 configured to be retained by a header core. In an example, the base 1419 includes a post 1419A extending from the base 1419, the post 1419A configured to be engaged with or otherwise retained by a tag holder (for instance, within a corresponding opening) of the header core. In a further example, the post 1419A frictionally fits within the opening to retain the identification tag 1418 in a desired position during overmolding of a header shell. In further examples, the post 1419A can include an indexing feature configured to position and maintain the identification tag 1418 in a selected orientation with respect to the header core. In some examples, the indexing feature includes a shape to inhibit the post 1419A from rotating or otherwise being inserted improperly within the opening. For instance, the post 1419A can include a generally cylindrical shaft with a flat surface or a key to correspond to a similar, complementary feature of the opening. In other examples, the post 1419A can include an asymmetric shape or another shape capable of being inserted and retained within a complementary opening in a particular orientation.

In some examples, instead of or in addition to using an identification tag similar to the example identification tags 818, 1418 described herein, an identification tag can be printed on a portion of an IMD. In some examples, the identification tag can be printed on a surface of a header core. In other examples, the identification tag can be printed on another portion of the IMD, such as, for instance, a surface of a device container and/or a component within the device container, such as a battery. In some examples, the identification tag can be printed using a material that is capable of being imaged using an imaging technique. For instance, in an example, the identification tag can be printed on a portion of the IMD using an ink or other material that is x-ray opaque or otherwise visible using x-ray imaging, such that, when the IMD is x-ray imaged, the identification tag can be seen in the x-ray image. In other examples, the printed identification tag can be configured to be visible using other imaging techniques in addition to or instead of using x-ray imaging. In some examples, the identification tag is pad printed and/or tampoprinted onto a portion of the IMD.

Referring now to FIGS. 8-10 and 12, in some examples, the header core 820 includes an antenna attachment feature 826 configured to locate, support, and/or position an antenna 808 with respect to the header core 820 and, in turn, the IMD 800 and the patient within which the IMD 800 is ultimately implanted. In some examples, the antenna attachment feature 826 is configured to maintain a substantially constant distance between the antenna 808 and the patient. In the example shown in the presently-referenced figures, the antenna 808 is a substantially spiral-shaped antenna 808, and the antenna attachment feature 826 is shaped to accommodate such an antenna. In other examples, the antenna attachment feature can be differently shaped, sized, and/or configured to accommodate differently-shaped antennas.

The antenna 808, in some examples, is engaged with the antenna attachment feature 826 and is electrically coupled with the electronic module within the device container 802. In some examples, a wire 806 is attached to the antenna 808 and is disposed between the antenna 808 and the electronic module within the device container 802 to electrically couple the antenna with the electronic module. In other examples, the antenna can be directly electrically coupled to the electronic module and can extend from the electronic module within the device container 802 to the antenna attachment feature 826.

Figure 8:
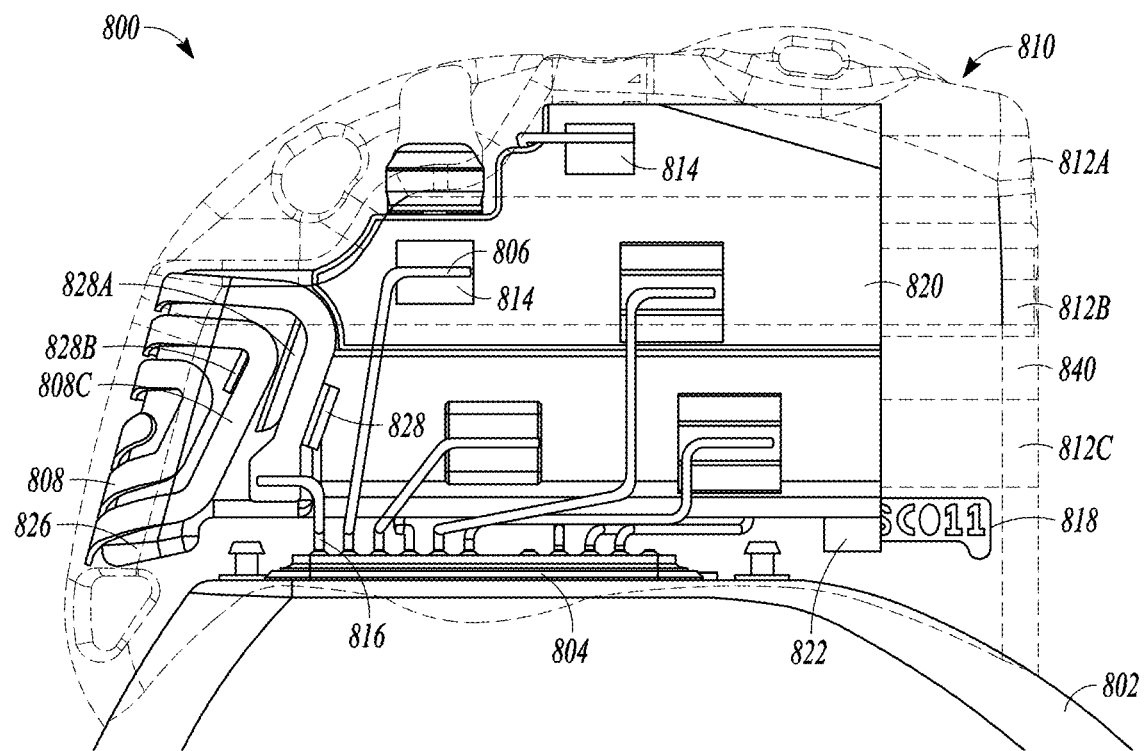
FIG. 8 shows a side view of an example header of an IMD according to an embodiment of the invention.
Figure 9:
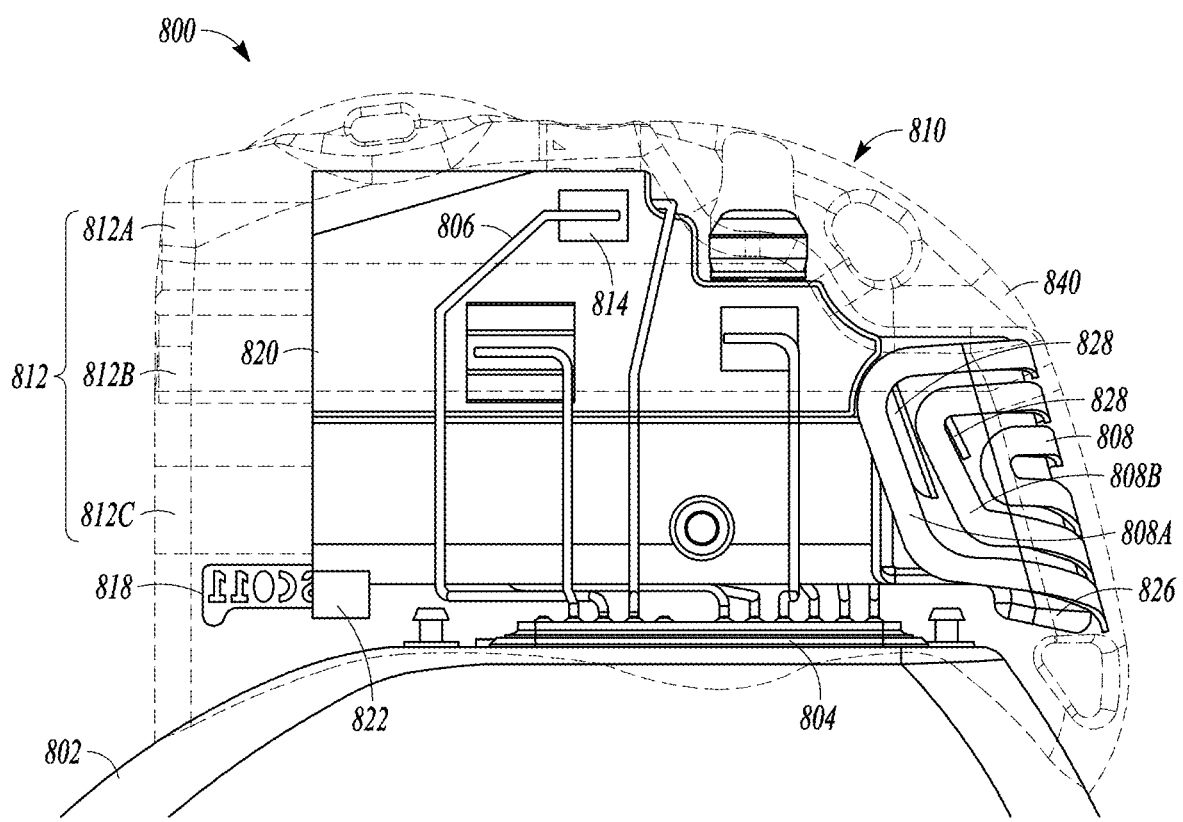
FIG. 9 shows a side view of an example header of an IMD according to an embodiment of the invention.
Figure 10:
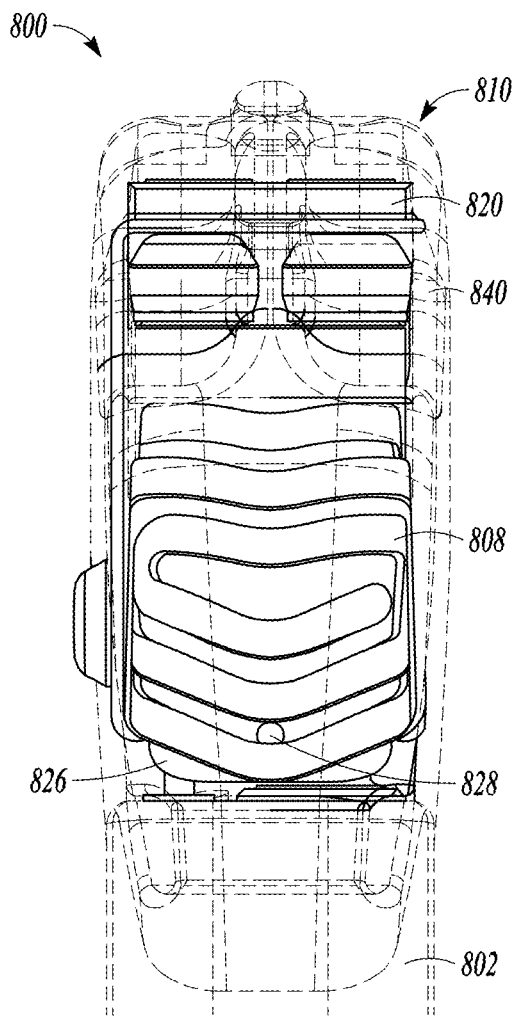
FIG. 10 shows a front view of an example header of an IMD according to an embodiment of the invention.
Figure 11:
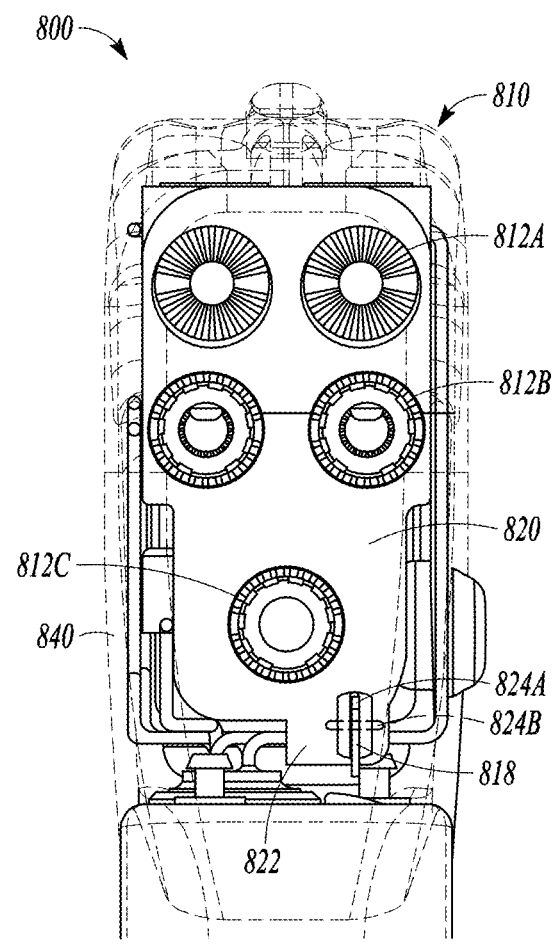
FIG. 11 shows a back view of an example header of an IMD according to an embodiment of the invention.
Figure 12:
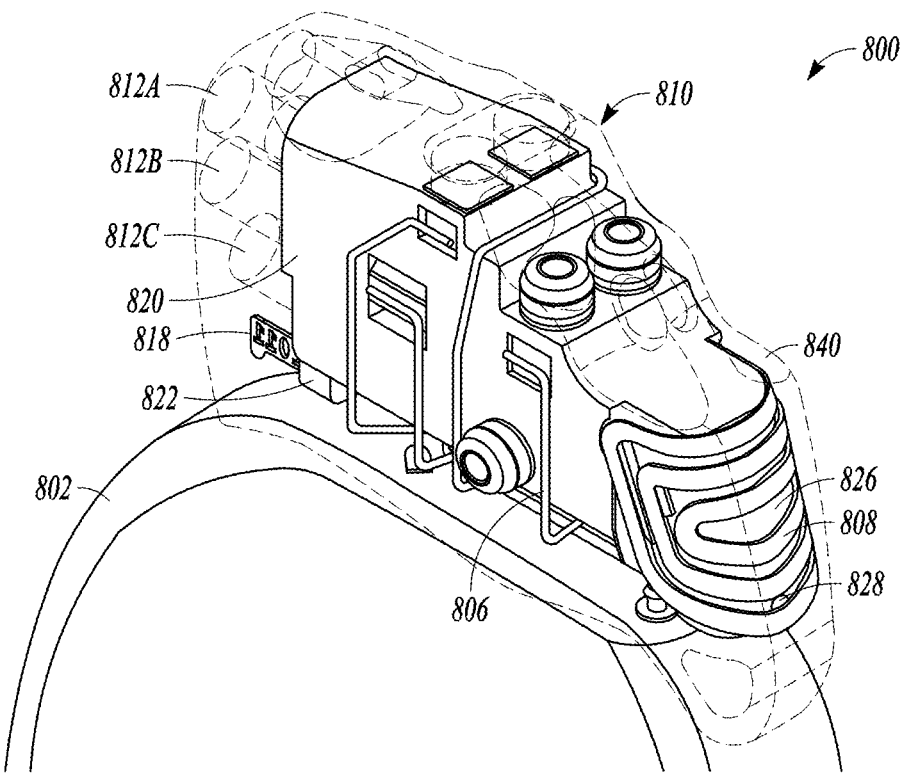
FIG. 12 shows a perspective view of an example header of an IMD according to an embodiment of the invention.
Figure 13:
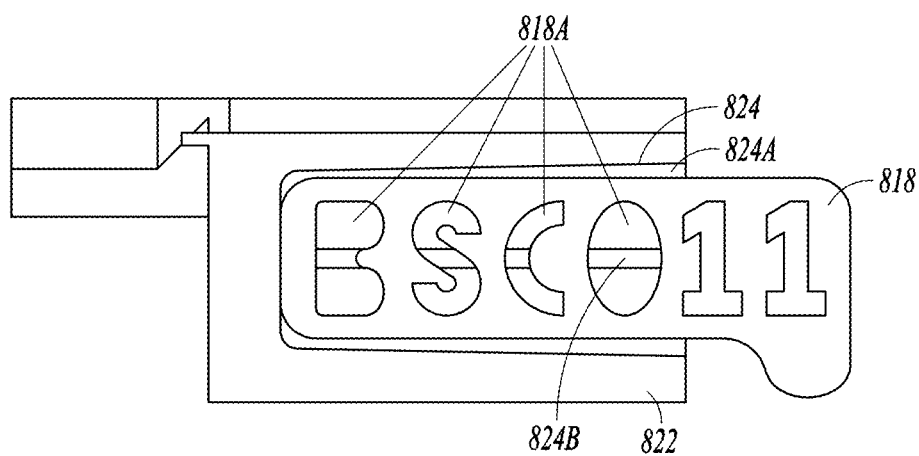
FIG. 13 shows an example identification tag of an IMD according to an embodiment of the invention.

In some examples, the antenna attachment feature 826 is configured to locate the antenna 808 in a selected position with respect to the header core 820. The selected position, in various examples, allows for the antenna 808 to receive and/or send communication signals. In this way, the IMD 800 can be communicatively coupled with one or more devices located either within or outside the patient. In the example shown in the presently-referenced figures, the antenna 808 is disposed at a first surface of the header core 820 (the left side surface of the header core 820, as shown in FIG. 8) and wraps around to adjacent surfaces of the header core 820. The header shell 840, in some examples, is disposed around the header core 820 and is attached to the device container, as described herein. In further examples, the header shell 840 is also disposed around the antenna 808, such that the header shell 840 acts to at least partially retain the antenna 808 in the selected position within the header shell 840.

The antenna attachment feature 826, in some examples, includes an abutment feature, such as a protrusion or a ridge 828, configured to retain the antenna 808 with respect to the antenna attachment feature 826. In some examples, the abutment feature can include one or more pins, posts, or the like. In some examples, the ridge 828 is sized and positioned on the antenna attachment feature 826 to abut the antenna 808 and support the antenna 808 in the selected position with respect to the header core 820. In some examples, the antenna 808 rests on the ridge 828. In some examples, the ridge 828 positively engages the antenna 808, for instance, with a retention feature configured to grip at least a portion of the antenna 808. Examples of such a retention feature include a lip, protrusion, or other structure extending from the ridge 828 to form a slot within which a portion of the antenna 808 can be retained. In further examples, the retention feature is configured to frictionally retain at least the portion of the antenna 808. The ridge 828, in various examples, is sized and shaped to fit between portions 808A, 808B (FIG. 9) of the antenna 808. In an example, the portions 808A, 808B of the antenna 808 are configured to frictionally engage the ridge 828.

In some examples, the antenna attachment feature 826 includes more than one ridge 828. The ridges 828, in some examples, are spaced and located to accommodate the antenna 808 between the ridges 828. For instance, a portion 808C of the antenna 808 is shown in FIG. 8 disposed between two ridges 828A, 828B. In a further example, the ridges 828A, 828B are spaced to provide a frictional engagement with the portion 808A of the antenna 808. In an example, the one or more of the ridges 828 of the antenna attachment feature 826 are disposed between portions 808A, 808B of the antenna 808 and are configured to maintain spacing between the portions 808A, 808B of the antenna 808. In further examples, the one or more ridges 828 are configured to maintain spacing between the antenna 808 and other components, such as, for instance, wires 806, electrical contacts 814, the device container 802, or the like. In this way, the one or more ridges 828 act to inhibit shorts between the antenna 808 and other components of the IMD 800.

In some examples, the ridges 828 are disposed on multiple sides of the antenna attachment feature 826. For instance, in the example shown in the referenced figures, the antenna 808 wraps around three sides of the antenna attachment feature 826, with one or more ridges 828 on each of the three sides of the antenna attachment feature 826 to support the various sides of the antenna 808 wrapping around the antenna attachment feature 826. In other examples, the antenna attachment feature 826 includes different shapes and configurations of ridges or other protrusions to accommodate and support differently sized and/or shaped antennas. In various examples, the antenna attachment feature 826 is configured to inhibit mold defects during overmolding of the header shell 840. For instance, one or more various aspects of the antenna attachment feature 826 are shaped and configured to allow the mold material to flow around the one or more aspects of the antenna attachment feature 826 during the overmolding of the header shell 840 with little to no turbulence, collection of bubbles, formation of void spaces, or other defects which could give rise to problems with the molded header shell 840, such as, for instance, delamination from the header core 820.

Figure 15:
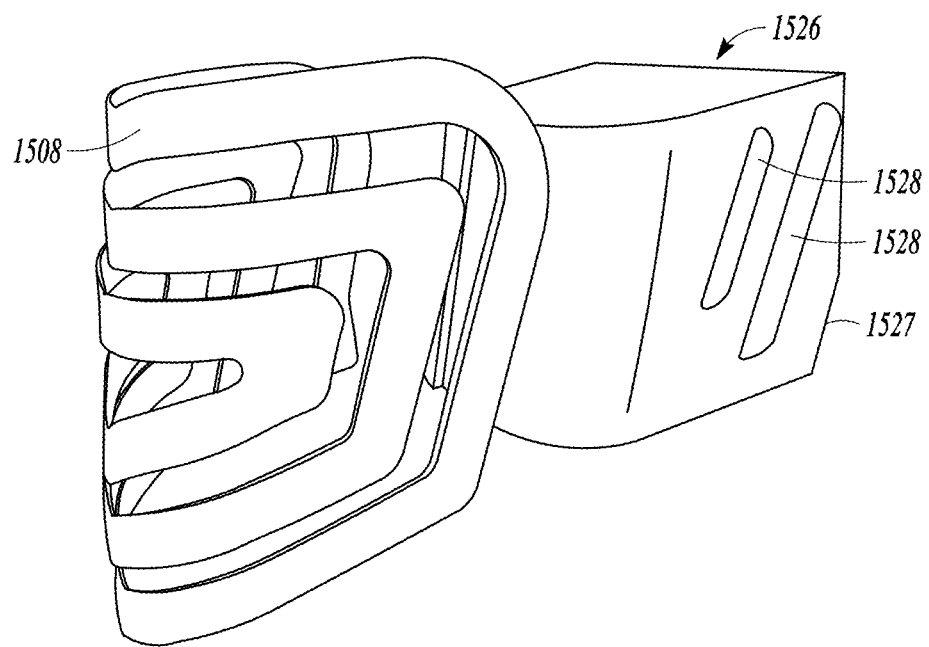
FIG. 15 shows an example antenna and antenna support of an IMD according to an embodiment of the invention.

Referring to FIG. 15, in some examples, an antenna attachment feature 1526 can include an antenna attachment portion 1527 configured to detachably engage with a header core. The antenna attachment portion 1527 can be detachably engaged to the header core in various ways, including complementary engagement features disposed on the antenna attachment portion 1527 and the header core, like a tab-and-slot configuration or a pin-and-hole configuration, for instance. In further examples, the header core and the antenna attachment portion 1527 can include mating snap-together features or mating slide-together features. In still further examples, adhesive can be used to engage the antenna attachment portion 1527 with the header core.

The antenna attachment feature 1526, in various examples, includes one or more abutment features, such as protrusions, pins, posts, and/or ridges 1528 configured to retain an antenna 1508 with respect to the antenna attachment feature 1526. In some examples, the one or more ridges 1528 are similar to the ridges 828 described herein. In various examples, the antenna attachment feature 1526 is configured to inhibit mold defects during overmolding of the header shell. For instance, one or more various aspects of the antenna attachment feature 1526 are shaped and configured to allow the mold material to flow around the one or more aspects of the antenna attachment feature 1526 during the overmolding of the header shell with little to no turbulence, collection of bubbles, formation of void spaces, or other defects which could give rise to problems with the molded header shell, such as, for instance, delamination from the header core.

Figure 16:
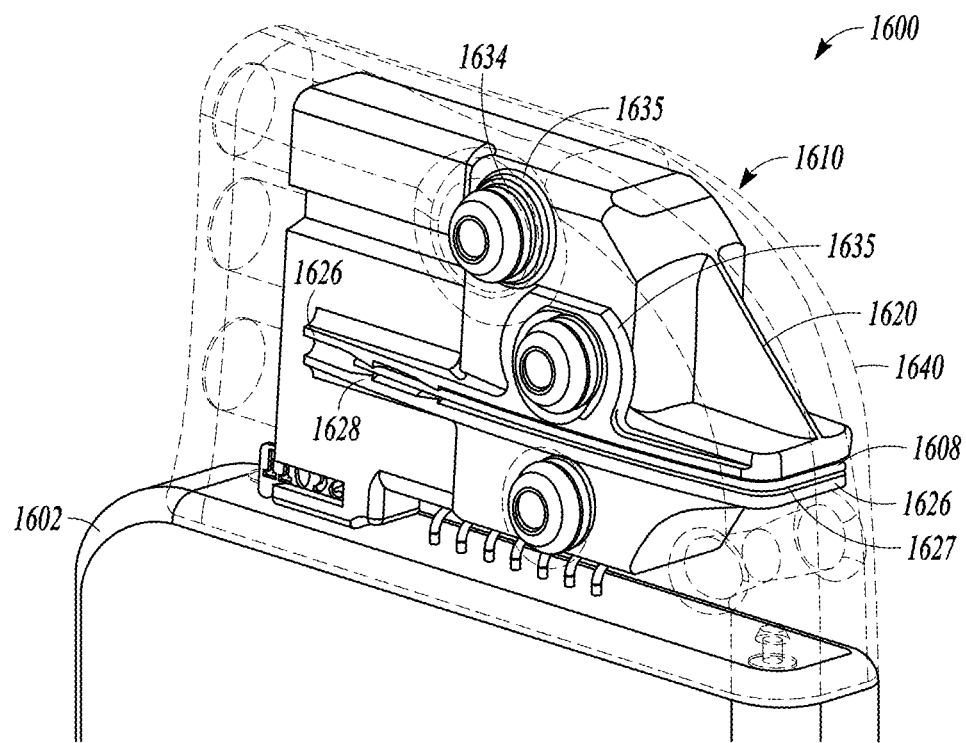
FIG. 16 shows an example header of an IMD according to an embodiment of the invention.

Referring to FIG. 16, in some examples, an IMD 1600 includes a header 1610 attached to a device container 1602, the header 1610 including a header shell 1640 disposed around a header core 1620. In some examples, the header core 1620 includes an antenna attachment feature 1626 configured to locate and/or support an antenna 1608 in a selected position with respect to the header core 1620. In the example shown in the presently-referenced figure, the antenna 1608 is a wire member that extends from the device container 1602, extends along one side of the header core 1620, wraps around a front of the header core 1620, and extends along the other side of the header core 1620. In further examples, the header shell 1640 is also disposed around the antenna 1608, such that the header shell 1640 acts to at least partially retain the antenna 1608 in the selected position within the header shell 1640.

In some examples, the antenna attachment feature 1626 includes a channel 1627 sized to accept the antenna 1608 within the channel 1627. In some examples, the channel 1627 can extend along one or more sides of the header core 1620, depending on the desired configuration, position, and/or location of the antenna 1608 with respect to the header core 1620. In further examples, the channel 1627 can extend continuously or can be broken into segments on one or more sides of the header core 1620. The antenna attachment feature 1626, in some examples, is integrally formed in the header core 1620. For instance, the antenna attachment feature 1626 can be molded and/or machined into the header core 1620. In further examples, the antenna attachment feature 1626 can be affixed to the header core 1620 using an adhesive, for instance. In still further examples, the antenna attachment feature 1626 can be engaged with the header core 1620 using complementary engagement features or the like.

The antenna attachment feature 1626, in some examples, includes one or more retention features 1628 configured to retain the antenna 1608 within the channel 1627. In some examples, the retention feature 1628 includes a protrusion, lip, or other such structure extending from a side of the channel 1627 to at least partially capture the antenna 1608 within the channel 1627. The one or more retention features 1628 can be disposed at one or more various locations along the channel 1627. In this way, the antenna 1608 can be maintained within the channel 1627 to locate and position the antenna 1608 in a selected position with respect to the header core 1620. In further examples, the one or more retention features 1628 and the channel 1627 of the antenna attachment feature 1626 maintain the antenna 1608 in the selected position during forming of the header shell 1640 around the header core 1620. In still further examples, the channel 1627 and the one or more retention features 1628 are formed to facilitate molding of the header shell 1640 around and/or within the antenna attachment feature 1626 while inhibiting void spaces in molding, which could lead to mold problems, such as delamination of the header shell 1640 from the header core 1620.

In some examples, the channel 1627 can be configured to accept the antenna 1608 within the channel 1627, and, instead of or in addition to using one or more retention features 1628 to retain the antenna 1608 within the channel 1627, the channel 1627 can be configured to allow crimping of one or more portions of the channel 1627 to retain the antenna 1608 within the channel 1627. For instance, a portion of the channel 1627 can include walls that extend from a surface of the header core 1620 to allow a crimping tool, for instance, to engage with the walls and crimp the walls of the channel 1627 to retain the antenna 1608 within the channel 1627. In other examples, the channel 1627 includes one or more portions configured to allow crimping and/or deformation of the one or more portions for retention of the antenna 1608 within the channel 1627.

In some examples, instead of or in addition to using an antenna similar to the example antennas 808, 1508, 1608 described above, an antenna can be printed on a portion of an IMD. In some examples, the antenna can be printed on a surface of a header core. In other examples, the antenna can be printed on another portion of the IMD. In some examples, the antenna can be printed using a conductive material or combination of materials. In an example, the antenna is printed in a manner configured to allow formation of the antenna to a particular thickness. For instance, the antenna can be formed to a thickness of approximately 10 micrometers. In other examples, the antenna can be formed to a thickness of greater than or less than 10 micrometers, provided the antenna is capable of functioning as described herein.

In further examples, the header core 1620 can include one or more material relief features 1635 at locations, such as at one or more cavities 1634 of the header core 1620. In some examples, the material relief feature 1635 allows for a reduced likelihood of delamination occurring between the header core 1620 and the header shell 1640. For instance, the relief feature 1635 can be positioned at a location where delamination is more likely to occur to provide a safeguard against delamination. In some examples, the relief feature 1635 can include a ridge or other protrusion that acts to provide a break in the continuity of a surface and, therefore, provide a barrier against continued delamination. For example, if delamination begins at a location, such delamination will continue across a surface until a break in the surface (like a ridge, for instance) is encountered, at which point delamination will be contained. As such, in some examples, the relief feature 1635 of the header core 1620 can include a ridge, protrusion, or other relief feature at or near one or more locations in the header core 1620 which have an increased likelihood of being a nucleation site of delamination, such as around the cavity 1634. In further examples, one or more locations of the header core 1620 other than or in addition to the one or more cavities 1634 include a relief feature. In still further examples, the one or more relief features 1635 are configured to allow substantially free flow of mold material and escape of air during overmolding of the header shell 1640, thereby allowing for a reduced number of mold defects (e.g., void spaces and the like) in the header shell 1640.

In some examples, the header 1610 can be formed from one or more of the materials described herein. In some examples, an adhesive can be used to attach the header 1610 to the device container 1602, as described herein. In some examples, the device container 1602 can include a textured surface for attachment of the header 1610 to the device container 1602, as described herein.

Figure 17:
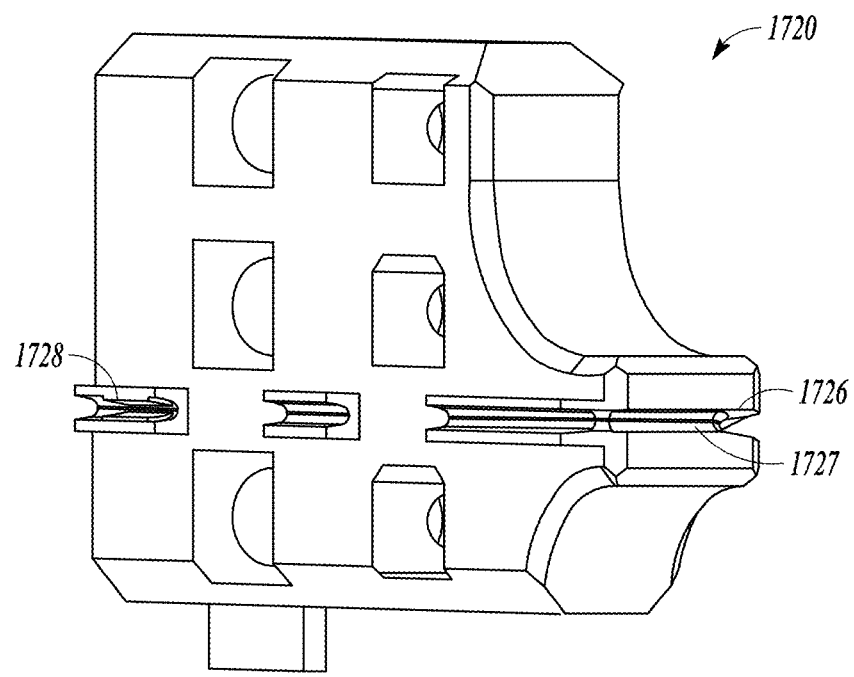
FIG. 17 shows an example header core of an IMD according to an embodiment of the invention.

Referring to FIG. 17, in some examples, a header core 1720 includes an antenna attachment feature 1726 configured to locate and/or support an antenna in a selected position with respect to the header core 1720. In some examples, the antenna attachment feature 1726 includes a channel 1727 configured to at least partially receive the antenna. In some examples, the channel 1727 can extend along one or more sides of the header core 1720, depending on the desired configuration, position, and/or location of the antenna with respect to the header core 1720. In further examples, the channel 1727 can extend continuously or can be broken into segments on one or more sides of the header core 1720. The antenna attachment feature 1726, in some examples, is integrally formed in the header core 1720. For instance, the antenna attachment feature 1726 can be molded and/or machined into the header core 1720. In further examples, the antenna attachment feature 1726 can be affixed to the header core 1720 using an adhesive, for instance. In still further examples, the antenna attachment feature 1726 can be engaged with the header core 1720 using complementary engagement features or the like.

In some examples, the antenna attachment feature 1726 includes one or more retention features 1728 configured to retain the antenna within the channel 1727. In some examples, the retention feature 1728 includes a narrowed portion of the channel 1727 configured to frictionally engage at least a portion of the antenna. The one or more retention features 1728 can be disposed at one or more various locations along the channel 1727. In this way, the antenna can be maintained within the channel 1727 to locate and position the antenna in a selected position with respect to the header core 1720. In further examples, the one or more retention features 1728 and the channel 1727 of the antenna attachment feature 1726 maintain the antenna in the selected position during forming of a header shell around the header core 1720. In still further examples, the channel 1727 and the one or more retention features 1728 are formed to facilitate molding of the header shell around and/or within the antenna attachment feature 1726 while inhibiting void spaces in molding, which could lead to mold problems, such as delamination of the header shell from the header core 1720.

Figure 18:
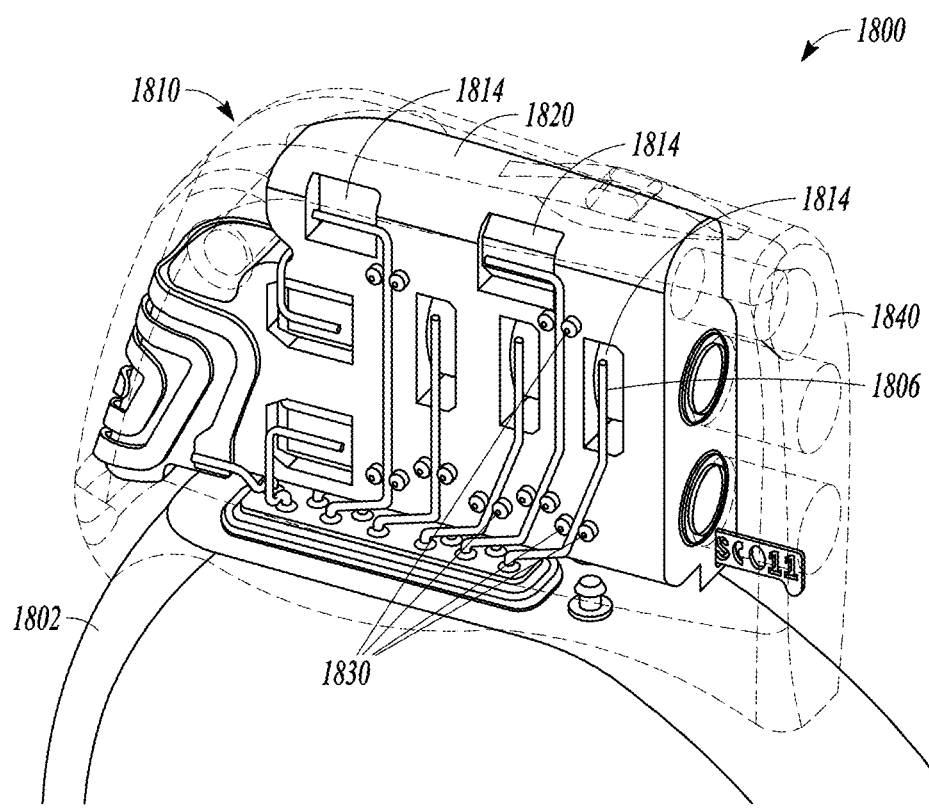
FIG. 18 shows an example header of an IMD according to an embodiment of the invention.

Referring to FIG. 18, in some examples, an IMD 1800 includes a header 1810 attached to a device container 1802, the header 1810 including a header shell 1840 disposed around a header core 1820. In some examples, the header core 1820 includes one or more locating features 1830 for locating and/or routing one or more wires 1806 of the IMD 1800. In some examples, the one or more locating features 1830 act to maintain spacing between the one or more wires 1806 and other wires 1806, electrical contacts 1814, and other conductive components of the IMD 1800 to limit the likelihood of shorting between the one or more wires 1806 and other wires 1806, electrical contacts 1814, and other conductive components of the IMD 1800. In some examples, the one or more locating features 1830 are protrusions extending outwardly from the header core 1820. In the example shown in FIG. 18, the locating features 1830 are substantially cylindrical protrusions positioned in pairs to accommodate the wires 1806 therebetween to limit movement of the wires 1806 and lessen the likelihood of shorting of the wires 1806. In further examples, the one or more locating features 1830 can be used to facilitate inspection of the one or more wires 1806. That is, the locating features 1830 allow one to see where the wire 1806 is supposed to be located and to facilitate noticing whether a wire is missing or is otherwise misrouted with respect to the header core 1820.

In various examples, the one or more wires 1806 can be bent prior to the header core 1820 being placed in position with respect to the device container 1802. For instance, prior to affixing the header core 1820 to the device container 1802, each of the one or more wires 1806 can be bent and/or manipulated into a selected configuration, such that the one or more wires 1806 are substantially in place with respect to connection locations on the header core 1820 so that, once the header core 1820 is put in position, the one or more wires 1806 are substantially aligned with the corresponding one or more connection points (for instance, the one or more electrical contacts 1814). The one or more wires 1806 can then be affixed to the corresponding one or more electrical contacts 1814, for instance, using spot welding.

Figure 32:
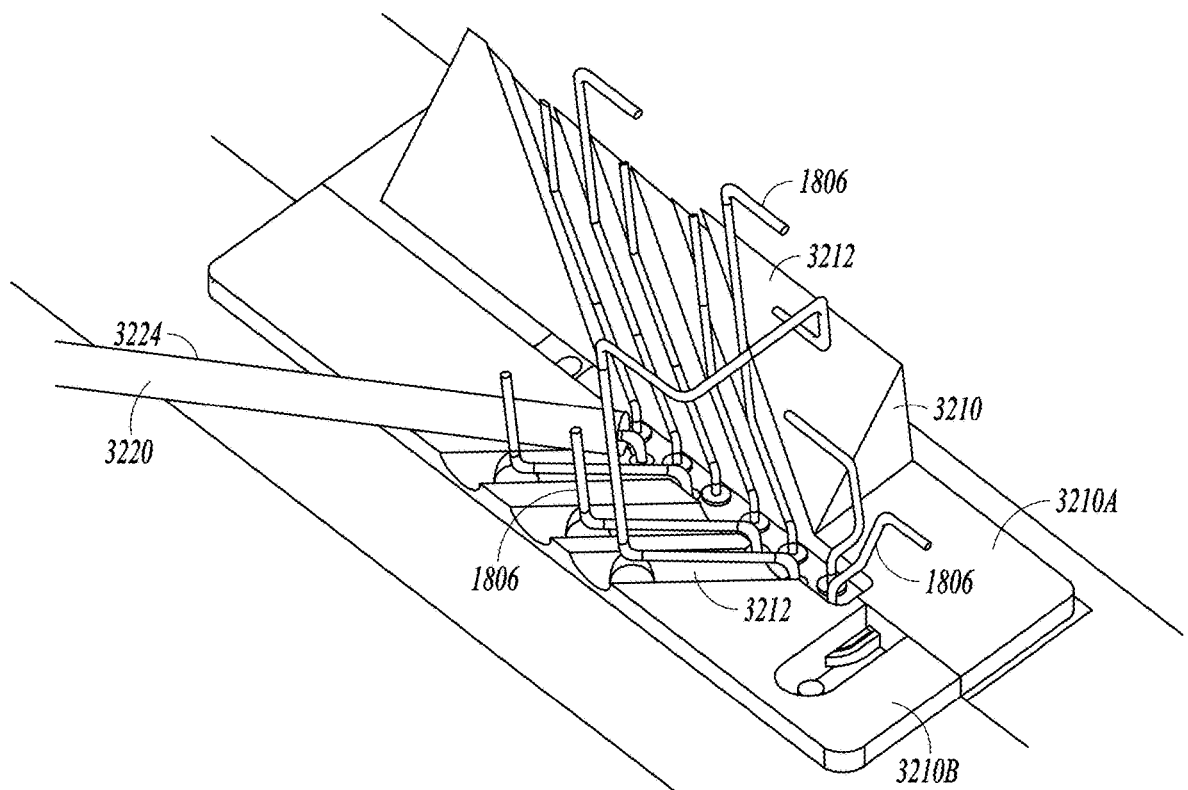
FIG. 32 shows an example forming fixture and bending tool for forming wires of a header of an IMD according to an embodiment of the invention.
Figure 33:
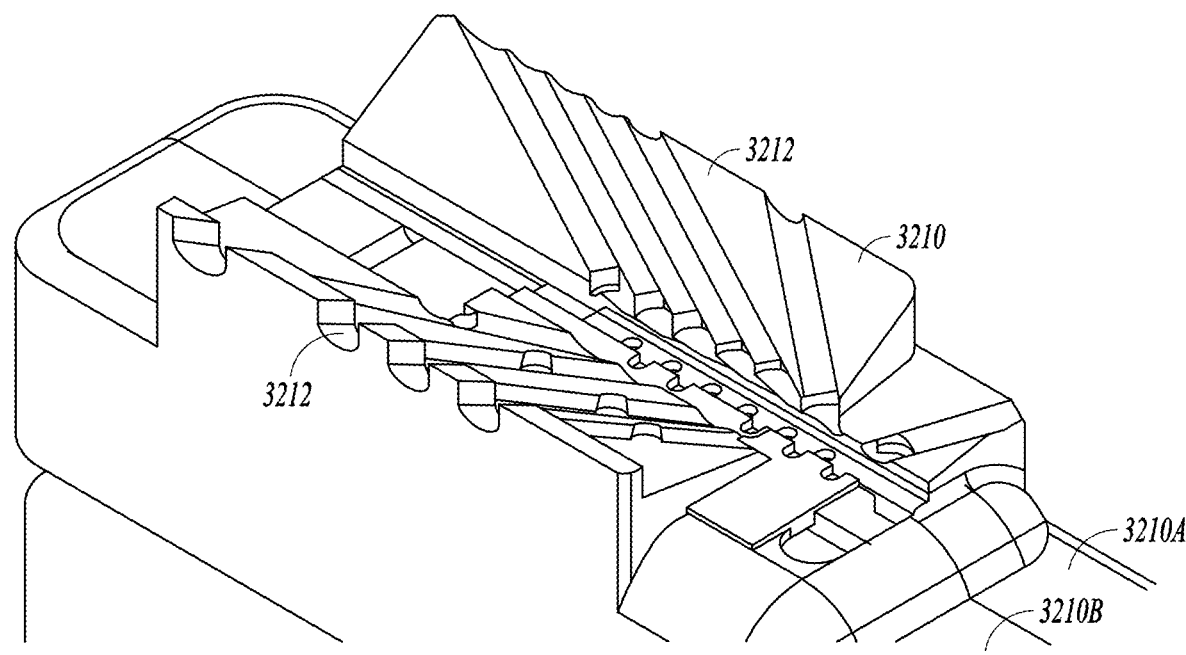
FIG. 33 shows an example forming fixture for forming wires of a header of an IMD according to an embodiment of the invention.
Figure 34:
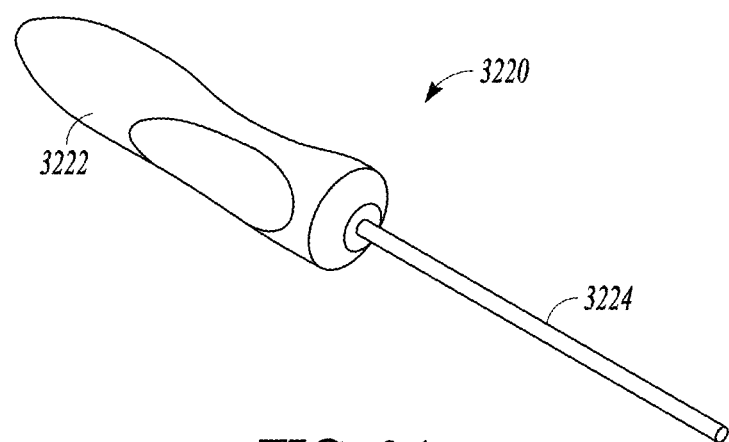
FIG. 34 shows an example bending tool for forming wires of a header of an IMD according to an embodiment of the invention.

In some examples, referring briefly to FIGS. 32-34, a template 3210 and a bending tool 3220 can be used to manually bend the one or more wires 1806 into selected positions for attachment to the header core 1820. The template 3210, in some examples, is engagable with the device container 1802 such that the one or more wires 1806 extend outwardly from the template 3210. The template 3210, in some examples, includes features 3212 (such as, for instance, ridges, channels, or the like) to facilitate bending of the one or more wires 1806 into the selected configurations. The bending tool 3220, in some examples, includes a handle 3222 with a bending tube 3224 extending outwardly from the handle 3222. The bending tube 3224, in some examples, is configured to fit over the wire 1806 (for instance, the wire 1806 can fit inside the bending tube 3224) allowing a user to manipulate the bending tool 3220 and achieve a bend in the wire 1806. Once the one or more wires 1806 are bent into the selected configurations, the template 3210 can be removed from the device container 1802, leaving the one or more wires 1806 bent into the selected configurations. In some examples, the template 3210 is separable (for instance, the template 3210 can include two or more separable portions 3210A, 3210B) to allow the template 3210 to be removed from the device container 1802 without affecting the one or more bends of the one or more wires 1806. In other examples, the one or more wires 1806 can be bent using an automated process, for instance, using a robotic arm preprogrammed to bend the one or more wires 1806 in the selected one or more configurations.

Referring again to FIG. 18, in other examples, the header core 1820 can be placed in position on the device container 1802 and the one or more wires 1806 can be bent into position using the locating features 1830 of the header core 1820 as bending guides. That is, the wire 1806 can be bent to pass through or around the appropriate locating features 1830 to the electrical contact 1814 of the header core 1820.

In some examples, the header 1810 can be formed from one or more of the materials described herein. In some examples, an adhesive can be used to attach the header 1810 to the device container 1802, as described herein. In some examples, the device container 1802 can include a textured surface for attachment of the header 1810 to the device container 1802, as described herein.

Figure 19:
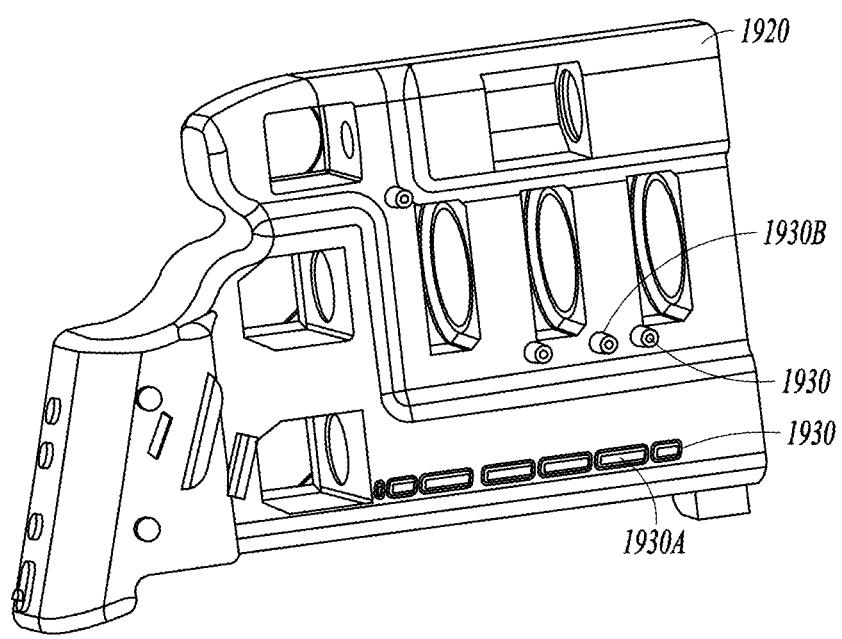
FIG. 19 shows an example header core of an IMD according to an embodiment of the invention.

Referring to FIG. 19, a header core 1920, in some examples, includes one or more locating features 1930 generally similar to the locating features 1830 described herein. In some examples, the one or more locating features 1930 can include generally prismatic protrusions 1930A and/or generally cylindrical protrusions 1930B, each extending outwardly from the header core 1920. In some examples, the prismatic locating features 1930A can be spaced in proximity to one another and can be configured to accommodate a wire therebetween, and the cylindrical locating features 1930B can be positioned on the header core 1920 to locate bends in the wire and/or to constrain the wire from migrating into contact with another wire, an improper electrical contact, or the like.

Figure 20:
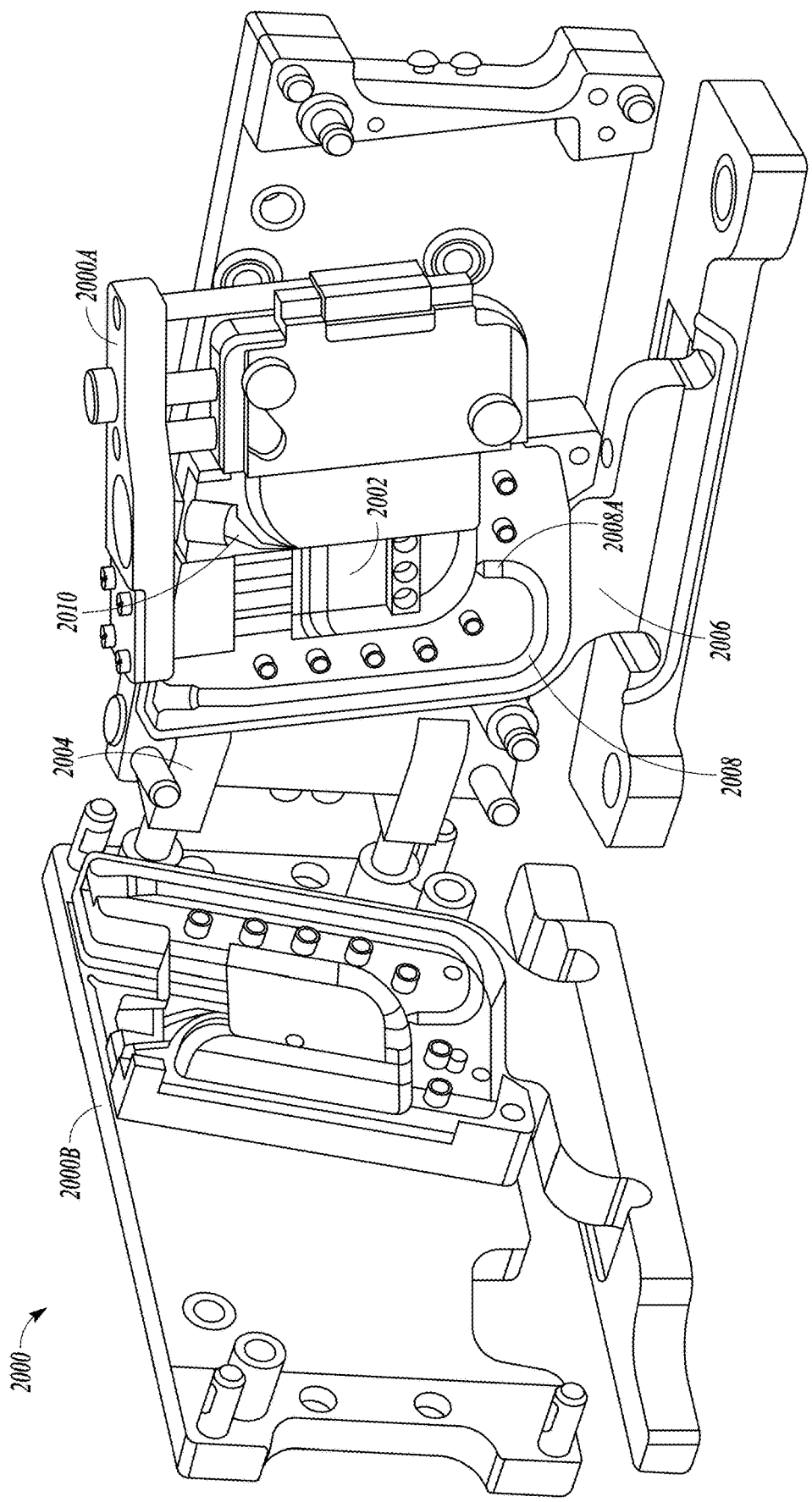
FIG. 20 shows an example mold apparatus for forming a header of an IMD according to an embodiment of the invention.
Figure 21:
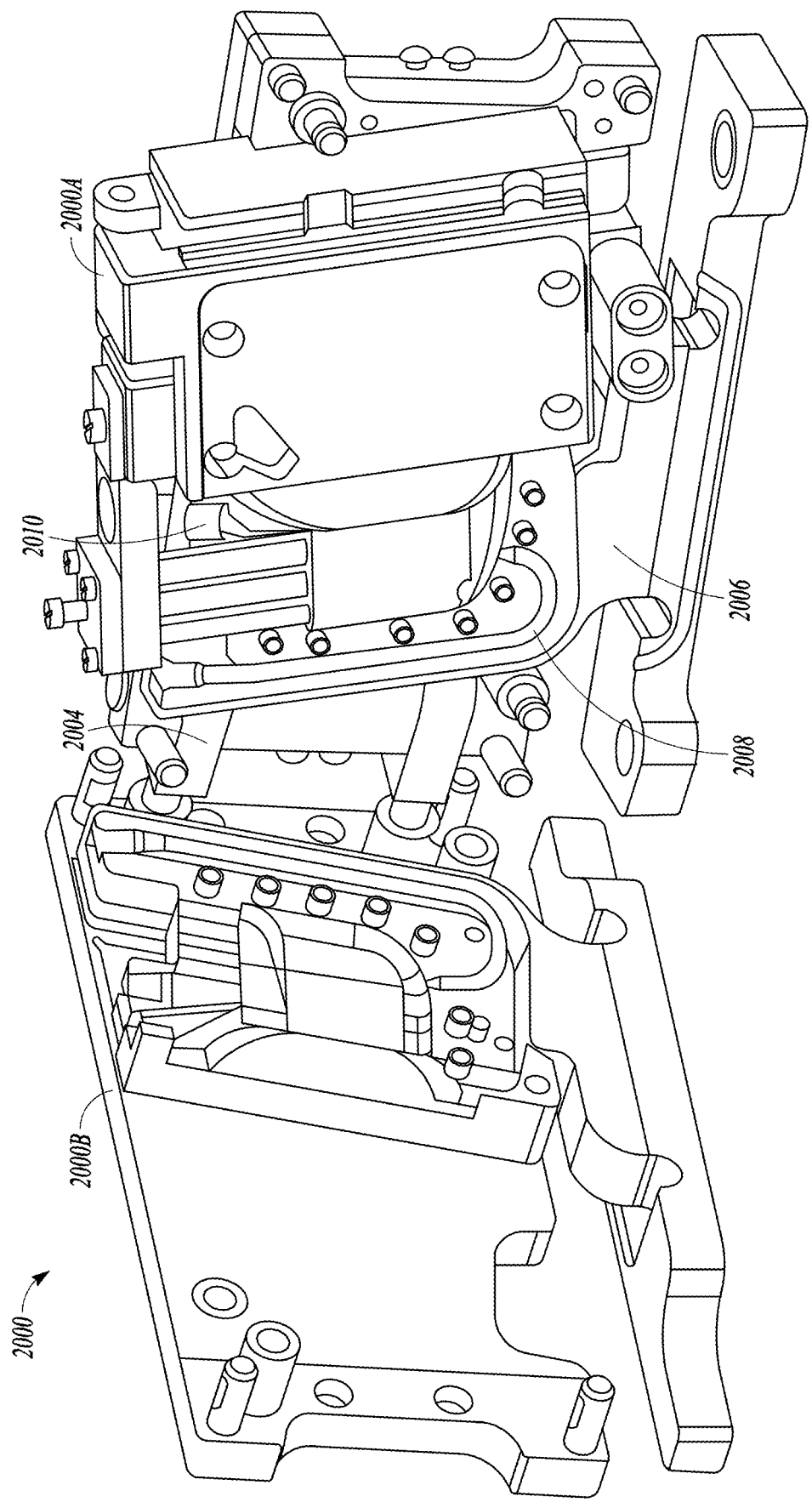
FIG. 21 shows an example mold apparatus for forming a header of an IMD according to an embodiment of the invention.

Referring to FIGS. 20 and 21, in some examples, a mold apparatus 2000 is configured for molding a header shell around or otherwise to a header core and/or a device container of an IMD. In some examples, the mold apparatus 2000 includes a mold cavity 2002 sized to accommodate the header core within the mold cavity 2002 to allow overmolding of the header shell. In further examples, the mold cavity 2002 is sized to accommodate the header core and at least a portion of the device container within the mold cavity 2002 to allow overmolding of the header shell. In some examples, a partially-assembled IMD (including the header core and the device container with electrical connections between components of the header core and one or more modules within the device container) is inserted within the mold cavity 2002 of the mold apparatus 2000 and the mold apparatus 2000 is closed around the partially-assembled IMD. In some examples, the mold apparatus 2000 includes a first portion 2000A and a second portion 2000B joined together with a hinge 2004 to allow the first and second portions 2000A, 2000B to be closed for molding of the header shell and opened for removal of the molded IMD and insertion of another partially-assembled IMD. In other examples, other mold apparatuses having different configurations are contemplated, including mold apparatuses with more than two portions and/or mold apparatuses having different opening/closing configurations, provided the mold apparatuses are capable of molding the header shell around the header core and attaching the header shell to the device container.

In some examples, the mold apparatus 2000 includes a fill tube or port 2008 configured to allow insertion of mold material within the mold cavity 2002. In some examples, the fill tube 2008 includes an opening 2008A into the mold cavity 2002 at a bottom of the mold cavity 2002 to allow for filling of the mold cavity 2002 from the bottom. In further examples, the location of the opening 2008A of the fill tube 2008 allows for low-pressure injection molding of the header shell. In some examples, the location of the opening 2008A of the fill tube 2008 is disposed at a location on the header displaced from an interface between the header and the device container of the IMD. By doing so, stress concentrations (for instance, stress concentrations caused by removal of a sprue or flashing) can be limited at the interface between the header and the device container of the IMD. Such stress concentrations at the interface between the header and the device container of the IMD can lead, in some examples, to premature failure of the header, such as, for instance, at least partial separation of the header from the device container.

In some examples, the mold apparatus 2000 includes a vent tube or port 2010 configured to allow escape of air from within the mold cavity 2002 during filling of the mold cavity 2002 with the mold material. In some examples, the vent tube 2010 is disposed at a top of the mold cavity 2002 to allow for venting of substantially all the air from within the mold cavity 2002. In further examples, the location of the vent tube 2010 is disposed at a location on the header displaced from an interface between the header and the device container of the IMD. By doing so, stress concentrations (for instance, stress concentrations caused by removal of a sprue or flashing) can be limited at the interface between the header and the device container of the IMD. Such stress concentrations at the interface between the header and the device container of the IMD can lead, in some examples, to premature failure of the header, such as, for instance, at least partial separation of the header from the device container. In some examples, the vent tube 2010 is at a location slightly displaced from the interface between the header and the device container, such that substantially all the air of the mold cavity 2002 can escape during filling of the mold cavity 2002 while, at the same time, allowing for displacement of the sprue or flashing from the interface between the header and the device container so that removal of the sprue or flashing from the header will less likely result in stress concentrations at the interface between the header and the device container.

In some examples, the mold apparatus 2000 includes a heating system to allow heating of the mold cavity 2002. After inserting the mold material within the mold cavity 2002, the mold material can be cured by heating the mold cavity 2002. Such heating of the mold cavity 2002 and curing of the mold material can increase quality of the overmolded header shell and/or decrease the likelihood of delamination of the header shell from the header core. For instance, curing of the mold material can cause an adhesion layer to relatively quickly form between the mold material of the header shell and the header core. Such formation of the adhesion layer creates increased adhesion between the header shell and the header core and decreases the likelihood of subsequent delamination of the header shell from the header core.

In some examples, the mold apparatus 2000 includes a high conductivity channel 2006 and a heating system to heat the high conductivity channel 2006. The high conductivity channel 2006, in some examples, extends proximate the mold cavity 2002 and is capable of imparting heat to the mold cavity 2002 and, in turn, to the mold material within the mold cavity 2002. In further examples, the high conductivity channel 2006 is in contact with the mold cavity 2002 (for instance, an outer surface of the mold cavity 2002), to enable the high conductivity channel 2006 to efficiently transfer heat to the mold cavity 2002 and the mold material within the mold cavity 2002. In some examples, the remainder of the IMD within the mold apparatus 2000 (for instance, the device container) is maintained at a lower temperature as compared to the mold material during curing of the mold material. The electronic modules within the device container can be less tolerant to heat and can be damaged by excessive and/or prolonged heat. Thus, it can be desirable to maintain the device container at a decreased temperature as compared to the high conductivity channel 2006 and/or the mold cavity 2002 during curing of the mold material within the mold cavity 2002. In some examples, the temperature of the device container is maintained substantially at or around an ambient temperature during heating of the mold cavity 2002. In some examples, the temperature during curing of the mold material is within the range of 30° C. to 85° C. In some examples, a cure phase can be achieved with a temperature ramp and decay cycle with a start temperature and an end temperature within the range of 30° C. to 85° C. For instance, the cure phase can begin at a start temperature at or above 30° C., ramp up to an end temperature within a range above 30° C. and at or below 85° C., and then decay to a temperature less than the end temperature, at which point the IMD can be removed from the mold apparatus 2000.

Curing times can vary for many different reasons. For instance, curing times can vary based on the mold material being used to form the header shell, the material(s) used to form the header core, environmental conditions of the mold apparatus 2000 (e.g., temperature, humidity, pressure, and the like), curing temperature, and resilience of the components of the IMD to high temperatures, for example. In some examples, the curing time for the mold apparatus 2000 and IMD configuration is within the range of about ten to thirty minutes. In other examples, the curing time can be more than 30 minutes or less than ten minutes.

In various examples, upon completion of the desired time of curing, the IMD can be removed from the mold apparatus 2000 for inspection and/or final processing of the IMD. For instance, various aspects of the molding process can leave flashing or other molding residue. During final processing, the flashing or residue can be removed, for instance, from an exterior of the header shell, within bores of the header, within or around seal plug areas, in an interface area between the header and the device container, within suture holes, and the like.

Figure 35:
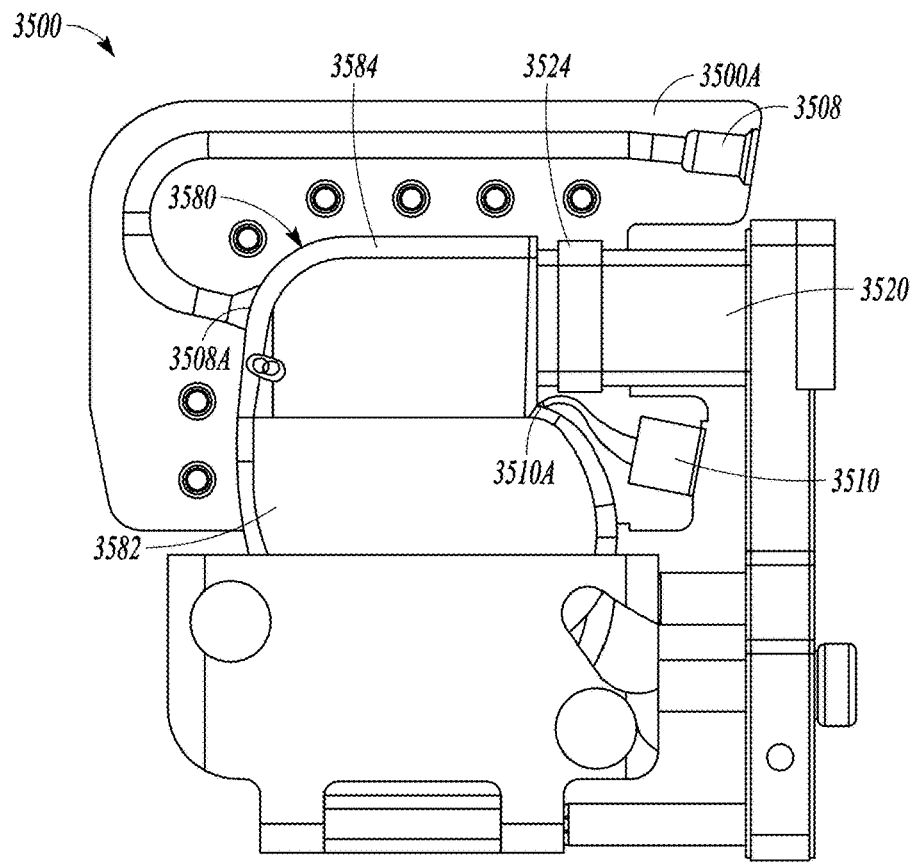
FIG. 35 shows an example mold apparatus for forming a header of an IMD according to an embodiment of the invention.
Figure 36:
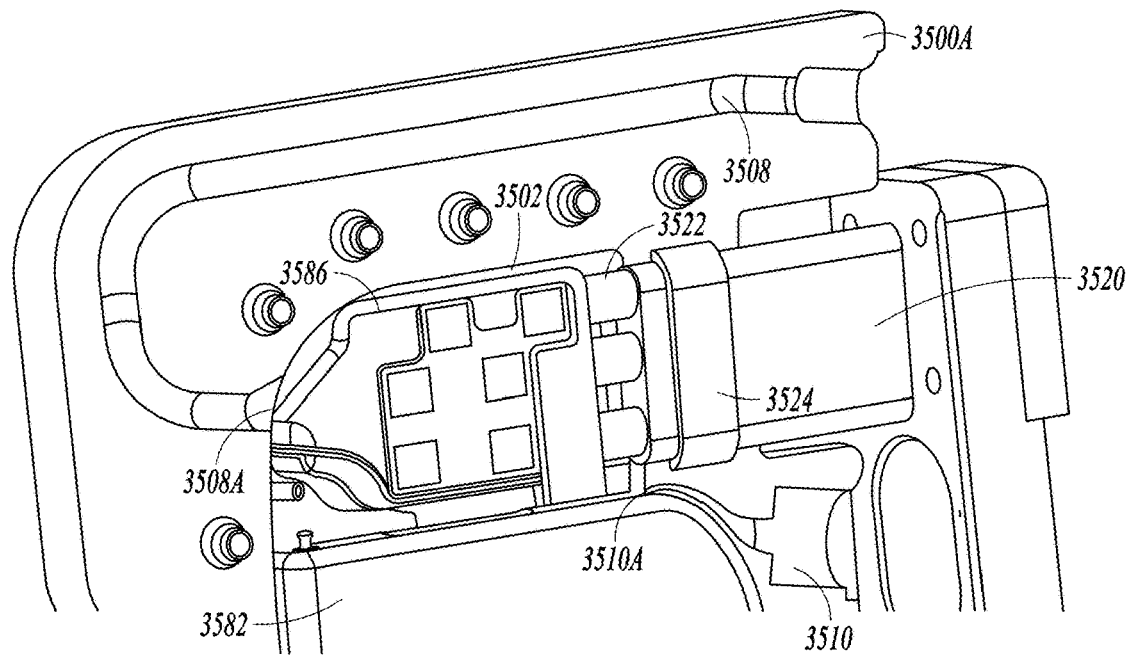
FIG. 36 shows an example mold apparatus for forming a header of an IMD according to an embodiment of the invention.
Figure 37:
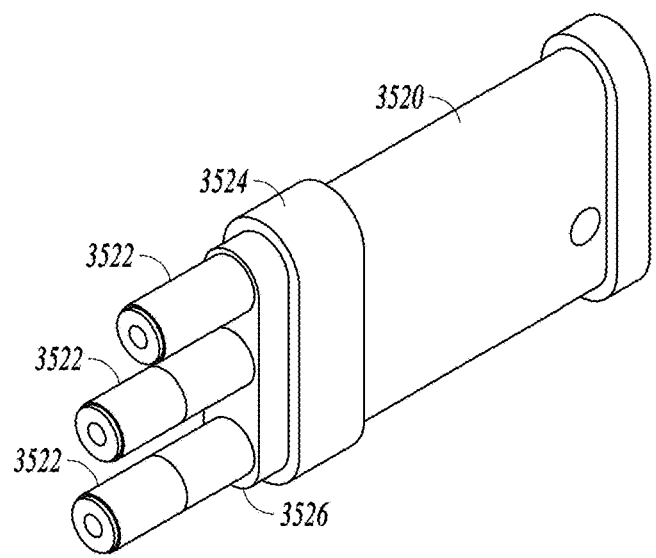
FIG. 37 shows a component of an example mold apparatus for forming a header of an IMD according to an embodiment of the invention.

Referring to FIGS. 35-37, in some examples, a mold apparatus 3500 is configured for molding a header shell 3584 around or otherwise to a header core 3586 and/or a device container 3582 of an IMD 3580. In some examples, the mold apparatus 3500 includes a mold cavity 3502 sized to accommodate the header core 3586 within the mold cavity 3502 to allow overmolding of the header shell 3584. In further examples, the mold cavity 3502 is sized to accommodate the header core 3584 and at least a portion of the device container 3582 within the mold cavity 3502 to allow overmolding of the header shell 3584. In some examples, a partially-assembled IMD (including the header core 3586 and the device container 3582 with electrical connections between components of the header core 3586 and one or more modules within the device container 3582) is inserted within the mold cavity 3502 of the mold apparatus 3500 and the mold apparatus 3500 is closed around the partially-assembled IMD. In some examples, the mold apparatus 3500 includes a first portion 3500A and a second portion joined together with a hinge, in a manner similar to that described herein and shown in FIGS. 20 and 21, to allow the first portion 3500A and the second portion to be closed for molding of the header shell 3584 and opened for removal of the molded IMD 3580 and insertion of another partially-assembled IMD. In other examples, other mold apparatuses having different configurations are contemplated, including mold apparatuses with more than two portions and/or mold apparatuses having different opening/closing configurations, provided the mold apparatuses are capable of molding the header shell around the header core and attaching the header shell to the device container.

In some examples, the mold apparatus 3500 includes a block 3520 configured to reduce if not eliminate flashing from occurring proximate to one or more bore holes of the header shell 3584. Flashing can occur at junctions between mold pieces. That is, a space present between mold pieces and accessible from the mold cavity can be susceptible to incursion of mold material during the molding process, which, when cured, forms flashing on the molded item. This flashing can often be removed in post processing, thus adding at least an additional step to the manufacturing of the molded item and increasing time and/or cost of manufacturing. In the manufacturing of the IMD 3580, in some examples, flashing present at or proximate to the one or more bore holes of the header shell 3584 can present issues with insertion of one or more leads (or other devices) within the one or more bore holes, such as improper or insufficient engagement of the lead within the bore hole, for instance. Such flashing can generally be removed during post processing, but, as stated, the removal adds time and/or cost to the process. In other examples, removal of flashing from the one or more bore holes can be difficult due to the geometry of the area around the one or more bore holes and/or due to contaminants from the removal process potentially entering the one or more bore holes of the header shell 3584. For at least this reason, in some examples, maintaining mold junctions (or other mold features that can give rise to flashing) spaced from the one or more bore holes of the header shell 3584 is contemplated.

In some examples, the block 3520 is maintained within the mold apparatus 3500 during overmolding of the header shell 3584 to displace potential flashing away from the one or more bore holes of the header shell 3584. In some examples, the block 3520 includes one or more pins 3522 configured to fit within a corresponding one or more bore hole portions of the header core 3586 to inhibit mold material from entering the one or more bore hole portions of the header core 3586 and to form the remainder of the one or more bore holes of the header shell 3584. In some examples, the block 3520 includes a flange 3524 or other structure to engage within at least one of the first portion 3500A or the second portion of the mold apparatus 3500 to define the mold cavity 3502 during the molding process. In various examples, the block 3520 includes a surface 3526 sized, shaped, or otherwise configured to displace potential flashing away from the one or more bore holes of the header shell 3584 to a location of the header shell 3584 where the potential flashing is not likely to inhibit engagement of leads or other devices within the one or more bore holes. In the example, shown in FIG. 37, the surface 3526 is generally an elongated, flattened ellipse sized to displace potential flashing to a perimeter of the surface 3526, which is displaced from the bore holes of the header shell 3584 formed by the pins 3522 of the block 3520 during the molding process. In an example, if no block were used and two mold portions with a junction along a center line of the header shell were used, flashing would likely result at the junction between the mold portions, which would be along a center line of each of the one or more bore holes of the header shell. By using the block 3520 within the mold apparatus 3500, one or more junction locations of the mold apparatus 3500 can be moved away from the one or more bore holes of the header shell 3584 to a location on the header shell 3584 where, for instance, resulting flashing does not adversely affect engagement of leads or other devices within the one or more bore holes of the header shell 3584. In addition, the resulting flashing can be relatively easily removed from the header shell 3584 after molding of the header shell 3584 as compared to the removal of flashing from in and around more complex structures or geometries of the header shell, such as the one or more bore holes.

In some examples, use of the block 3520 with the mold apparatus 3500 can allow for more stable junctions and/or sealing surfaces between components of the mold apparatus 3500 to further limit flashing occurring during molding. That is, the larger surface areas of the junctions between the first portion 3500A, the second portion, and the block 3520 can allow for a tighter, more stable junction between the components of the mold apparatus 3500 than would be achievable using, for instance, a two-component mold apparatus with relatively little surface area between bore hole locations in such a mold apparatus. In this way, the mold apparatus 3500 can inhibit formation of flashing or displace potential flashing away from the one or more bore holes of the header shell 3584 during overmolding of the header shell 3584 around the header core 3586.

In some examples, the mold apparatus 3500 can include a fill tube or port 3508 configured to allow insertion of mold material within the mold cavity 3502. In some examples, the fill tube 3508 includes an opening 3508A into the mold cavity 3502 at a bottom of the mold cavity 3502 to allow for filling of the mold cavity 3502 from the bottom (when positioned in a molding configuration, similar, for instance to that shown in the examples of FIGS. 20 and 21). In further examples, the location of the opening 3508A of the fill tube 3508 can allow for low-pressure injection molding of the header shell. In some examples, the location of the opening 3508A of the fill tube 3508 is disposed at a location on the header shell 3584 displaced from an interface between the header shell 3584 and the device container 3582 of the IMD 3580. By doing so, stress concentrations (e.g., stress concentrations caused by removal of a sprue or flashing) can be limited at the interface between the header shell 3584 and the device container 3582 of the IMD 3580. Such stress concentrations at the interface between the header shell 3584 and the device container 3582 of the IMD 3580 can lead to premature failure of the header shell 3584, such as at least partial separation of the header shell 3584 from the device container 3582.

In some examples, the mold apparatus 3500 includes a vent tube or port 3510 configured to allow air to escape from within the mold cavity 3502 during filling of the mold cavity 3502 with the mold material. In some examples, the vent tube 3510 is disposed at a top of the mold cavity 3502 to allow for venting of substantially all the air from within the mold cavity 3502 (when positioned in a molding configuration, similar, for instance to that shown in the examples of FIGS. 20 and 21). In further examples, the location of the vent tube 3510 is disposed at a location on the header shell 3584 displaced from an interface between the header shell 3584 and the device container 3582 of the IMD 3580. By doing so, stress concentrations can be limited at the interface between the header shell 3584 and the device container 3582 of the IMD 3580, as stated herein. In some examples, the vent tube 3510 can be at a location slightly displaced from the interface between the header shell 3584 and the device container 3582 such that substantially all the air of the mold cavity 3502 can escape during filling of the mold cavity 3502 while at the same time allowing for displacement of the sprue or flashing from the interface between the header shell 3584 and the device container 3582. The vent tube 3510 displacement can enable removal of the sprue or flashing from the header shell 3584 that is less likely to result in stress concentrations at the interface between the header shell 3584 and the device container 3582.

Figure 22:
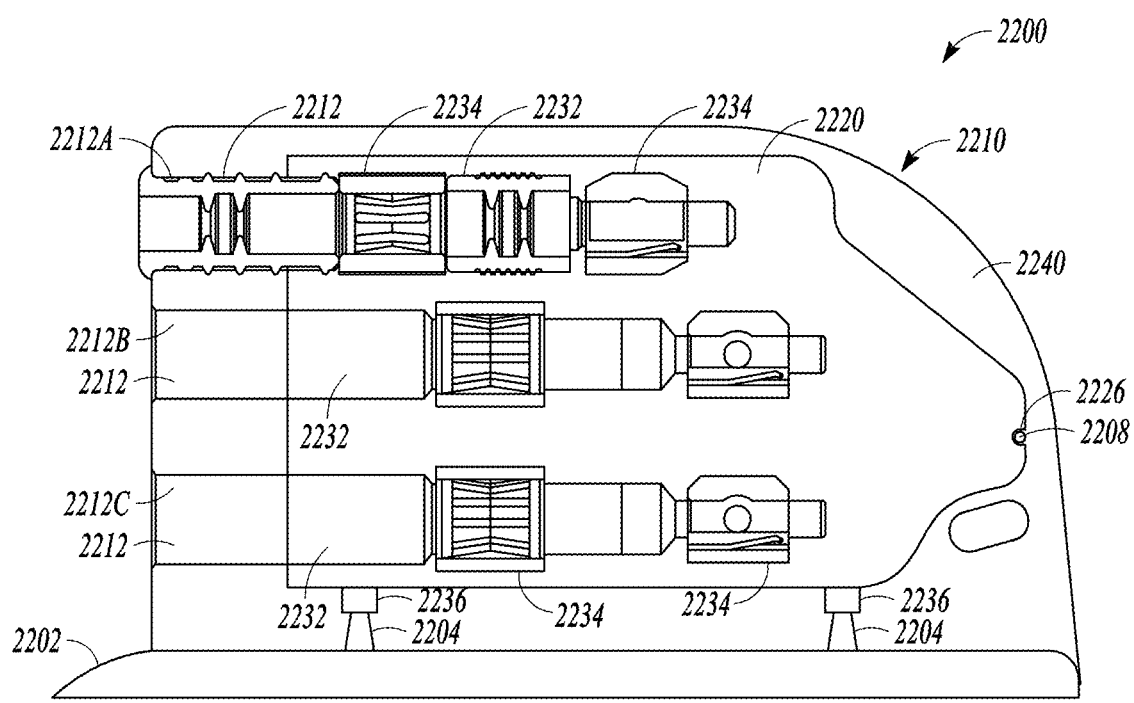
FIG. 22 shows a cross-sectional view of an example header of an IMD according to an embodiment of the invention.

Referring to FIG. 22, in some examples, an IMD 2200 includes a header 2210 including a header core 2220 and a header shell 2240 disposed around the header core 2220. In various examples, the header 2210 includes one or more bore holes 2212. In the example shown in FIG. 22, the header 2210 includes three bore holes 2212A, 2212B, 2212C. In other examples, however, the header can include more or fewer than three bore holes, depending on the intended application for the IMD. In some examples, as described herein, the header core 2220 can be formed first and then attached to the device container 2202 by molding the header shell 2240 around the header core 2220 and to the device container 2202. In some examples, the header 2210 can be formed from one or more of the materials described herein. In some examples, an adhesive can be used to attach the header 2210 to the device container 2202, as described herein. In some examples, the device container 2202 can include a textured surface for attachment of the header 2210 to the device container 2202, as described herein.

In some examples, the header core 2220 includes one or more bore hole portions 2232 formed within the header core 2220. The one or more bore hole portions 2232, in various examples, correspond to the number of bore holes 2212 of the header 2210. The bore hole portions 2232 can be formed during molding of the header core 2220, or formed by machining of the header core 2220.

In some examples, the header core 2220 includes one or more cavities 2234 configured to allow insertion of components (e.g., electronic connection features) within or otherwise proximate to the one or more bore hole portions 2232. Such components can include, but are not limited to, a connector block, a seal ring, a tip connector, or the like. In various examples, the cavity 2234 can be formed through a side of the header core 2220 and intersect the bore hole portion 2232, so that a component can be inserted into the cavity 2234 from the side of the header core 2220 and be placed in position within the bore hole portion 2232. Alternatively, some components can be placed through the bore hole portion 2232 and located in position within the header core 2220. In this way, the header core 2220 can be formed to allow precise location of the components within the one or more bore hole portions 2232 of the header core 2220. As such, in some examples, the components can be precisely located within the header core 2220 after formation of the header core 2220 and do not need to be molded into place within the header core, for instance, using a mandrel to locate the components with respect to each other and/or the header core. In some examples, the header core 2220 includes at least two components or electronic connection features disposed within the bore hole portion 2232, wherein the header core 2220 is configured to allow location of the at least two components or electronic connection features in a selected configuration within the bore hole portion 2232. For instance, the two components or electronic connection features can be located a selected distance apart using one or more of the cavities 2234 and/or the one or more bore hole portions 2232 of the header core 2220 after the header core 2220 has been formed and do not require molding of the header core around the components disposed on a mandrel.

The one or more bore hole portions 2232 can be inspected to confirm proper geometry, location with respect to other bore hole portions 2232, and/or location within the head core 2220. Once some or all of the components are located within the header core 2220, the components of the header core 2220 can be tested to ensure proper placement within the bore hole portions 2232 and/or proper conductive functioning. By forming the bore hole portions 2232 prior to connection of the header 2210 with the device container 2202, the header core 2220 and the bore hole portions 2232 can be tested and/or inspected prior to attachment of the header core 2220 to the device container 2202. In some examples, the header core 2220 is formed to accept two or more components (such as electronic connection features, for instance) within cavities 2234 and/or bore hole portions 2232, and the locations of the components with respect to one another and with respect to other features of the header core 2220 can be inspected, tested, or otherwise viewed prior to attachment of the header core 2220 to the device container 2202. As described herein, enabling testing and/or inspection of the header core 2220 allows defective header cores 2220 to be fixed or discarded prior to attachment with the device container 2202, thereby limiting losses associated with defective headers.

In some examples, components within the one or more bore hole portions 2232 and/or cavities 2234 can be sealed within the header core 2220 prior to overmolding of the header shell 2240 and/or connection with the device container 2202. Sealing of such components within the header core 2220 can inhibit mold material infiltrating the one or more bore hole portions 2232 between the header core 2220 and the components during overmolding of the header shell 2240.

In some examples, sealing can be achieved by using a sealant or a bonding agent between the component and the header core 2220. However, use of the sealant or bonding agent introduces a further material to the manufacturing of the header core 2220. In some examples, the sealant or bonding agent can include an adhesive, such as a medical adhesive. In some examples, the sealant or bonding agent can include one or more of an epoxy, an acrylic, or a polymer, such as, for instance, a hot-dispense polyurethane. In some examples, the sealant or bonding agent can include one or more of a two-part epoxy and a cured epoxy. In some examples, the sealant or bonding agent can include a cured urethane acrylic. In some examples, the cured urethane acrylic and/or the cured epoxy can be cured using ultraviolet to visible light.

In some examples, a recess is formed around each of the one or more cavities 2234 configured to allow application of the sealant or bonding agent around the one or more components. The sealant or bonding agent can have a viscosity that allows the sealant or binding agent to be applied to the desired one or more cavities 2234 and/or components but inhibits the sealant or bonding agent from seeping between the component and the cavity 2234 and entering into the bore hole portion 2232.

In other examples, a thermal process can be used to seal the component within the header core 2220. For instance, in some examples, heating of the header core 2220 including the one or more components installed within the header core 2220 can slightly melt the material of the header core 2220 around the one or more components, causing the melted material of the header core 2220 to adhere to the one or more components. The header core 2220 can then cool, solidifying the melted material around the one or more components and thereby sealing the one or more components within the header core 2220. In some examples, such heating of the header core 2220 can be accomplished by induction heating, laser heating, microwave heating, or radiant heating. In still other examples, such heating of the header core 2220 can be accomplished by direct heating, such as, for instance, applying a heating element to the component to heat the component and slightly melt the material around the component.

In some examples, the header core 2220 can be formed of polyurethane, which can be fused to the one or more components using such heating techniques described herein. For example, a ten to fifteen second pulse of induction, laser, or other heating can effectively close at least some, if not all, of the gaps present between the header core 2220 and the one or more components. Such heating techniques may also be employed for header cores 2220 formed from materials other than polyurethane in order to fuse, seal, or otherwise bond the one or more components within the header core 2220. However, heat pulse times for other materials can vary in order to substantially fuse the one or more components within the header core 2220.

In further examples, the header core 2220 can include various other features. For example, the header core 2220 can include one or more feet 2236 to define a standoff between the header core 2220 and the device container 2202. The one or more feet 2236 can allow the header core 2220 to be positioned parallel to a portion of the device container 2202. In addition, the one or more feet 2236 can be placed against or in engagement with a corresponding one or more anchor posts 2204 of the device container 2202. In further examples, the header core 2220 can include an antenna attachment feature 2226 similar to those described herein for locating, supporting, and/or attaching an antenna 2208 with respect to the header core 2220. In still further examples, the header core 2220 can include a tag holder for an identification tag similar to those described herein. In still further examples, the header core 2220 can include one or more locating features for locating and/or routing of one or more wires of the IMD 2200.

The header core 2220 can include one or more material relief features at locations (e.g., at corners) to allow substantially free flow of mold material and escape of air during overmolding of the header shell 2240, thereby allowing for a reduced number of mold defects and a reduced likelihood of delamination occurring between the header core 2220 and the header shell 2240. In some examples, a relief pattern can include a ridge or other protrusion that acts to provide a break in the continuity of a surface and therefore, provide a barrier against continued delamination. As such, in some examples, the header core 2220 can include a ridge, protrusion, or other relief pattern at or near locations in the header core 2220 which have an increased likelihood of being a nucleation site of delamination, such as around a cavity 2234, in particular at a corner of the cavity 2234.

Figure 23:
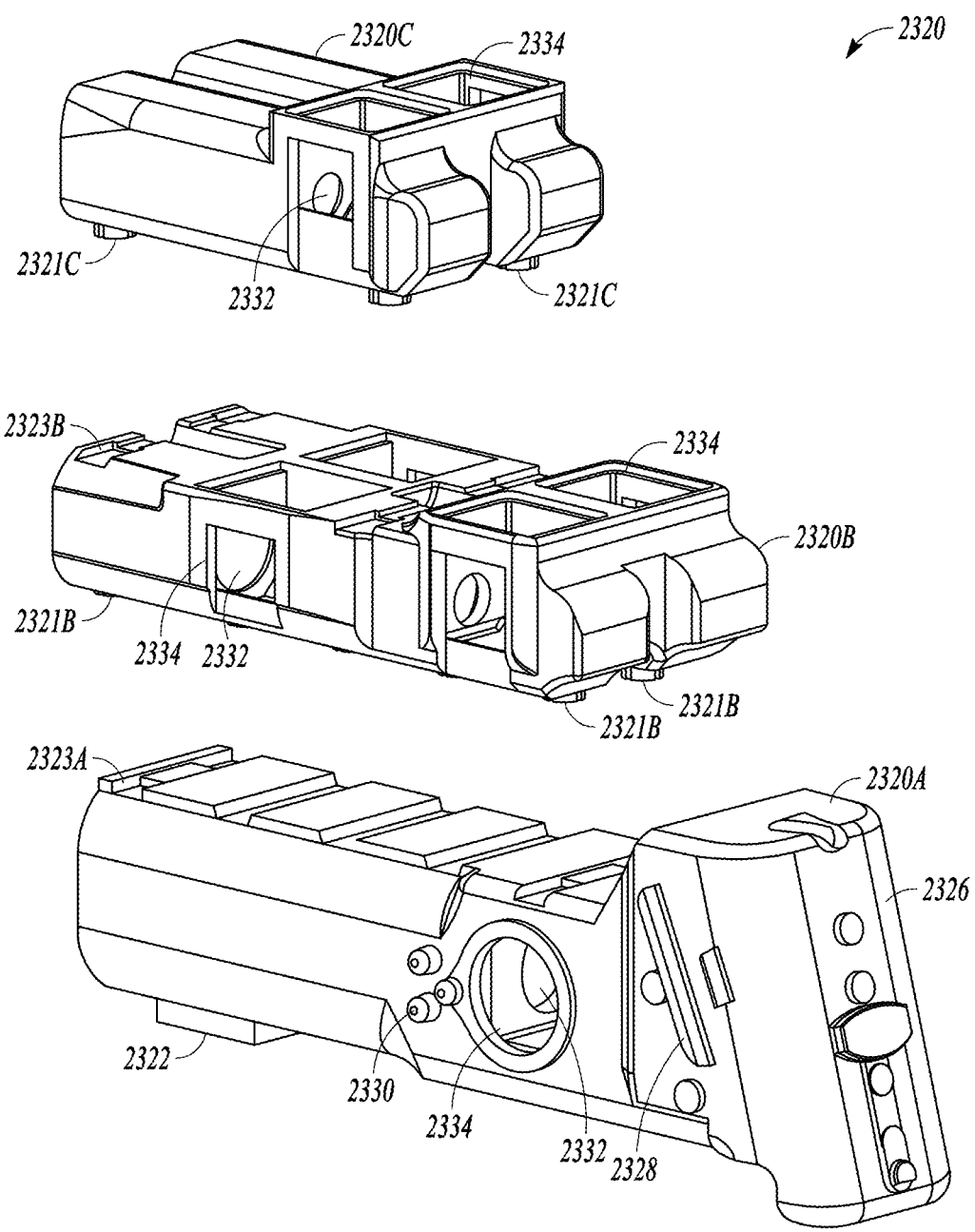
FIG. 23 shows an exploded perspective view of an example header of an IMD according to an embodiment of the invention.
Figure 24:
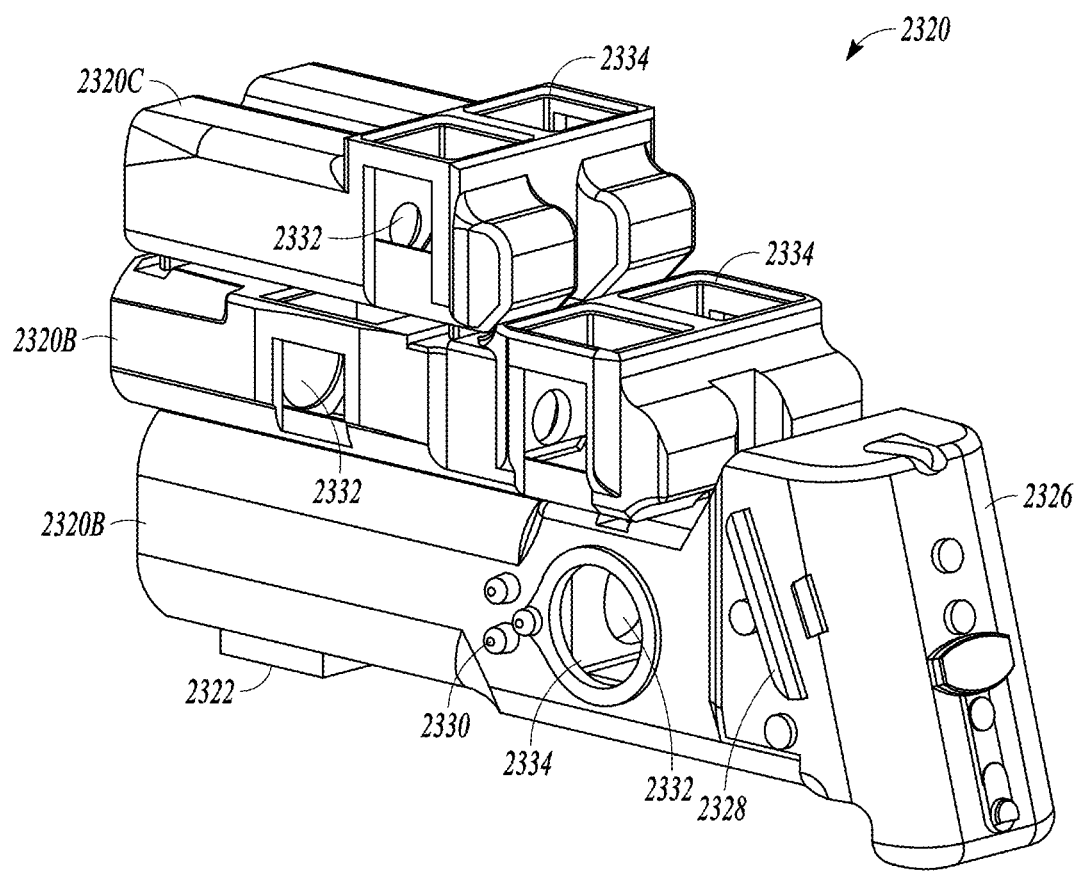
FIG. 24 shows a perspective view of an example header of an IMD according to an embodiment of the invention.

Referring to FIGS. 23 and 24, a modular header core 2320 is shown. The header core 2320, in various examples, can be used in a header of an IMD similar to those described herein. That is, the header core 2320 can be used to attach and locate components of the IMD prior to molding of a header shell around the header core 2320 and also attach the header to a device container of the IMD. In some examples, the header core 2320 can be used in place of the header cores described herein.

In some examples, the modular header core 2320 includes core modules 2320A, 2320B, 2320C that can be selectively coupled together to form the header core 2320. In other examples, the header core 2320 can include more or less than three core modules, depending on the type of IMD in which the header core 2320 is to be used and the application of the IMD. In various examples, the core modules 2320A, 2320B, 2320C can be detachably engaged with one another to form the header core 2320. For instance, the core module 2320A can include one or more engagement features 2323A configured to selectively couple to one or more complementary engagement features 2321B of the core module 2320B to engage the core modules 2320A, 2320B together. In some examples, the engagement features 2323A, 2321B include a peg and a corresponding hole. In some examples, the engagement features 2323A, 2321B engage with a friction fit in order to help maintain engagement of the core modules 2320A, 2320B. In some examples, the engagement feature 2323A includes a substantially rectangular slot and the engagement feature 2321B includes a segmented ring sized and shaped to frictionally fit within the engagement feature 2323A, wherein portions of the segmented ring can be configured to resiliently flex with frictional engagement within the engagement feature 2323A.

In further examples, the module core 2320C includes one or more engagement features 2321C configured to selectively couple to one or more complementary engagement features 2323B of the core module 2320B to engage the core modules 2320B, 2320C together. The engagement features 2323B, 2321C can be similar to the engagement features 2323A, 2321B described herein.

In still further examples, the engagement features 2323A, 2321C can correspond to allow selective engagement of the core modules 2320A, 2320C.

In some examples, at least one of the core modules 2320A, 2320B, 2320C includes a bore hole portion 2332. In further examples, at least one of the core modules 2320A, 2320B, 2320C includes more than one bore hole portion 2332. The one or more bore holes portions 2332, in some examples, can be used to couple to components, such as leads. In some examples, at least one of the core modules 2320A, 2320B, 2320C includes one or more cavities 2334 configured to accept one or more corresponding bore components, such bore components including, but not being limited to, a connector block, a seal ring, a tip connector, or the like. In various examples, the cavity 2334 can be formed through a side of the core module 2320A, 2320B, 2320C of the header core 2320 and intersect the bore hole portion 2332, so that a bore component can be inserted into the cavity 2334 from the side of the header core 2320 and be placed in position within the bore hole portion 2332. Alternatively, some bore components can be placed through the bore hole portion 2332 and located in position within the core module 2320A, 2320B, 2320C of the header core 2320. The bore components, for instance, electrical contacts and the like, can be configured to make electrical contact with a portion of the component (e.g., a terminal of the lead) inserted within the bore hole, in order to electrically couple the lead or other component with at least one electronic module within the device container of the IMD.

The one or more bore hole portions 2332 can be inspected to confirm proper geometry, location with respect to other bore hole portions 2332, and/or location within the head core 2320. Once some or all of the components are located within the header core 2320, the components of the header core 2320 can be tested to ensure proper placement within the bore hole portions 2332 and/or proper conductive functioning. By forming the bore hole portions 2332 prior to connection of the header with the device container, the header core 2320 and the bore hole portions 2332 can be tested and/or inspected prior to attachment of the header core 2320 to the device container, as described herein. In the present examples of the modular header core 2320, not only can the header core 2320 as a whole be tested and inspected, but each of the core modules 2320A, 2320B, 2320C can be tested and/or inspected. If one of the core modules 2320A, 2320B, 2320C is found to be defective in some manner, then the defective core module 2320A, 2320B, 2320C can be fixed or replaced, further limiting losses.

In further examples, various combinations of core modules can be used to form various header cores for use within various types of IMDs. That is, a number of different header cores can be constructed using a relatively small variety of core modules. In various examples, the core modules can be configured to each be capable of engaging with one another, such that different combinations of core modules can be engaged together to form different models of header cores. In this way, stocks of different core modules can be kept, rather than stocks of the different models of header cores, and the various core modules can be engaged in different combinations to form the various models of header cores needed for the various types of IMDs. This allows for header cores to be built-to-need and decreases the need for stockpiles of certain header cores.

Moreover, in some examples, the modular header core 2320 can allow for molds and molding methods of decreased complexity. By separating the header core 2320 into core modules 2320A, 2320B, 2320C, each individual mold for the core modules 2320A, 2320B, 2320C includes a portion of the overall number of cavities 2334 and bore hole portions 2332 of the header core 2320, thereby making for less complex molds for each of the individual core modules 2320A, 2320B, 2320C than a mold configured to form the entire header core with all of the bore hole portions and cavities. Additionally, by molding the core modules 2320A, 2320B, 2320C separately, substantially uniform wall thickness can be achieved in at least a portion of the core modules 2320A, 2320B, 2320C. That is, blocks or otherwise thick portions of mold material (for instance, between bore hole portions) can be limited in the core modules 2320A, 2320B, 2320C, thereby decreasing an amount of mold material needed for forming the header core 2320. Also, because thicker portions of mold material often times are more likely to be the site of voids, sinks, or other molding defects, limiting such thicker portions of the core modules 2320A, 2320B, 2320C can decrease mold defects.

Figure 25:
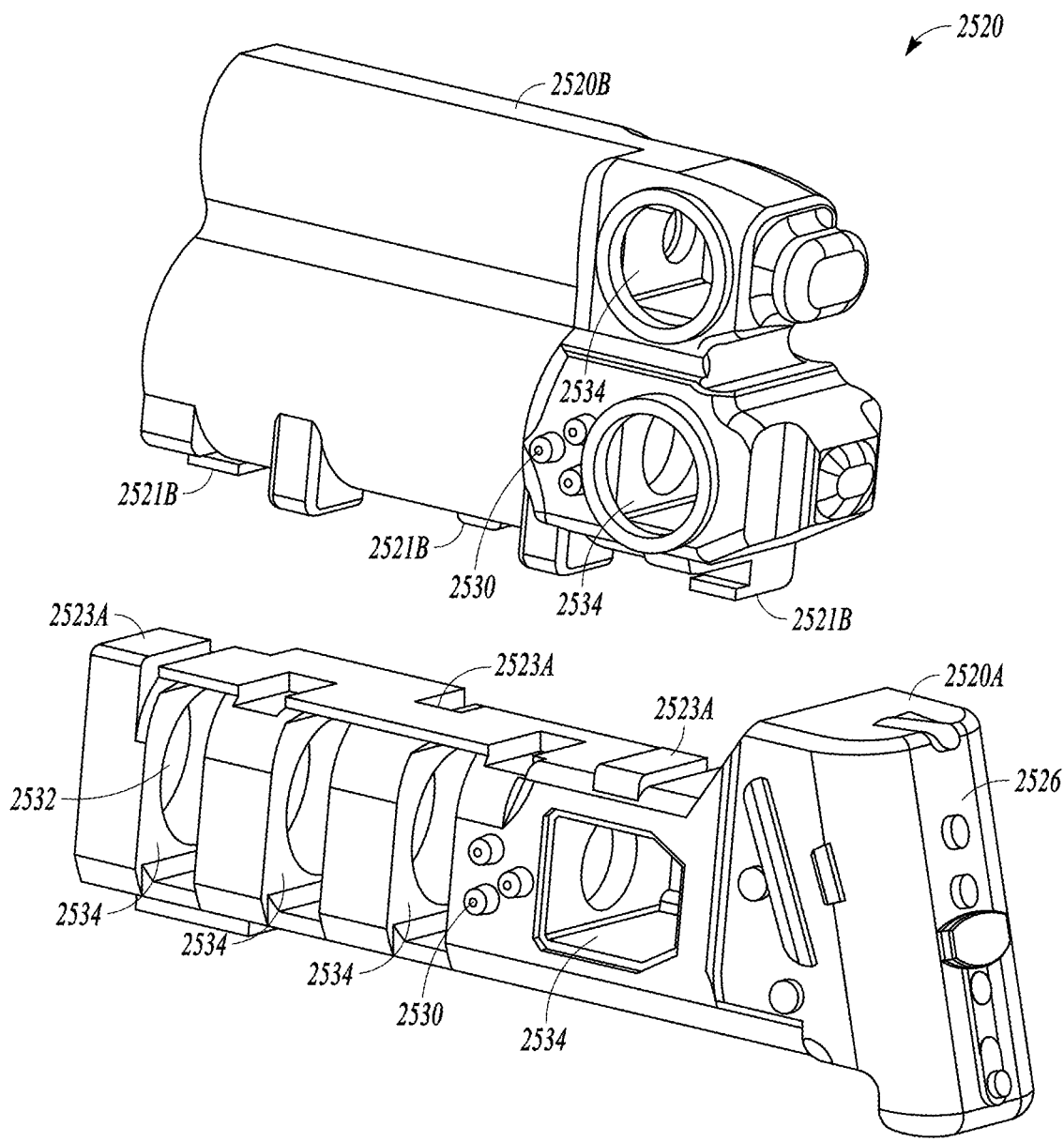
FIG. 25 shows an exploded perspective view of an example header of an IMD according to an embodiment of the invention.
Figure 26:
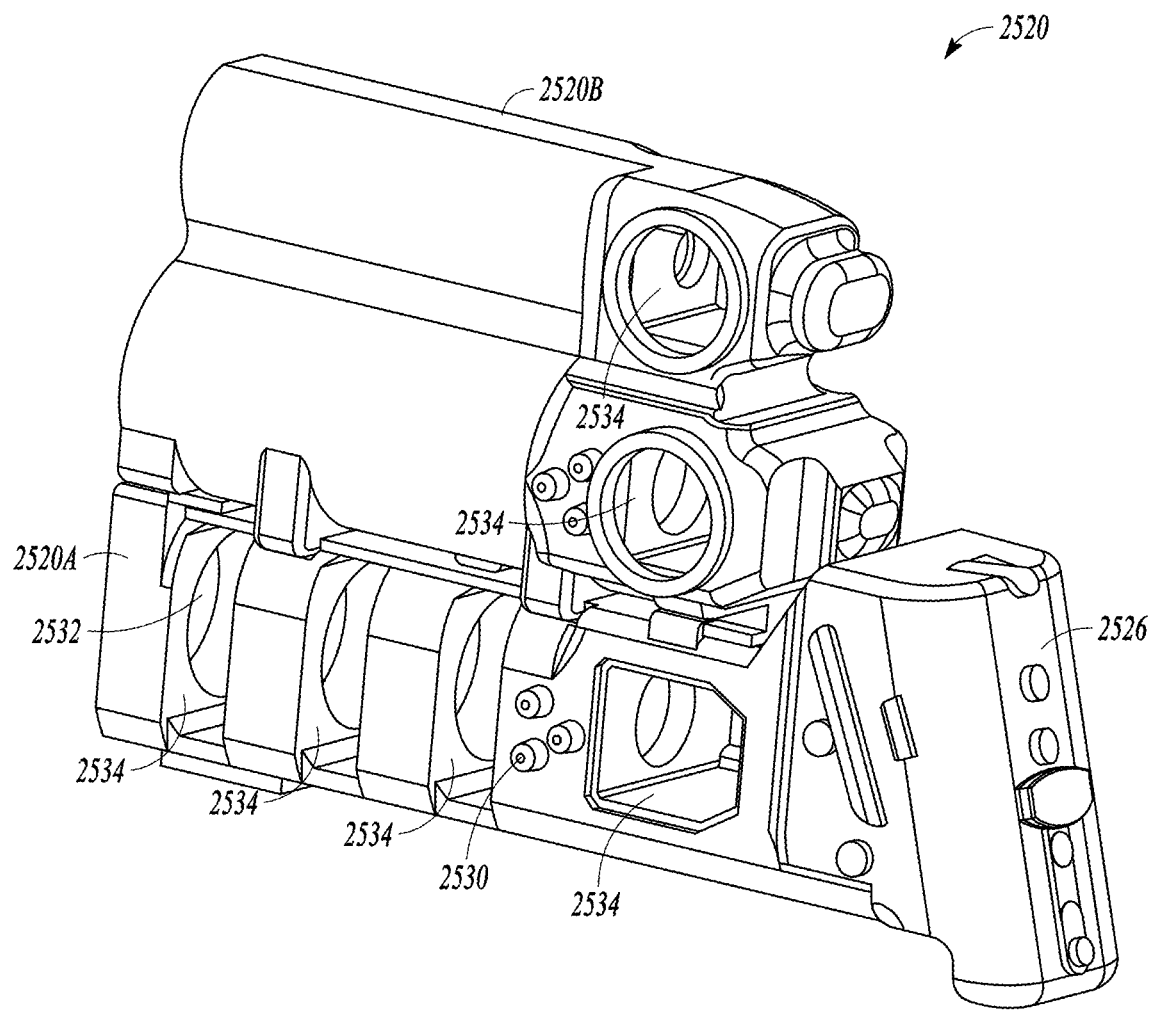
FIG. 26 shows a perspective view of an example header of an IMD according to an embodiment of the invention.
Figure 27:
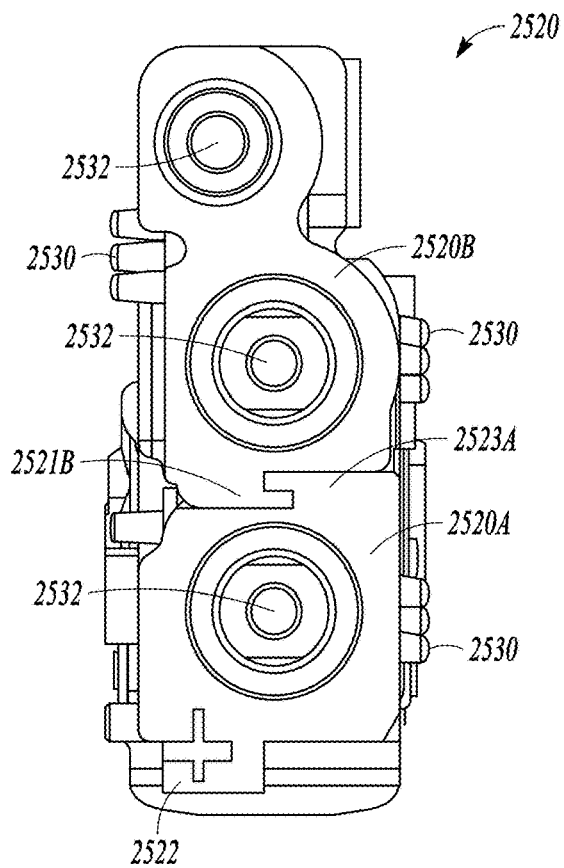
FIG. 27 shows a back view of an example header of an IMD according to an embodiment of the invention.

Referring to FIGS. 25-27, in some examples, a modular header core 2520 is shown. The header core 2520, in various examples, can be used in a header of an IMD similar to those described herein. That is, the header core 2520 can be used to attach and locate components of the IMD prior to molding of a header shell around the header core 2520 and attachment of the header to a device container of the IMD. In some examples, the header core 2520 can be used in place of the header cores described above and used in similar manners to those described above.

In some examples, the modular header core 2520 includes core modules 2520A, 2520B that can be selectively coupled together to form the header core 2520. In the example shown in the referenced figures, the header core 2520 includes two core modules 2520A, 2520B. In other examples, the header core 2520 can include more or less than two core modules, depending on the type of IMD in which the header core 2520 is to be used and the application of the IMD. In various examples, the core modules 2520A, 2520B can be detachably engaged with one another to form the header core 2520. For instance, the core module 2520A can include one or more engagement features 2523A configured to selectively couple to one or more complementary engagement features 2521B of the core module 2520B to engage the core modules 2520A, 2520B together. In some examples, the engagement features 2523A, 2521B provide sliding engagement between the core modules 2520A, 2520B. In some examples, the engagement features 2523A, 2521B include interlocking hooks configured to slidingly engage the core module 2520A with the core module 2520B. In some examples, the engagement features 2523A, 2521B engage with a friction fit in order to help maintain engagement of the core modules 2520A, 2520B.

In some examples, at least one of the core modules 2520A, 2520B includes a bore hole portion 2532. In further examples, at least one of the core modules 2520A, 2520B includes more than one bore hole portion 2532. The one or more bore holes portions 2532, in some examples, can be used to couple to components, such as leads. In some examples, at least one of the core modules 2520A, 2520B includes one or more cavities 2534 configured to accept one or more corresponding bore components, such bore components including, but not being limited to, a connector block, a seal ring, a tip connector, or the like. In various examples, the cavity 2534 can be formed through a side of the core module 2520A, 2520B of the header core 2520 and intersect the bore hole portion 2532, so that a bore component can be inserted into the cavity 2534 from the side of the header core 2520 and be placed in position within the bore hole portion 2532. Alternatively, some bore components can be placed through the bore hole portion 2532 and located in position within the core module 2520A, 2520B of the header core 2520. The bore components, for instance, electrical contacts and the like, can be configured to make electrical contact with a portion of the component (i.e., a terminal of the lead) inserted within the bore hole, in order to electrically couple the lead or other component with at least one electronic module within the device container of the IMD.

The one or more bore hole portions 2532 can be inspected to confirm proper geometry, location with respect to other bore hole portions 2532, and/or location within the head core 2520. Once some or all of the components are located within the header core 2520, the components of the header core 2520 can be tested to ensure proper placement within the bore hole portions 2532 and/or proper conductive functioning. By forming the bore hole portions 2532 prior to connection of the header with the device container, the header core 2520 and the bore hole portions 2532 can be tested and/or inspected prior to attachment of the header core 2520 to the device container. In the present examples of the modular header core 2520, not only can the header core 2520, as a whole be tested and inspected, but each of the core modules 2520A, 2520B can be tested and/or inspected. If one of the core modules 2520A, 2520B, is found to be defective in some manner, then only the defective core module 2520A, 2520B need be fixed or replaced.

As described herein with respect to FIGS. 23 and 24, various combinations of core modules can be used to form various header cores for use within various types of IMDs. In various examples, the core modules can be configured to each be capable of engaging with one another, such that different combinations of core modules can be engaged together to form different models of header cores. In this way, stocks of different core modules can be kept, rather than stocks of the different models of header cores, and the various core modules can be engaged in different combinations to form the various models of header cores needed for the various types of IMDs. In some examples, the core modules are configured to be engaged in any of a plurality of configurations. That is, the core modules can be stackable or otherwise engageable in various orders, sequences, or combinations to form a plurality of different header cores with the core modules. In other examples, the core modules are configured to be engaged in a particular configuration. That is, the core modules can be stackable or otherwise engageable in a particular order, sequence, or combination to form a particular header core with a combination of core modules.

Referring now to FIGS. 23-27, in some examples, a method of making an IMD including a modular header core 2320, 2520 is contemplated. In some examples, a plurality of core modules 2320A, 2320B, 2320C, 2520A, 2520B is selected for an IMD. In some examples, the plurality of core modules includes at least a first core module 2320A, 2520A and a second core module 2320B, 2520B. In further examples, the plurality of core modules includes at least a third core module 2520C. In further examples, the modular header core 2320, 2520 is formed by engaging the plurality of core modules 2320A, 2320B, 2320C, 2520A, 2520B with one another, as described herein. In another example, the modular header core 2320, 2520 is formed by slidingly engaging the plurality of core modules 2520A, 2520B with one another. In some examples, a header shell is formed around the modular header core 2320, 2520. In some examples, the header shell is molded around the modular header core 2320, 2520 in a manner similar to those described herein.

Figure 38:
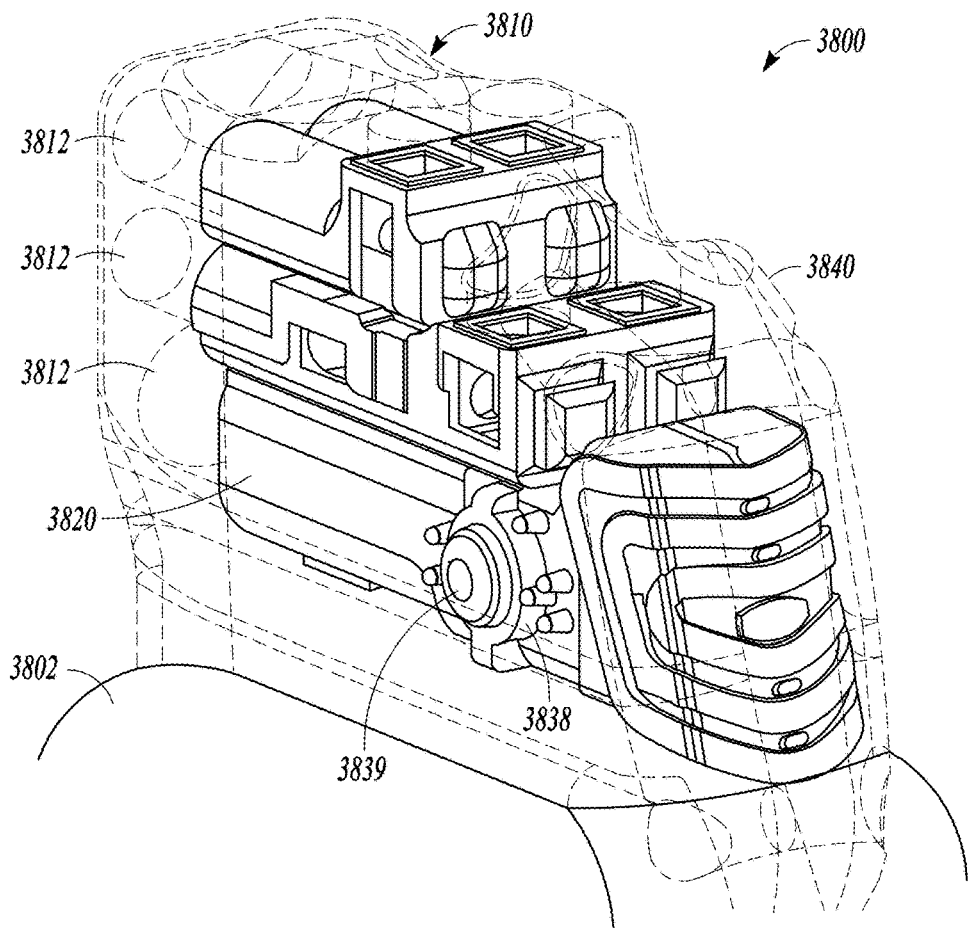
FIG. 38 shows a perspective view of an example header of an IMD according to an embodiment of the invention.
Figure 39:
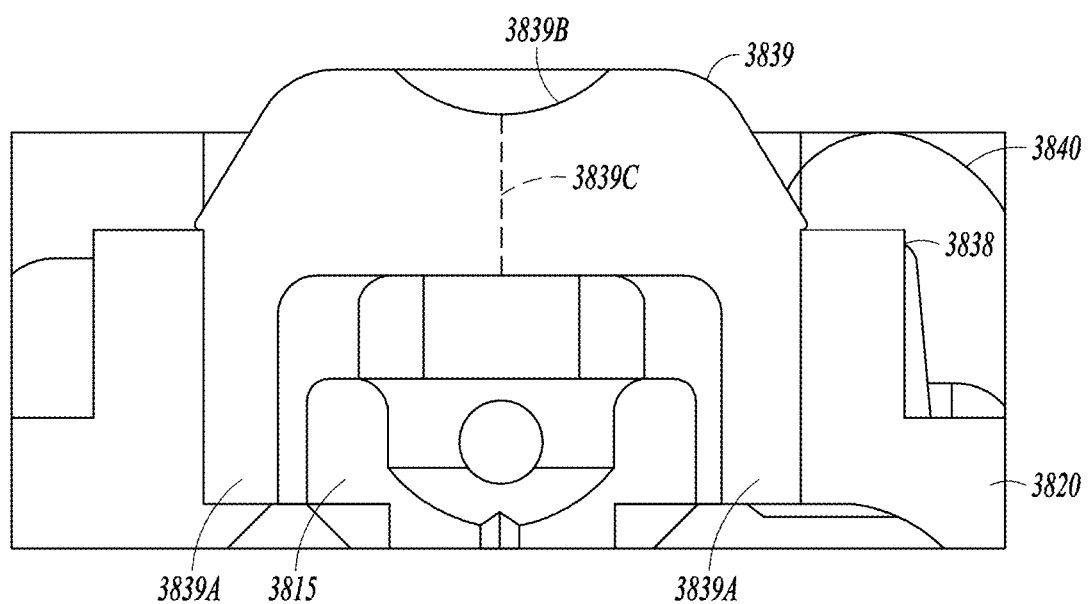
FIG. 39 shows a cut-away view of a seal plug of an example header of an IMD according to an embodiment of the invention.

Referring to FIGS. 38 and 39, in some examples, an IMD 3800 includes a header 3810 including a header core 3820 and a header shell 3840 disposed around the header core 3820. In various examples, the header 3810 includes one or more bore holes 3812. In some examples, as described above, the header core 3820 can be formed first and then attached to the device container 3802 by molding the header shell 3840 around the header core 3820 and to the device container 3802. Although shown in the presently-referenced figures as a modular header core 3820, it should be understood that, in various examples, the header core 3820 can include a modular header core, a partially modular header core, or a one-piece header core.

In some examples, the header 3810 includes a seal plug 3839 molded within the overmolded header shell 3840. The seal plug 3839, in some examples, is disposed within a seal plug receiver 3838 of the header core 3820. In some examples, the seal plug receiver 3838 includes a wall extending from a surface of the header core 3820. In various examples, the seal plug 3839 is configured to seal an area around a set screw 3815 (or other component of the IMD 3800). In some examples, the seal plug 3839 is configured to allow access to the set screw 3815 for adjustment (tightening or loosening) of the set screw 3815 with a torque wrench or other tool configured to adjust the set screw 3815. In some examples, the set screw 3815 can be tightened to help retain a lead within the bore hole 3812, for instance, by bearing upon a surface of the lead (or lead pin). In some examples, the seal plug 3839 includes a resilient seal portion 3839A configured to provide a compression fit within the seal plug receiver 3838 to seal around the set screw 3815. The seal plug 3839, in further examples, includes an exposed surface 3839B configured to be exposed after overmolding. The exposed surface 3839B, in some examples, can include a dimple or other feature configured to indicate a location of an aperture or other opening 3839C within the seal plug 3839. In various examples, the opening 3839C is configured to allow the torque wrench or other tool to be sealably inserted through the seal plug 3839 for engagement with the set screw 3815 therein to allow for adjustment of the set screw 3815. When the tool is removed, the opening 3839C is configured to sealably close (for instance, due to the resilient characteristics of the seal plug 3839). In this way, in various examples, the seal plug allows for sealing of the area of the set screw 3815 while still allowing access to the set screw 3815 for adjustment of the set screw 3815.

In some examples, the seal plug 3839 can be disposed in the seal plug receiver 3838 prior to overmolding of the header shell 3840 around the header core 3820. That is, the seal plug 3839 is compressibly disposed and retained within the seal plug receiver 3838 and then the header shell 3840 is overmolded around the header core 3820. The overmolding of the header shell 3840, in some examples, bears upon a portion of the seal plug 3839 to retain the seal plug 3839 in place within the seal plug receiver 3838. In further examples, the exposed surface 3839B of the seal plug 3839 remains exposed after overmolding to allow access with the tool, as described herein.

By providing the seal plug receiver 3838 and allowing overmolding of the header shell 3840 around the header core 3820 with the seal plug 3839 in place, the seal plug 3839 seals the area of the set screw 3815 or other component of the IMD 3800 and can eliminate steps involved with other ways of providing seal plugs in IMDs. For instance, the compressive seal created by the seal plug 3839 and the overmolding of the header shell 3840 allow for sealing and retention of the seal plug 3839 with respect to the header 3810 of the IMD 3800 without the need to use a separate sealant or structure machined or molded into the header configured to maintain the seal plug in place within the header. Additionally, the seal plug 3839 of the present examples allows for the overmolding of the header shell 3840 without the need for a mold structure to form a seal plug opening in the header configured to ultimately receive the seal plug after molding. In this way, by overmolding the header shell 3840 with the seal plug 3839 in place within the header core 3820, after completion of the overmolding and curing of the header shell 3840, the IMD 3800 can substantially be ready for use in that the IMD 3800 need not undergo further assembly steps to attach one or more seal plugs. Also, the configuration of the seal plug 3839 of the present examples allows for sealing of the seal plug 3839 within the seal plug receiver 3838 without the need for additional materials, such as a sealant or another material. That said, in other examples, it is contemplated that a sealant or other material can be used with the present seal plug 3839 in order to enhance the seal formed by the resilient seal portion 3839A of the seal plug 3839.

Figure 28:
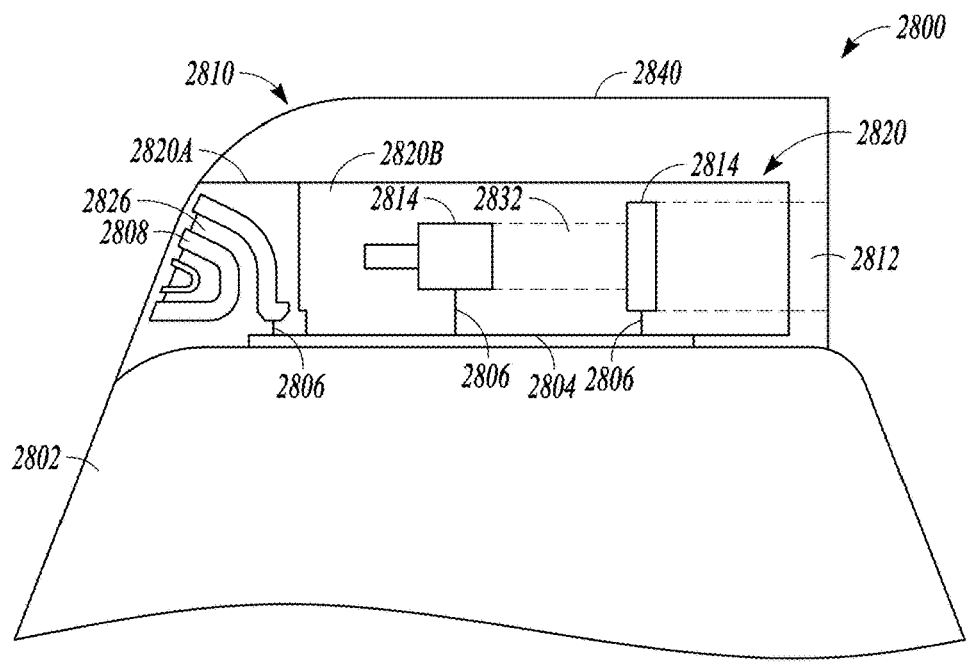
FIG. 28 shows a side view of an example header of an IMD according to an embodiment of the invention.
Figure 29:
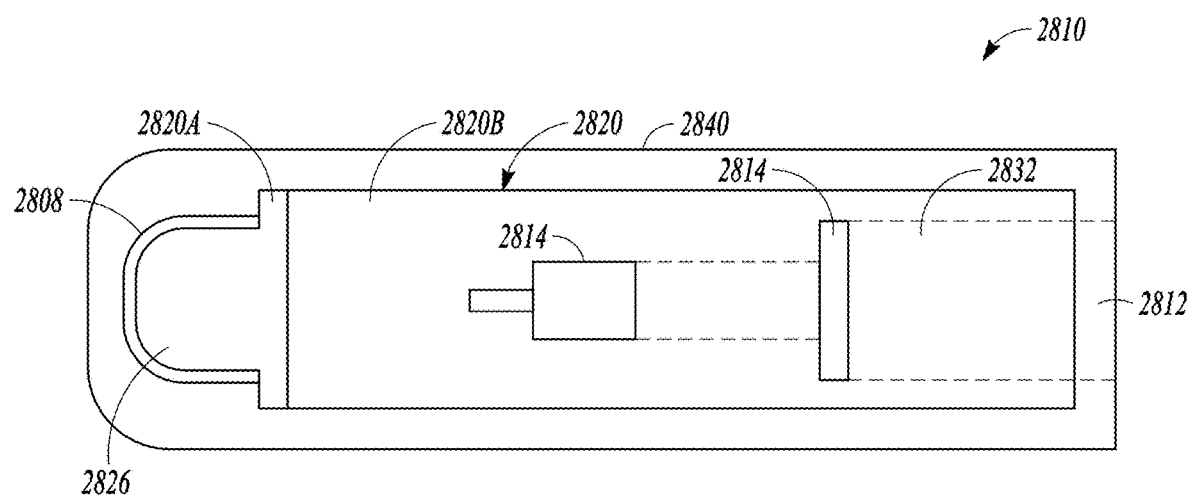
FIG. 29 shows a top view of an example header of an IMD according to an embodiment of the invention.

Referring now to FIGS. 28 and 29, in some examples, an IMD 2800 includes a device container 2802 including at least one electronic module within the device container 2802. In some examples, the IMD 2802 includes a header 2820 coupled to the device container 2802. In various examples, the header 2810 includes a header core 2820 and a header shell 2840 disposed around the header core 2820. In some examples, the header shell 2840 is attached to the device container 2802. In further examples, the header shell 2840 can be molded around the header core 2820 and molded to the device container 2802 in a similar manner to that described herein with respect to other examples. In still further examples, the header shell 2840 can be molded around the header core 2820 and attached to the device container 2802 using adhesive, welding, or the like. In some examples, the device container 2802 can include a textured surface for attachment of the header shell 2840 to the device container 2802, as described herein.

In further examples, the header 2810 includes an antenna 2808 coupled to the header 2810 and electrically coupled to the at least one electronic module within the device container 2802. In some examples, the antenna 2808 is coupled to the header core 2820 and molded within the header shell 2840. In further examples, the antenna 2808 is supported by an antenna attachment feature 2826 of the header core 2820, which, for instance, can be similar to one or more of the examples of antenna attachment features described herein. In an example, the antenna 2808 is electrically coupled to the at least one electronic module with a wire 2806.

In some examples, the header 2810 includes a first portion proximate the antenna 2808 and a second portion. In some examples, the first portion includes a first dielectric constant that is lower than a second dielectric constant of a second portion of the header 2810. Such a configuration can be beneficial to limit or otherwise decrease capacitive losses between the antenna 2808 and one or more other metallic or otherwise conductive components of the IMD 2800, such as, for instance, the device container 2802. In an example, the first portion of the header 2810 can be disposed at least substantially between the antenna 2808 and the device container 2802. Because capacitance is directly proportional to the dielectric constant, by controlling the first dielectric constant of the first portion between the antenna 2808 and the device container 2802, the capacitance between the antenna 2808 and the device container 2802 can be controlled, thereby controlling capacitive loss and, therefore, signal loss of the antenna 2808. In further examples, the first portion with the lower dielectric constant can be disposed substantially between the antenna 2808 and other conductive components of the IMD 2800, such as, for instance, the one or more electrical contacts 2814, to limit capacitive losses between the antenna 2808 and other conductive components.

In some examples, the first portion of the header 2810 includes the antenna attachment feature 2826. In some examples, the antenna attachment feature 2826 is engaged with the header core 2820. In other examples, the antenna attachment feature 2826 is integrally formed with the header core 2820. The first portion of the header 2810, in some examples, includes the header core 2820, and the second portion of the header 2810 includes the header shell 2840, such that the header core 2820 is formed from a material that includes a lower dielectric constant than that of a material from which the header shell 2840 is formed.

In other examples, the first portion of the header 2810 includes a first portion 2820A of the header core 2820 and the second portion of the header 2810 includes a second portion 2820B of the header core 2820, wherein the first portion 2820A includes a lower dielectric constant than that of the second portion 2820B. In this example, the header core 2820 can include the first portion 2820A and the second portion 2820B. In further examples, the first portion 2820A of the header core 2820 can include the antenna attachment feature 2826. In a further example, the first portion 2820A and the second portion 2820B can be molded together. That is, the header core 2820 can be formed in a two-stage molding operation, with one of the first portion 2820A or the second portion 2820B being formed with a first molding operation and the other of the first portion 2820A or the second portion 2820B being formed with a second molding operation. In further examples, the second molding operation engages the first portion 2820A with the second portion 2820B. In another example, the first portion 2820A is mechanically attached to the second portion 2820B. For instance, the first and second portions 2820A, 2820B can include complementary engaging features to allow engagement of at least the first and second portions 2820A, 2820B to form the header core 2820. In some examples, the first and second portions 2820A, 2820B of the header core 2820 can be similar to the core modules of the modular header core examples described above. In other examples, the first and second portions 2820A, 2820B can be attached using a fastening substance, such as, for instance, a medical adhesive or the like.

In various examples, the dielectric properties of the first portion of the header 2810 can be achieved in different ways. For instance, in an example, the first portion can be formed from a specialized material chosen for its particular dielectric properties. For instance, a material can be chosen for the first portion that includes a dielectric constant that is less than that of the material from which the second portion of the header 2810 is formed.

In other examples, the first portion can be formed from an aerated material. That is, in various examples, air or another gas can be bubbled through a material, for instance, during molding of the first portion of the header 2810 to create air or other gas bubbles in the first portion of the header 2810 and make an aerated material or an aerated foam. Because air has a relatively low dielectric constant (slightly greater than one), the dielectric of the aerated material is a function of the dielectric constants of the material and of air. Because air has a lower dielectric constant than the material being aerated, the inclusion of air bubbles within the material lowers the overall dielectric constant of the aerated material. The proportion of the material to air determines the overall dielectric constant of the aerated material. The higher the proportion of air in the aerated material, the lower the overall dielectric constant is as compared to the dielectric constant of the unaerated material. Other gases, or mixtures of gases, can be used in other examples in much the same manner, provided the gases are capable of being implanted within the body and provided the gases do not react adversely when put in contact with the material to be aerated or other materials of the IMD 2800.

In other examples, the first portion can be formed by mixing a low dielectric constant material with mold material. In these examples, the low dielectric constant material need only have a dielectric constant that is lower than that of the mold material, such that the mixture of the low dielectric constant material and the mold material includes a lower overall dielectric constant than does the mold material alone. In some examples, a low dielectric constant solid material can be mixed with the mold material to form a solid emulsion, which ultimately forms a solid filled material with curing of the mold material. In some examples, the low dielectric constant material includes expanded polytetrafluoroethylene (ePTFE). In still other examples, the low dielectric constant material includes aerated or porous glass. In other examples, the low dielectric constant material can include a liquid.

By placing the lower dielectric constant material in a position within the IMD 2800 substantially between the antenna 2808 and the device container 2802 and/or other conductive components within or proximate the IMD 2800, the capacitive loss between the antenna 2808 and the device container 2802 and/or other conductive components within or proximate the IMD 2800 can be decreased from the capacitive loss that would have occurred if a material without a lower dielectric constant. Other conductive components can include the electrical contacts 2814 (including a connector block, a seal ring, a tip connector, or the like), the wires 2806, or the like. By doing so, signal losses from the antenna 2808 can be decreased. Decreased signal losses can lead to a better transmission range for the antenna 2808 and/or lower power operation of the antenna 2808, among other things.

In examples of the header 2810 including a low dielectric portion in which the low dielectric portion is formed by aerating the material from which the low dielectric portion is formed, in some examples, there exists the possibility that the one or more bubbles, voids, pockets, or other spaces in the material could start filling with fluid after implantation within the body due to saturation of the material and/or materials of the header 2810 over time. In various examples, the low dielectric portion of the header 2810 can include a moisture shield, coating, or the like to decrease the likelihood that moisture will accumulate within the one or more bubbles, voids, pockets, or other spaces within the low dielectric portion of the header 2810. One reason for inhibiting the accumulation of moisture within the one or more bubbles, voids, pockets, or other spaces is because body fluid has a relatively high dielectric constant, thereby increasing the overall dielectric constant of the portion of the header 2810, potentially leading to higher capacitive losses between the antenna 2808 and the device container 2802 and increased signal loss. In some examples, the moisture shield or coating can be formed by at least partially coating the low dielectric portion of the header 2810 with a moisture barrier, such as a polymeric material. In some examples, Parylene can be used to form the moisture barrier.

In some examples, the header core 2820 is formed by molding. In further examples, the header core 2820 is positioned with respect to the device container 2802, any connections are made between the header core 2820 and the device container 2802, and the header shell 2840 is then molded around the header shell 2820 and attached to the device container 2802. Examples of such overmolding of the header shell are described herein, and the overmolding of the header shell 2840 of the present examples can be similar to such described examples. However, in some examples, molding of the low dielectric portion of the header 2810 using an aerated material can lead to bubbles, voids, or the like forming at a surface of the molded portion. Such surface voids can lead to mold inconsistencies, defects, or the like. As such, in some examples, the minimization of such surface voids can be desirable. In some examples, surface voids in the low dielectric portion can be decreased by first filling a mold for the low dielectric portion with an unaerated material, then draining the material from the mold. By doing so, interior surfaces of the mold are wetted to form a coating over the interior surfaces of the mold. The mold can then be filled with the aerated material to form the low dielectric portion. Because the interior surfaces of the mold were coated with the unaerated material prior to filling the mold with the aerated material, the likelihood of surface voids being formed in the low dielectric portion can be decreased.

Figure 30:
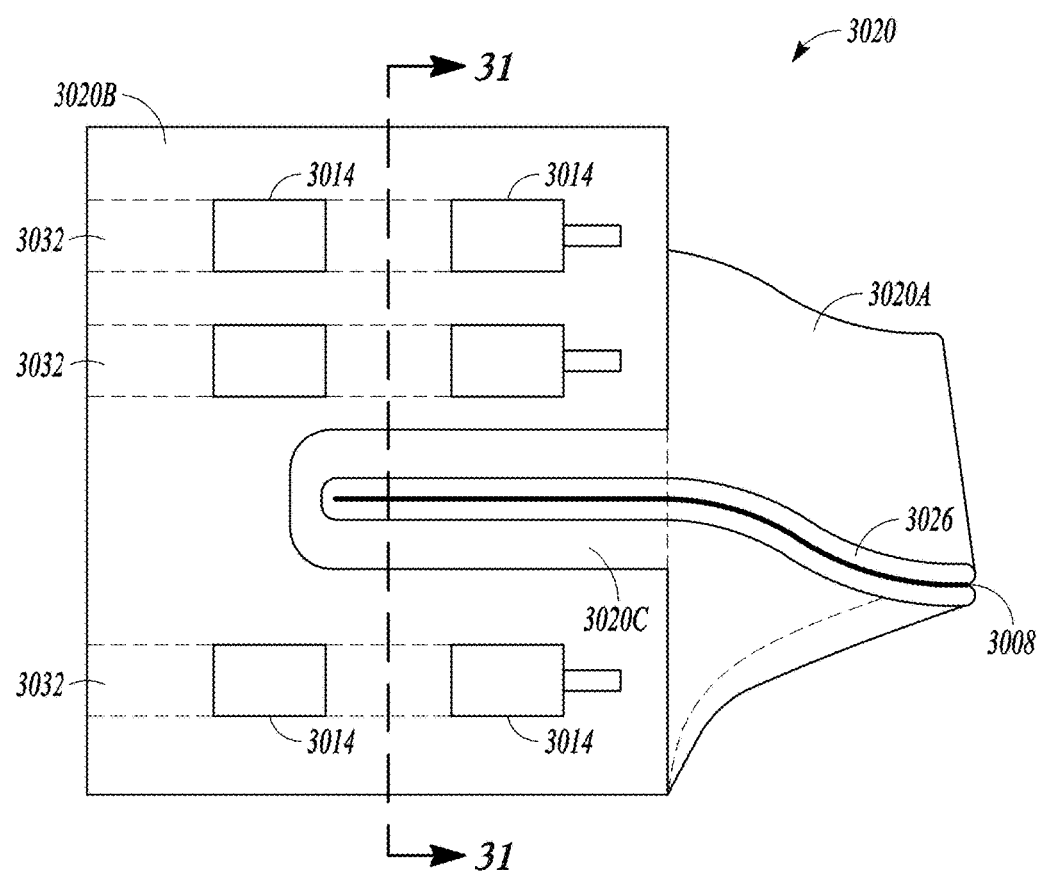
FIG. 30 shows a side view of an example header core of an IMD according to an embodiment of the invention.
Figure 31:
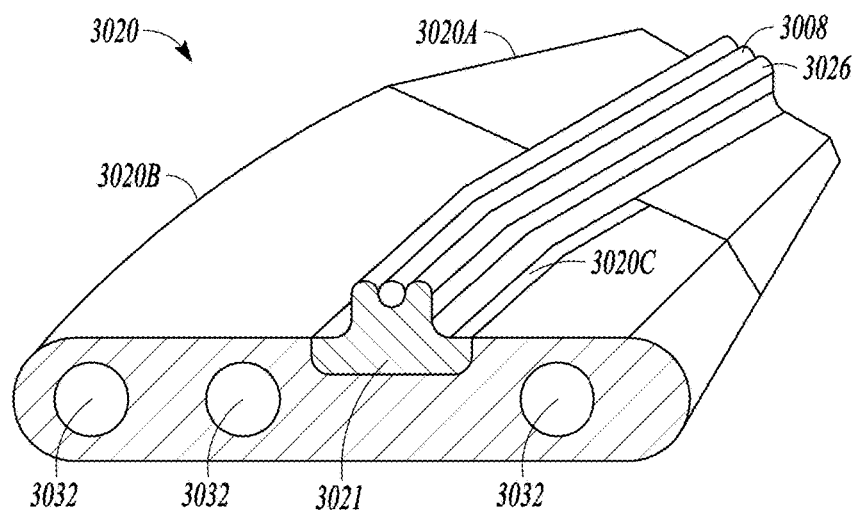
FIG. 31 shows a cross-sectional view of the example header core, the cross section taken along line 31-31 of FIG. 30.

Referring to FIGS. 30 and 31, in some examples, a header core 3020 of an IMD includes a first portion 3020A including a material including a relatively low dielectric constant and a second portion 3020B attached to the first portion 3020A. Various aspects of the example shown in FIGS. 30 and 31 can be similar to those described herein with respect to the header 2810, including the materials used to form the header 2810 and the methods of forming the header 2810. As such, at least portions of the description are applicable to the presently-referenced header core 3020. In some examples, the header core 3020 includes an antenna attachment feature 3026 configured to support, locate, or otherwise position an antenna 3008 with respect to the header core 3020 and, ultimately, with respect to a device container of an IMD to which the header core 3020 is attached. In some examples, the antenna attachment feature 3026 includes a channel configured to capture the antenna 3008 along at least a portion of the antenna 3008. In some examples, the first portion 3020A of the header core 3020 can be formed from a material having a relatively low dielectric constant. In some examples, the first portion 3020A is disposed substantially between the antenna 3008 and conductive components of the IMD, such as one or more electrical contacts 3014 of one or more bore hole portions 3032 the header core 3020 (including a connector block, a seal ring, a tip connector, or the like), wires of the IMD, a device container of the IMD, or the like. Due to the geometry of the antenna 3008, in some examples, the first portion 3020 extends along a side of the header core 3020 and around a front of the header core 3020. The first portion 3020A, in an example, includes a leg 3020C that extends along one side of the header core 3020 to accommodate the geometry of the antenna 3008. In some examples, the leg 3020C is integrally formed with the first portion 3020A. In other examples, the leg 3020C can be a separate piece from the rest of the first portion 3020A that is separately attached to the header core 3020.

In some examples, the first portion 3020A is mechanically attached to the second portion 3020B, for instance, using complementary engaging features. In some examples, the first portion 3020A is mechanically attached to the second portion 3020B, for instance, using an adhesive either alone or in addition to complementary engaging features. In examples in which the leg 3020C is separately formed from the rest of the first portion 3020A, the leg 3020C can include an adhesive strip that can be mounted to an outer surface of the second portion 3020B at a selected position to accommodate the antenna 3008. In further examples, the outer surface of the second portion 3020B can include a channel 3021 within which the leg 3020C can be disposed. In such examples, the leg 3020C, whether separate from or integral with the rest of the first portion 3020A, can be retained within the channel 3021 using mechanical complementary engaging features, a friction fit, and/or adhesive. In some examples, the first and second portions 3020A, 3020B (and the leg 3020C, if separately formed from the first portion 3020A) are engaged to one another in manners similar to those described herein with respect to the modular header core examples.

Additional Notes and Examples

Example 1 can include subject matter (such as an apparatus, a method, a means for performing acts) that can include or can use an implantable device. The implantable device can include a metallic device container. The implantable device can include a textured surface on a portion of the metallic device container, having an area root mean square value between 3.05 μm and 10.2 μm. The implantable device can include a thermoset polymer header forming an interface with at least a portion of the textured surface.

Example 2 can include or use, or can optionally be combined with the subject matter of Example 1 to include or use an implantable device, wherein the textured surface includes a laser treated surface including a number of substantially spherical particles.

Example 3 can include or use, or can optionally be combined with the subject matter of Examples 1-2 to include or use an implantable device, wherein the thermoset polymer is an epoxy.

Example 4 can include or use, or can optionally be combined with the subject matter of Examples 1-3 to include or use an implantable device, wherein the epoxy header is cast in place.

Example 5 can include or use, or can optionally be combined with the subject matter of Examples 1-4 to include or use an implantable device, wherein the epoxy header is injection molded in place.

Example 6 can include or use, or can optionally be combined with the subject matter of Examples 1-5 to include or use an implantable device, wherein the textured surface has an area root mean square value between 3.81 μm and 8.89 μm.

Example 7 can include or use, or can optionally be combined with the subject matter of Examples 1-6 to include or use an implantable device, wherein the textured surface has an area root mean square value between 3.30 μm and 3.81 μm.

Example 8 can include or use, or can optionally be combined with the subject matter of Examples 1-7 to include or use an implantable device, wherein the epoxy header has a Shore D hardness between approximately 80 and 90.

Example 9 can include or use, or can optionally be combined with the subject matter of Examples 1-8 to include or use an implantable device, wherein a volume fraction of resin to hardener in the epoxy is approximately 2 to 1.

Example 10 can include or use, or can optionally be combined with the subject matter of Examples 1-9 to include or use an implantable device, wherein the laser treated surface includes a periodic pattern.

Example 11 can include or use, or can optionally be combined with the subject matter of Examples 1-10 to include or use an implantable device, wherein the laser treated surface includes at least one pattern of ridges and troughs.

Example 12 can include or use, or can optionally be combined with the subject matter of Examples 1-11 to include or use an implantable device, wherein the epoxy header is substantially transparent.

Example 13 can include or use, or can optionally be combined with the subject matter of Examples 1-12 to include or use an implantable device, wherein the epoxy header has a glass transition of approximately 70 degrees C.

Example 14 can include or use, or can optionally be combined with the subject matter of Examples 1-13 to include or use an implantable device, wherein, in side load testing, the thermoset polymer header fails in the bulk for a metallic device container thickness between 16 mm and 4 mm.

Example 15 can include or use, or can optionally be combined with the subject matter of Examples 1-14 to include or use an implantable device, wherein, in side load testing, the thermoset polymer header fails in the bulk for a metallic device container thickness between 14 mm and 6 mm.

Example 16 can include or use, or can optionally be combined with the subject matter of Examples 1-15 to include or use an implantable device, wherein, in side load testing, the thermoset polymer header fails in the bulk for a metallic device container thickness between 12 mm and 8 mm.

Example 17 can include or use, or can optionally be combined with the subject matter of Examples 1-16 to include or use a method. The method can include texturing an interface surface of an implantable device container. The method can also include raising a temperature of an epoxy resin to lower its viscosity. The method can also include injecting a mixture of the epoxy resin and a hardener in a contained space to contact the interface surface of the implantable device container. The method can also include driving the mixture to a first temperature for a first amount of time. The method can also include driving the mixture to a second temperature to at least partially cure the mixture.

Example 18 can include or use, or can optionally be combined with the subject matter of Examples 1-17 to include or use a method, wherein raising the temperature of an epoxy resin to lower its viscosity includes raising a temperature to approximately 50° C.

Example 19 can include or use, or can optionally be combined with the subject matter of Examples 1-18 to include or use a method, wherein injecting the mixture includes injecting at a pressure of less than 0.034 MPa.

Example 20 can include or use, or can optionally be combined with the subject matter of Examples 1-19 to include or use a method, wherein injecting the mixture further includes injecting into a mold that is pre-heated to approximately 50° C.

Example 21 can include or use, or can optionally be combined with the subject matter of Examples 1-20 to include or use a method, wherein driving the mixture to a first temperature includes driving the mixture to between approximately 25° C. and 55° C. for a duration of approximately 40 minutes.

Example 22 can include or use, or can optionally be combined with the subject matter of Examples 1-21 to include or use a method, wherein driving the mixture to a second temperature includes driving the mixture to a temperature of approximately 85° C. for approximately 10 minutes.

Example 23 can include or use, or can optionally be combined with the subject matter of Examples 1-22 to include or use a method, wherein texturing the interface surface includes particle blasting.

Example 24 can include or use, or can optionally be combined with the subject matter of Examples 1-23 to include or use a method, wherein texturing the interface surface includes laser treating.

Example 25 can include or use, or can optionally be combined with the subject matter of Examples 1-24 to include or use a method, wherein laser treating the interface surface includes laser treating a textured surface having an area root mean square value between 3.05 μm and 10.2 μm.

Example 26 can include or use, or can optionally be combined with the subject matter of Examples 1-25 to include or use a method, wherein laser treating the interface surface includes laser treating a textured surface having an area root mean square value between 3.81 μm and 8.89 μm.

Example 27 can include or use, or can optionally be combined with the subject matter of Examples 1-26 to include or use a method, wherein laser treating the interface surface includes laser treating a textured surface having an area root mean square value between 3.30 μm and 3.81 μm.

Example 28 can include, or can be combined with the subject matter of one or any combination of Examples 1-27 to optionally include, subject matter (such as an apparatus, such as an implantable medical device, a method, a means for performing acts, or a machine-readable medium including instructions that, when performed by the machine, cause the machine to perform acts) that can comprise: a device container including an electronic module within the device container; a header core including an electronic connection feature electrically coupled to the electronic module within the device container, the electronic connection feature configured to engage with a lead, the header core including a tag holder; an identification tag engaged with the tag holder, the tag holder configured to locate the identification tag in a selected position with respect to the header core; and a molded header shell disposed around the header core and attached to the device container.

Example 29 can include or use, or can optionally be combined with the subject matter of Examples 1-28 to include or use an implantable medical device, wherein the identification tag is configured to be x-ray readable.

Example 30 can include or use, or can optionally be combined with the subject matter of Examples 1-29 to include or use an implantable medical device, wherein the identification tag includes tungsten.

Example 31 can include or use, or can optionally be combined with the subject matter of Examples 1-30 to include or use an implantable medical device, wherein the tag holder includes a slot in the header core configured to engage with a portion of the identification tag.

Example 32 can include or use, or can optionally be combined with the subject matter of Examples 1-31 to include or use an implantable medical device, wherein the tag holder includes: a first slot in the header core configured to engage with a portion of the identification tag; and a second slot in the header core substantially perpendicular to the first slot.

Example 33 can include or use, or can optionally be combined with the subject matter of Examples 1-32 to include or use an implantable medical device, wherein the identification tag includes a post configured to engage with the tag holder of the header core.

Example 34 can include or use, or can optionally be combined with the subject matter of Examples 1-33 to include or use an implantable medical device, wherein the post of the identification tag includes an indexing feature configured to position and maintain the identification tag in a selected orientation with respect to the header core.

Example 35 can include or use, or can optionally be combined with the subject matter of Examples 1-34 to include or use an implantable medical device, wherein the tag holder includes a surface of the header core, and the identification tag is printed on the surface of the header core.

Example 36 can include or use, or can optionally be combined with the subject matter of Examples 1-35 to include or use an implantable medical device, wherein the header core is formed from a first material and the header shell is formed from a second material, the first material being different from the second material.

Example 37 can include or use, or can optionally be combined with the subject matter of Examples 1-36 to include or use an implantable medical device, wherein the header core is configured to inhibit mold defects in the header shell.

Example 38 can include, or can be combined with the subject matter of one or any combination of Examples 1-37 to optionally include, subject matter (such as an apparatus, such as an implantable medical device, a method, a means for performing acts, or a machine-readable medium including instructions that, when performed by the machine, cause the machine to perform acts) that can comprise: a device container including an electronic module within the device container; a header core including an antenna attachment feature; an antenna engaged with the antenna attachment feature and electrically coupled with the electronic module within the device container, the antenna attachment feature configured to locate the antenna in a selected position with respect to the header core; and a molded header shell disposed around the header core and attached to the device container, the header shell disposed around and configured to retain the antenna in the selected position.

Example 39 can include or use, or can optionally be combined with the subject matter of Examples 1-38 to include or use an implantable medical device, wherein the antenna attachment feature includes ridges spaced to accommodate the antenna between the ridges.

Example 40 can include or use, or can optionally be combined with the subject matter of Examples 1-39 to include or use an implantable medical device, wherein one or more of the ridges of the antenna attachment feature are disposed between portions of the antenna and are configured to maintain spacing between the portions of the antenna.

Example 41 can include or use, or can optionally be combined with the subject matter of Examples 1-40 to include or use an implantable medical device, wherein the antenna attachment feature includes a retention feature configured to grip at least a portion of the antenna.

Example 42 can include or use, or can optionally be combined with the subject matter of Examples 1-41 to include or use an implantable medical device, wherein the retention feature is configured to frictionally retain at least the portion of the antenna.

Example 43 can include or use, or can optionally be combined with the subject matter of Examples 1-42 to include or use an implantable medical device, wherein the antenna attachment feature is configured to maintain a substantially constant distance between the antenna and a patient.

Example 44 can include or use, or can optionally be combined with the subject matter of Examples 1-43 to include or use an implantable medical device, wherein the antenna attachment feature includes a removable portion configured to detachably engage with the header core.

Example 45 can include or use, or can optionally be combined with the subject matter of Examples 1-44 to include or use an implantable medical device, wherein the antenna attachment feature includes a channel.

Example 46 can include or use, or can optionally be combined with the subject matter of Examples 1-45 to include or use an implantable medical device, wherein the channel includes one or more portions configured to be crimped to retain the antenna within the channel.

Example 47 can include or use, or can optionally be combined with the subject matter of Examples 1-46 to include or use an implantable medical device, wherein the antenna includes a printed antenna disposed on the antenna attachment feature of the header core.

Example 48 can include or use, or can optionally be combined with the subject matter of Examples 1-47 to include or use an implantable medical device, wherein the header core is formed from a first material and the header shell is formed from a second material, the first material being different from the second material.

Example 49 can include or use, or can optionally be combined with the subject matter of Examples 1-48 to include or use an implantable medical device, wherein the header core is configured to inhibit mold defects in the header shell.

Example 50 can include, or can be combined with the subject matter of one or any combination of Examples 1-49 to optionally include, subject matter (such as an apparatus, such as an implantable medical device, a method, a means for performing acts, or a machine-readable medium including instructions that, when performed by the machine, cause the machine to perform acts) that can comprise: a device container including an electronic module within the device container; a header core including a bore hole portion and at least two electronic connection features disposed within the bore hole portion, the bore hole portion including at least one cavity configured to allow placement of at least one of the electronic connection features within the bore hole portion, the at least two electronic connection features being electrically coupled to the electronic module within the device container, the at least two electronic connection features being configured to engage with a lead disposed within the bore hole portion, wherein the header core is configured to allow location of the at least two electronic connection features in a selected configuration within the bore hole portion; and a header shell disposed around the header core and attached to the device container.

Example 51 can include or use, or can optionally be combined with the subject matter of Examples 1-50 to include or use an implantable medical device, wherein the header shell is molded around the header core.

Example 52 can include or use, or can optionally be combined with the subject matter of Examples 1-51 to include or use an implantable medical device, wherein at least one of the electronic connection features is sealed within the cavity of the header core.

Example 53 can include or use, or can optionally be combined with the subject matter of Examples 1-52 to include or use an implantable medical device, comprising a wire electrically coupling the electronic connection feature to the electronic module within the device container, wherein the header core includes a locating feature configured to maintain the wire in a selected position with respect to the header core.

Example 54 can include or use, or can optionally be combined with the subject matter of Examples 1-53 to include or use an implantable medical device, wherein the header core includes a standoff configured to position the header core in a selected position with respect to the device container.

Example 55 can include or use, or can optionally be combined with the subject matter of Examples 1-54 to include or use an implantable medical device, wherein the header core includes a material relief configured to inhibit delamination of the header shell.

Example 56 can include or use, or can optionally be combined with the subject matter of Examples 1-55 to include or use an implantable medical device, wherein the header core and the header shell are formed from the same material.

Example 57 can include or use, or can optionally be combined with the subject matter of Examples 1-56 to include or use an implantable medical device, wherein the header core is formed from a first material and the header shell is formed from a second material.

Example 58 can include or use, or can optionally be combined with the subject matter of Examples 1-57 to include or use an implantable medical device, comprising a seal plug disposed within a receiver of the header core and at least partially retained within the receiver by the header shell, the seal plug configured to sealingly allow access through the seal plug.

Example 59 can include or use, or can optionally be combined with the subject matter of Examples 1-58 to include or use an implantable medical device, wherein the seal plug is configured to sealingly allow access to a set screw of the header core.

Example 60 can include or use, or can optionally be combined with the subject matter of Examples 1-59 to include or use an implantable medical device, wherein the header shell is molded over a portion of the seal plug to at least partially retain the seal plug within the receiver of the header core.

Example 61 can include, or can be combined with the subject matter of one or any combination of Examples 1-60 to optionally include, subject matter (such as an apparatus, such as an implantable medical device, a method, a means for performing acts, or a machine-readable medium including instructions that, when performed by the machine, cause the machine to perform acts) that can comprise: forming a header core, the header core including a bore hole portion, the bore hole portion including at least one cavity configured to allow placement of an electronic connection feature within the bore hole portion, the electronic connection feature configured to engage with a lead disposed within the bore hole portion; inspecting the bore hole portion prior to attachment of the header core with a device container; attaching the header core to the device container; and forming a header shell around the header core and at least a portion of the device container.

Example 62 can include or use, or can optionally be combined with the subject matter of Examples 1-61 to include or use a method, wherein inspecting the header core includes verifying geometry and location of the bore hole portion.

Example 63 can include or use, or can optionally be combined with the subject matter of Examples 1-62 to include or use a method, wherein inspecting the header core includes electrically testing the electronic connection feature within the bore hole portion.

Example 64 can include or use, or can optionally be combined with the subject matter of Examples 1-63 to include or use a method, wherein forming the header core includes sealing the electronic connection feature within the cavity.

Example 65 can include or use, or can optionally be combined with the subject matter of Examples 1-64 to include or use a method, wherein sealing the electronic connection feature within the cavity includes induction heating the header core to seal the electronic connection feature within the cavity.

Example 66 can include or use, or can optionally be combined with the subject matter of Examples 1-65 to include or use a method, wherein sealing the electronic connection feature within the cavity includes laser heating the header core to seal the electronic connection feature within the cavity.

Example 67 can include or use, or can optionally be combined with the subject matter of Examples 1-66 to include or use a method, wherein sealing the electronic connection feature within the cavity includes using an adhesive to seal the electronic connection feature within the cavity.

Example 68 can include or use, or can optionally be combined with the subject matter of Examples 1-67 to include or use a method, wherein forming the header shell includes molding the header shell around the header core, wherein the electronic connection feature sealed within the cavity inhibits mold material from entering the cavity or the bore hole portion during molding of the header shell.

Example 69 can include or use, or can optionally be combined with the subject matter of Examples 1-68 to include or use a method, wherein forming the header core includes forming a locating feature in the header core, the locating feature configured to maintain a wire in a selected location with respect to the header core.

Example 70 can include or use, or can optionally be combined with the subject matter of Examples 1-69 to include or use a method, comprising bending one or more wires from the device container into one or more selected positions configured for attachment to the header core, wherein attaching the header core to the device container includes attaching at least one of the wires to the electronic connection feature.

Example 71 can include or use, or can optionally be combined with the subject matter of Examples 1-70 to include or use a method, wherein bending the one or more wires includes using a template to bend the one or more wires into the one or more selected positions configured for attachment to the header core.

Example 72 can include or use, or can optionally be combined with the subject matter of Examples 1-71 to include or use a method, wherein bending the one or more wires includes using a bending tool to bend the one or more wires into the one or more selected positions configured for attachment to the header core.

Example 73 can include or use, or can optionally be combined with the subject matter of Examples 1-72 to include or use a method, wherein forming the header shell includes molding the header shell around the header core.

Example 74 can include or use, or can optionally be combined with the subject matter of Examples 1-73 to include or use a method, wherein molding includes using a mold apparatus configured to reduce flashing present on the header shell.

Example 75 can include or use, or can optionally be combined with the subject matter of Examples 1-74 to include or use a method, wherein molding includes using a mold apparatus configured to reduce flashing present on the header shell proximate to one or more bore holes.

Example 76 can include or use, or can optionally be combined with the subject matter of Examples 1-75 to include or use a method, comprising disposing a seal plug within a receiver of the header core, the seal plug configured to sealingly allow access through the seal plug.

Example 77 can include or use, or can optionally be combined with the subject matter of Examples 1-76 to include or use a method, wherein forming the header shell includes forming the header shell over a portion of the seal plug to at least partially retain the seal plug within the receiver of the header core.

Example 78 can include, or can be combined with the subject matter of one or any combination of Examples 1-77 to optionally include, subject matter (such as an apparatus, such as an implantable medical device, a method, a means for performing acts, or a machine-readable medium including instructions that, when performed by the machine, cause the machine to perform acts) that can comprise: a device container including an electronic module within the device container; a modular header core including: a first core module including a first bore hole portion of a first bore hole, the first bore hole portion configured to couple a first electrical component with the electronic module; and a second core module including a second bore hole portion of a second bore hole different than the first bore hole, the second bore hole portion configured to couple a second electrical component with the electronic module, wherein the first core module is detachably engaged with the second core module; and a header shell disposed around the modular header core and attached to the device container.

Example 79 can include or use, or can optionally be combined with the subject matter of Examples 1-78 to include or use an implantable medical device, wherein the first core module includes a first electronic connection feature electrically coupled to the electronic module within the device container, the first electronic connection feature configured to engage with the first electrical component.

Example 80 can include or use, or can optionally be combined with the subject matter of Examples 1-79 to include or use an implantable medical device, wherein the second core module includes a second electronic connection feature electrically coupled to the electronic module within the device container, the second electronic connection feature configured to engage with the second electrical component.

Example 81 can include or use, or can optionally be combined with the subject matter of Examples 1-80 to include or use an implantable medical device, wherein the first core module is frictionally engaged with the second core module.

Example 82 can include or use, or can optionally be combined with the subject matter of Examples 1-81 to include or use an implantable medical device, wherein the first core module is slidingly coupled with the second core module.

Example 83 can include or use, or can optionally be combined with the subject matter of Examples 1-82 to include or use an implantable medical device, wherein the header shell and the modular header core are formed from a first material.

Example 84 can include or use, or can optionally be combined with the subject matter of Examples 1-83 to include or use an implantable medical device, wherein the header shell is formed from a first material and the modular header core is formed from a second material.

Example 85 can include or use, or can optionally be combined with the subject matter of Examples 1-84 to include or use an implantable medical device, wherein the header shell is molded around the modular header core.

Example 86 can include, or can be combined with the subject matter of one or any combination of Examples 1-85 to optionally include, subject matter (such as an apparatus, such as an implantable medical device, a method, a means for performing acts, or a machine-readable medium including instructions that, when performed by the machine, cause the machine to perform acts) that can comprise: selecting a plurality of core modules for an implantable medical device, the plurality of core modules being selected according to the application of the implantable medical device; forming a modular header core including engaging the plurality of core modules with one another; and forming a header shell around the modular header core.

Example 87 can include or use, or can optionally be combined with the subject matter of Examples 1-86 to include or use a method, wherein selecting the plurality of core modules includes selecting at least a first core module and a second core module.

Example 88 can include or use, or can optionally be combined with the subject matter of Examples 1-87 to include or use a method, wherein selecting at least the first core module and the second core module includes selecting the first core module including a first bore hole portion of a first bore hole and selecting the second core module including a second bore hole portion of a second bore hole different than the first bore hole.

Example 89 can include or use, or can optionally be combined with the subject matter of Examples 1-88 to include or use a method, wherein selecting the plurality of core modules includes selecting at least a third core module.

Example 90 can include or use, or can optionally be combined with the subject matter of Examples 1-89 to include or use a method, wherein selecting at least the third core module includes selecting the third core module including a third bore hole portion of a third bore hole different than at least one of the first bore hole and the second bore hole.

Example 91 can include or use, or can optionally be combined with the subject matter of Examples 1-90 to include or use a method, wherein forming the header shell around the modular header core includes molding the header shell around the modular header core.

Example 92 can include or use, or can optionally be combined with the subject matter of Examples 1-91 to include or use a method, wherein forming the modular header core includes frictionally engaging the plurality of core modules with one another.

Example 93 can include or use, or can optionally be combined with the subject matter of Examples 1-92 to include or use a method, wherein forming the modular header core includes slidingly engaging the plurality of core modules with one another.

Example 94 can include or use, or can optionally be combined with the subject matter of Examples 1-93 to include or use a method, wherein forming the header shell includes forming the header shell from a material similar to a material of the modular header core.

Example 95 can include or use, or can optionally be combined with the subject matter of Examples 1-94 to include or use a method, wherein forming the header shell includes forming the header shell from a material different than a material of the modular header core.

Example 96 can include or use, or can optionally be combined with the subject matter of Examples 1-95 to include or use a method, wherein the plurality of core modules are configured to be engaged in a plurality of different configurations, wherein forming the modular header core includes selecting one of the plurality of different configurations and engaging the plurality of core modules in the one of the plurality of different configurations to form the modular header core.

Example 97 can include or use, or can optionally be combined with the subject matter of Examples 1-96 to include or use a method, wherein forming the modular header core includes engaging the plurality of core modules, wherein the plurality of core modules are configured to be engaged in a particular configuration to form the modular header core.

Example 98 can include, or can be combined with the subject matter of one or any combination of Examples 1-97 to optionally include, subject matter (such as an apparatus, such as an implantable medical device, a method, a means for performing acts, or a machine-readable medium including instructions that, when performed by the machine, cause the machine to perform acts) that can comprise: a device container including an electronic module within the device container; a header coupled to the device container, the header including: a header core including a conductive member electrically coupled to the electronic module within the device container; and a header shell disposed around the header core and attached to the device container; and an antenna coupled to the header core and electrically coupled to the electronic module, wherein a first portion of the header is proximate the antenna, the first portion including a first dielectric constant that is lower than a second dielectric constant of a second portion of the header.

Example 99 can include or use, or can optionally be combined with the subject matter of Examples 1-98 to include or use an implantable medical device, wherein the first portion of the header is disposed between the antenna and the conductive member.

Example 100 can include or use, or can optionally be combined with the subject matter of Examples 1-99 to include or use an implantable medical device, wherein the first portion of the header is disposed between the antenna and the device container.

Example 101 can include or use, or can optionally be combined with the subject matter of Examples 1-100 to include or use an implantable medical device, wherein the first portion of the header includes an antenna attachment feature.

Example 102 can include or use, or can optionally be combined with the subject matter of Examples 1-101 to include or use an implantable medical device, wherein the antenna attachment feature is engaged with the header core.

Example 103 can include or use, or can optionally be combined with the subject matter of Examples 1-102 to include or use an implantable medical device, wherein the antenna attachment feature is integrally formed with the header core.

Example 104 can include or use, or can optionally be combined with the subject matter of Examples 1-103 to include or use an implantable medical device, wherein the first portion includes aerated foam.

Example 105 can include or use, or can optionally be combined with the subject matter of Examples 1-104 to include or use an implantable medical device, wherein the header core forms the first portion and the header shell forms the second portion.

Example 106 can include or use, or can optionally be combined with the subject matter of Examples 1-105 to include or use an implantable medical device, wherein the header core includes the first portion and the second portion.

Example 107 can include or use, or can optionally be combined with the subject matter of Examples 1-106 to include or use an implantable medical device, wherein the first and second portions are molded together.

Example 108 can include or use, or can optionally be combined with the subject matter of Examples 1-107 to include or use an implantable medical device, wherein the first portion is mechanically attached to the second portion.

Example 109 can include or use, or can optionally be combined with the subject matter of Examples 1-108 to include or use an implantable medical device, wherein the conductive member includes a wire.

Example 110 can include or use, or can optionally be combined with the subject matter of Examples 1-109 to include or use an implantable medical device, wherein the conductive member includes a connector block.

Example 111 can include or use, or can optionally be combined with the subject matter of Examples 1-110 to include or use an implantable medical device, wherein the header shell is molded around the header core.

Example 112 can include or use, or can optionally be combined with the subject matter of Examples 1-111 to include or use an implantable medical device, wherein the first portion includes solid filled material.

Example 113 can include or use, or can optionally be combined with the subject matter of Examples 1-112 to include or use an implantable medical device, wherein the solid filled material includes expanded polytetrafluoroethylene.

Example 114 can include or use, or can optionally be combined with the subject matter of Examples 1-113 to include or use an implantable medical device, wherein the solid filled material includes porous glass.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable medical device, comprising:
   a device container including an electronic module within the device container;
   a modular header core, including:
      a header core module including at least one bore hole configured to receive a lead; and
      an antenna attachment module coupled to the header core; and
      an antenna engaged with the antenna attachment module, the antenna attachment module configured to locate the antenna with respect to the header core module; and
   a header shell disposed around the modular header core and the antenna,
   wherein the antenna attachment module includes a first dielectric constant and the header core module includes a second dielectric constant, the first dielectric constant less than the second dielectric constant, wherein a first surface portion of the antenna attachment module is adjacent to the header core module and a second surface portion of the antenna attachment module is adjacent to the device container such that the antenna attachment module is positioned between the antenna and the device container and between the antenna and the header core module.

2. The implantable medical device of claim 1, wherein a first mating surface of the antenna attachment module and a second mating surface of the header core module engage to form a connection to couple and maintain the position of the antenna attachment module with respect to the header core module while the header shell is disposed.

3. The implantable medical device of claim 2, wherein the connection is a tab-and-slot configuration.

4. The implantable medical device of claim 2, wherein the connection is a pin-and-hole configuration.

5. The implantable medical device of claim 2, wherein the connection includes a snap-together configuration.

6. The implantable medical device of claim 2, wherein the connection includes a mating slide-together configuration.

7. The implantable medical device of claim 1, wherein the antenna attachment module includes an antenna attachment feature to couple the antenna to the antenna attachment module.

8. The implantable medical device of claim 7, wherein the antenna attachment feature includes ridges spaced to accommodate the antenna between the ridges.

9. The implantable medical device of claim 8, wherein one or more of the ridges of the antenna attachment feature are disposed between portions of the antenna and are configured to maintain spacing between the portions of the antenna.

10. The implantable medical device of claim 7, wherein the antenna attachment feature includes a retention feature configured to grip at least a portion of the antenna.

11. The implantable medical device of claim 7, wherein the antenna attachment feature is configured to maintain a substantially constant distance between the antenna and a patient.

12. The implantable medical device of claim 7, wherein the antenna attachment feature includes a channel.

13. The implantable medical device of claim 12, wherein the channel includes one or more portions configured to be crimped to retain the antenna within the channel.

14. A method of forming an implantable medical device, the method comprising:
   engaging a header core module with an antenna attachment module to form a modular header core, wherein the antenna attachment module has a first dielectric constant and the header core module has a second dielectric constant, the first dielectric constant less than the second dielectric constant;
   coupling an antenna to the antenna attachment module such that a first surface portion of the antenna attachment module is adjacent to the header core module and a second surface portion of the antenna attachment module is adjacent to the device container such that the antenna attachment module is positioned between the antenna and the device container and between the antenna and the header core module; and forming a header shell around the modular header core.

15. The method of claim 14, wherein engaging the header core module with the antenna attachment module includes detachably engaging the header core module with the antenna attachment module.

16. An implantable medical device comprising:
   a device container including an electronic module within the device container; a header core including a header core portion including at least one bore hole configured to receive a lead and an antenna attachment feature;
   an antenna engaged with the antenna attachment feature and electrically coupled with the electronic module within the device container, the antenna attachment feature configured to locate the antenna with respect to the header core, wherein the antenna attachment feature includes a first dielectric constant and the header core module includes a second dielectric constant, the first dielectric constant different from less than the second dielectric constant, wherein at least a first surface portion of the antenna attachment module is adjacent to positioned between the header core module and a second surface portion of the antenna attachment feature is adjacent to the device container such that the antenna attachment feature is positioned between the antenna and the device container and between the antenna and the header core module; and a molded header shell disposed around the header core and attached to the device container, the header shell disposed around and configured to retain the antenna.

17. The implantable medical device of claim 16, wherein the antenna attachment feature includes a removable portion configured to detachably engage with the header core portion, prior to the molded header shell being disposed.

* * * * *